US011505783B2

(12) United States Patent
Rezania

(10) Patent No.: US 11,505,783 B2
(45) Date of Patent: *Nov. 22, 2022

(54) DIFFERENTIATION OF HUMAN EMBRYONIC STEM CELLS

(71) Applicant: Janssen Biotech, Inc., Horsham, PA (US)

(72) Inventor: Alireza Rezania, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 511 days.

This patent is subject to a terminal disclaimer.

(21) Appl. No.: 16/586,786

(22) Filed: Sep. 27, 2019

(65) Prior Publication Data

US 2020/0024578 A1 Jan. 23, 2020

Related U.S. Application Data

(60) Continuation of application No. 15/978,935, filed on May 14, 2018, now Pat. No. 10,494,609, which is a continuation of application No. 14/719,124, filed on May 21, 2015, now Pat. No. 9,969,982, which is a division of application No. 12/277,904, filed on Nov. 25, 2008, now Pat. No. 9,062,290.

(60) Provisional application No. 60/990,529, filed on Nov. 27, 2007.

(51) Int. Cl.
C12N 5/071 (2010.01)

(52) U.S. Cl.
CPC ......... *C12N 5/0678* (2013.01); *C12N 5/0676* (2013.01); *C12N 2501/105* (2013.01); *C12N 2501/117* (2013.01); *C12N 2501/12* (2013.01); *C12N 2501/15* (2013.01); *C12N 2501/155* (2013.01); *C12N 2501/16* (2013.01); *C12N 2501/335* (2013.01); *C12N 2501/385* (2013.01); *C12N 2501/40* (2013.01); *C12N 2501/41* (2013.01); *C12N 2501/415* (2013.01); *C12N 2501/42* (2013.01); *C12N 2501/70* (2013.01); *C12N 2501/727* (2013.01); *C12N 2501/998* (2013.01); *C12N 2501/999* (2013.01); *C12N 2506/02* (2013.01); *C12N 2533/90* (2013.01)

(58) Field of Classification Search
CPC .................................................... C12N 5/0678
See application file for complete search history.

(56) References Cited

U.S. PATENT DOCUMENTS

| | | | |
|---|---|---|---|
| 5,942,435 A | 8/1999 | Wheeler | |
| 9,062,290 B2* | 6/2015 | Rezania | .......... A61P 1/18 |
| 9,969,982 B2 | 5/2018 | Rezania | |
| 10,494,609 B2* | 12/2019 | Rezania | ............... C12N 5/0676 |
| 2003/0138948 A1 | 7/2003 | Fisk et al. | |
| 2005/0260749 A1 | 11/2005 | Odorico et al. | |
| 2005/0266554 A1 | 12/2005 | D'Amour et al. | |
| 2006/0003446 A1 | 1/2006 | Keller et al. | |
| 2007/0122905 A1 | 5/2007 | D'Amour et al. | |
| 2007/0254359 A1 | 11/2007 | Rezania et al. | |
| 2009/0170198 A1 | 7/2009 | Rezania | |
| 2009/0263896 A1 | 10/2009 | Kelly et al. | |
| 2010/0015100 A1 | 1/2010 | Xu | |
| 2011/0014703 A1 | 1/2011 | Xu et al. | |
| 2011/0151560 A1 | 6/2011 | Xu | |
| 2011/0281355 A1 | 11/2011 | Xu | |
| 2012/0052576 A1 | 3/2012 | Rezania | |
| 2014/0186953 A1 | 7/2014 | Rezania | |

FOREIGN PATENT DOCUMENTS

| | | |
|---|---|---|
| EP | 2604685 B1 | 3/2017 |
| WO | 2005097977 A2 | 10/2005 |
| WO | 2006016999 A1 | 2/2006 |
| WO | 2005116073 A3 | 12/2006 |
| WO | 2009018453 A1 | 2/2009 |
| WO | 2006105152 A3 | 6/2009 |
| WO | 2009070592 A3 | 10/2009 |
| WO | 2009132083 A3 | 3/2010 |
| WO | 2011079017 A2 | 6/2011 |
| WO | 2012030540 A3 | 5/2012 |
| WO | 2013095953 A1 | 6/2013 |
| WO | 2014105543 A1 | 7/2014 |

(Continued)

OTHER PUBLICATIONS

Micallef S J et al, "Retinoic acid induces Pdx1-positive endoderm in differentiating mouse embryonic stem cells", Diabetes, American Diabetes Association, US, (Feb. 1, 2005), vol. 54, No. 2, ISSN 0012-1797, pp. 301-305.

Altirriba, et al. "The Role of Transmembrane Protein 27 (TMEM27) in islet physiology and its potential use as a beta cell mass biomarker." Diabetologia (2010): 53: 1406-1414.

Banerjee and Otonkoski, "A simple two-step protocol for the purification of human pancreatic beta cells." Diabetologia (2009) 52: 621-625.

(Continued)

*Primary Examiner* — Ram R Shukla
*Assistant Examiner* — David A Montanari
(74) *Attorney, Agent, or Firm* — Klarquist Sparkman, LLP

(57) ABSTRACT

The present invention provides methods to promote the differentiation of pluripotent stem cells and the products related to or resulting from such methods. In particular, the present invention provides an improved method for the formation of pancreatic hormone expressing cells and pancreatic hormone secreting cells. In addition, the present invention also provides methods to promote the differentiation of pluripotent stem cells without the use of a feeder cell layer and the products related to or resulting from such methods. The present invention also provides methods to promote glucose-stimulated insulin secretion in insulin-producing cells derived from pluripotent stem cells.

11 Claims, 56 Drawing Sheets

(56) References Cited

FOREIGN PATENT DOCUMENTS

| WO | 2014105546 A1 | 7/2014 |
|---|---|---|
| WO | 2015002724 | 3/2015 |

OTHER PUBLICATIONS

Brewer, et al. "Optimized Survivial of Hippocampal Neurons in B27-Supplemented Neurobasal, a New Serum-free Medium Combination." Journal of Neuroscience Research 35: 567-576 (1993).
Cheng, et al. "Self-Renewing Endodermnal Progenitor Lines Generated From Human Pluripotent Stem Cells." Cell Stem Cell, vol. 10, No. 4, Apr. 1, 2012, pp. 371-384.
Cho, et al. "Inhibition of Activin/Nodal Signalling is necessary for pancreatic differentiatoin of human pluripotent stem cells." Diabetologia (2012) 55: 3284-3295.
Cuny, et al. Structure-activity relationship study of bone morpogenetic protein (BMP) signlaing inhibitors. Bioorg Med Chem Lett. Aug. 1, 2008; 18(15): 4388-4392.
D'amour K A et al, "Production of pancreatic hormone-expressing endocrine cells from human embryonic stem cells", Nature Biotechnology, Nature Publishing Group, Newyork, NY, US, (Jan. 1, 2006), vol. 24, No. 11, ISSN 1087-0156, pp. 1392-1401.
Declaration of Maria Cristina Nostro, Ph.D. dated Jul. 22, 201 in Toronto, Canada.
Fraker, et al. "Enhanced Oxygenation Promotes B-Cell Differentiation in Vitro." Stem Cells 2007; 25: 3155-3164.
Guillemain, et al., Glucose Is Necessary For Embryonic Pancreatic Endocrine Cell Differentiation*, The Journal Of Biological Chemistry, May 18, 2007, pp. 15228-15237, vol. 282 Issue 20.
Hald, et al. "Pancreatic Islet and Progenitor Cell Surface Markers with Cell Sorting Potential". Diabetologia (2012) 55: 154-165.
Heinis, et al., Oxygen Tension Regulates Pancreatic Beta-Cell Differentiation Through Hypoxia-Inducible Factor 1x, Diabetes, 2010, pp. 662-669, vol. 59.
Inman, et al., SB-431542 is a Potent and Specific Inhibitor of Transforming Growth Factor-B Superfamily Type I Activing Receptor-Like Kinase (ALK) Receptors Alf.4, Alf.5, and ALK7, Molecular Pharmacology, 2002, pp. 65-74, vol. 62, No. 1.
Iype, et al. "The Transcriptional Repressor Nkx6.1 Also Functions as Deoxyribonucleic Acid Context-Dependent Transcriptional Activator During Pancreatic B-cell Differntiation: Evidence for Feedback Acitivation of the nkx6.1 Gene by Nkx6.1" Molecular Endocrinology 18(6): 1363-1375.
Korytnikov, et al. "Generation of Polyhormonal and Multipotent pancreatic progenitor lineages form human pluripotent stem cells." Methods, vol. 101, May 15, 2016, pp. 56-64.
Kubo A et al, "Development of definitive endoderm from embryonic stem cells in culture", Development, Company of Biologists, Cambridge, GB, (Apr. 1, 2004), vol. 131, No. 7, ISSN 0950-1991, pp. 1651-1662.
Kunisada, et al., Small molecules induce efficient differentiation into insulin-producing cells from human induced pluripotent stem cells, Stem Cell Research, Oct. 11, 2011, pp. 274-284, vol. 8.
Leontovyc, et al. The Effect of Epigenetic Factors on Differentiation of Pancreatic Progenitor Cells into Insulin-Producing Cells. Transplant. Proc., 2011, vol. 43, pp. 3212-3216.
Mfopou, et al. "Noggin, Retinoids, and Fibroblast Growth Factor Regulate Hepatic or Pancreatic Fate of Human Embryonic Stem Cells." Gastroenterology 2010; 138:2233-2245.
Micallef, et al. "INSGFP/W Human Emryonic Stem Cells Facilitate Isolation of in vitro derived insulin-producing cells." Diabetologia (2012) 55: 694-706.
Pagliuca et al., How to Make a Functional Beta-Cell, Development, 2013, pp. 2472-2483, vol. 140, No. 2.
Skoudy A et al, "Transforming growth factor (TGF)beta, fibroblast growth factor (FGF) and retinoid signalling pathways promote pancreatic exocrine gene expression in mouse embryonic stem cells", Biochemical Journal, The Biochemical Society, London, (May 1, 2004), vol. 379, No. Pt 3, ISSN 0264-6021, pp. 749-756.
Stassi, et al. "Expression of Apotosis-Inducing CD95 (Fas/Apo-1) on Human B-Cells Sorted by Flow-Cytometry and Cultured in Vitro." Transplantation Proceedings, vol. 27, No. 6 Dec. 1995: 3271-3275.
Thermofisher Scientific, B-27 Serum-Free Supplement 50x Liquid, Technical Resources, 2016, URL:https://www.thermofisher.com/nl/en/home/technical-resources/media-formulation.250.html, retrieved from the internet.
Agulnick et al., Stem Cells Transl Med, 2015, Insulin-Producing Endocrine Cells Differentiated In Vitro from Human Embryonic Stem Cells Function in Macroencapsulation Devices In Vivo, 4: 1-9.
Allegrucci and Young, "Differences between human embryonic stem cell lines," Human Reproduction Update 13(2): 103-120 (Advance Access publication Aug. 26, 2006).
Bandyopadhyay et al., "Inhibition of pulmonary and skeletal metastasis by a transforming growth factor-β type I receptor kinase inhibitor," Cancer Research 66(13): 6714-6721 (Jul. 1, 2006).
Brevini et al., "No shortcuts to pig embryonic stem cells," Theriogenology 74: 544-550 (2010).
Cai et al., Prospectively Isolated NGN3-Expressing Progenitors from Human Embryonic Stem Gells give Rise to Pancreatic Endocrine Cells, Stem Cells Translational Medicine, e-pub, Feb. 2014, pp. 489-499, vol. 3, No. 4.
D'Amour et al., "Production of pancreatic hormone-expressing endocrine cells from human embryonic stem cells," Nature Biotechnology 24(11): 1392-1401 (Nov. 2006).
Fryer, et al., Generating B-cells in vitro : progress towards a Holy Grail, Curr Opin Endocrinol Diabetes obes, 2013, pp. 112-117, vol. 20 Issue 2.
Gellibert et al., "Identification of 1,5-Naphthyridine derivatives as a novel series of potent and selective TGF-β type I receptor inhibitors," Journal of MedicinalChemistry 47(18): 4494-4506 (2004).
Ginis et al., "Differences between human and mouse embryonic stem cells," Developmental Biology 269: 360-380 (2004).
Inami et al., "Differentiation of induced pluripotent stem cells to thymic epithelial cells by phenotype." Immunology and Cell Biology 1-8 (Epub Aug. 3, 2010).
Inman et al., "S8-431542 is a potent and specific inhibitor of transforming growth factor-β superfamily type I activin receptor-like kinase (ALK) receptors ALK4,ALK5, and ALK7," Molecular Pharmacology 62(1): 65-74 (2002).
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Ku et al., Committing Embryonic Stem Cells to Early Endocrine Pancreas In Vitro, Stem Cells, 2004, vol. 22, pp. 1205-1217, AlphaMed Press.
McLean et al., "Activin A efficiently specifies definitive endoderm from human embryonic stem cells only when phosphatidylinositol 3-kinase signaling issuppressed," Stem Cells 25: 29-38 (2007).
Munos et al., "Conventional pluripotency markers are unspecific for bovine embryonic-derived cell-lines," Theriogenology 69: 1159-1164 (2008).
Murtaugh, et al., Notch Signaling Controls Multiple Steps of Pancreatic Differentiation, 2003, PNAS, vol. 100, No. 25, pp. 14928-14925.
Nishimura et al., A Switch from MafB to MafA Expression Accompanies Differentiation to B-Cells, Developmental Biology, 2006, vol. 293, pp. 526-539.
Nostro, et al., Stage-Specific Signaling Through TGF Family Members and WNT Regulates Patterning and Pancreatic Specification of Human Pluripotent Stem Cells, Development, 2011, pp. 881-871, vol. 138, Issue 5.
Pagliuca, F.W., et al., How to Make a Functional Beta-Cell, Development, Jun. 15, 2013, pp. 2472-2483, vol. 140, No. 12.
Paris and Stout, "Equine embryos and embryonic stem cells: Defining reliable markers of pluripotency," Theriogenoiogy 74: 516-524 (2010).
Phillips, et al., Directed Differentiation of Human Embryonic Stem Cells into the Pancreatic Endocrine Lineage, Stem Cells and Development, 2007, pp. 561-578 XP009090586, vol. 16, No. 4.

(56) References Cited

OTHER PUBLICATIONS

Rezania et al., "Reversal of diabetes with insulin-producing cells derived in vitro from human pluripotent stem cells," Nature Biotechnology 32(11): 1121-1133 (e-PUB Sep. 11, 2014).
Rezania et al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Rezania, Production of Functional Glucagon-Secreting-Cells from Human Embryonic Stem Cells, Diabetes, 2011, pp. 239-247, vol. 60, Issue 1.
Sato, et al., "Molecular Signature of Human Embryonic Stem Cells and its Comparison with the Mouse," Developmental Biology 260: 404-413 (Apr. 23, 2003).
Skoudy et al., "Transforming growth factor TGFβ, fibroblast growth factor FGF and retinold signaling pathways promote pancreatic exocrine gene expression in mouse embryonic stem cells," Biochemistry J., 2004, 379: 749-756, Biochemical Society, GB.
Wei et al., "Transcriptome profiling of human and murine ESCs identifies divergent paths required to maintain the stem cell state," Stem Cells 23: 165-185(2005).

\* cited by examiner

FIG. 8A
4X
FIG. 8B
10X
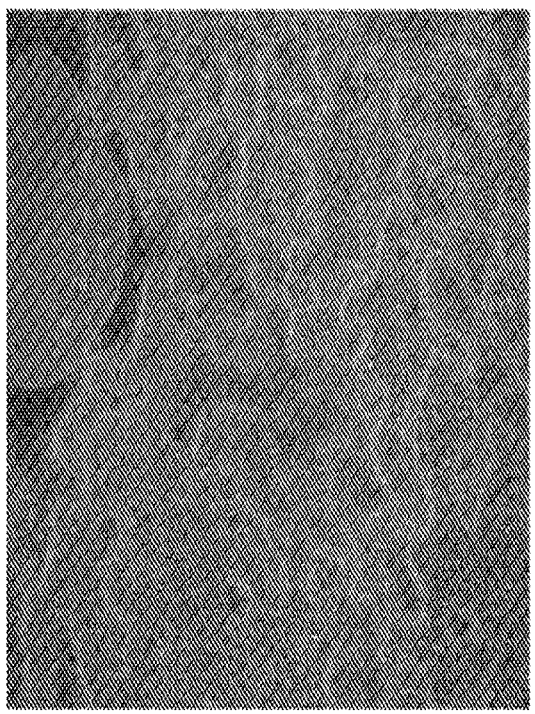
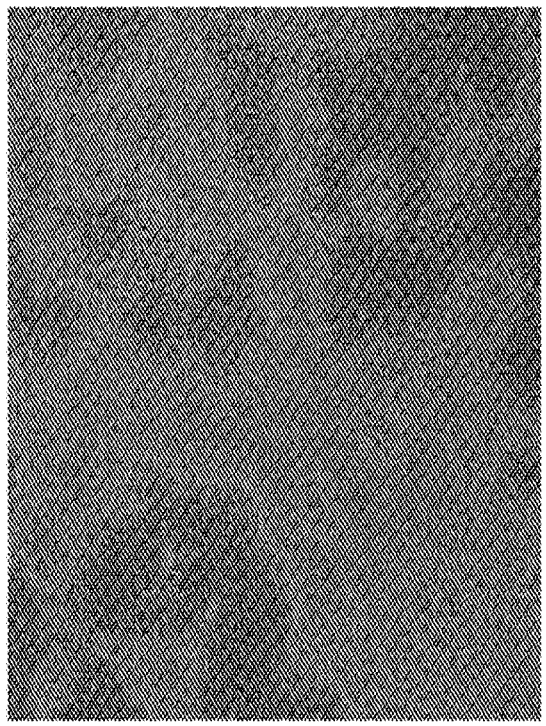
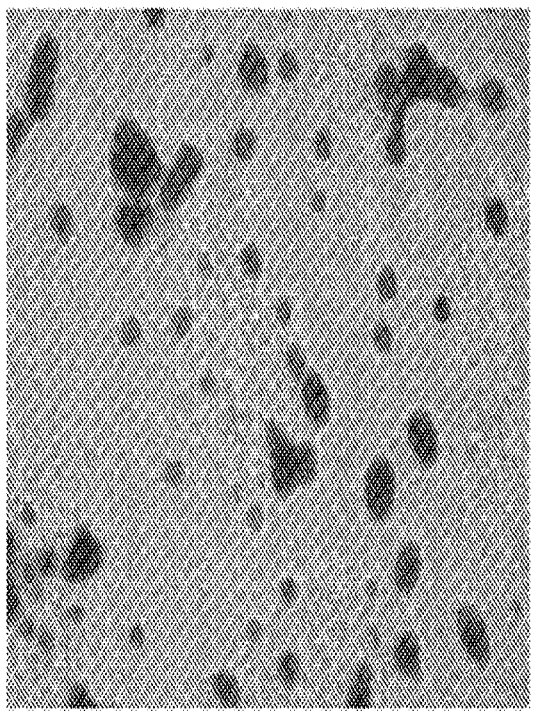
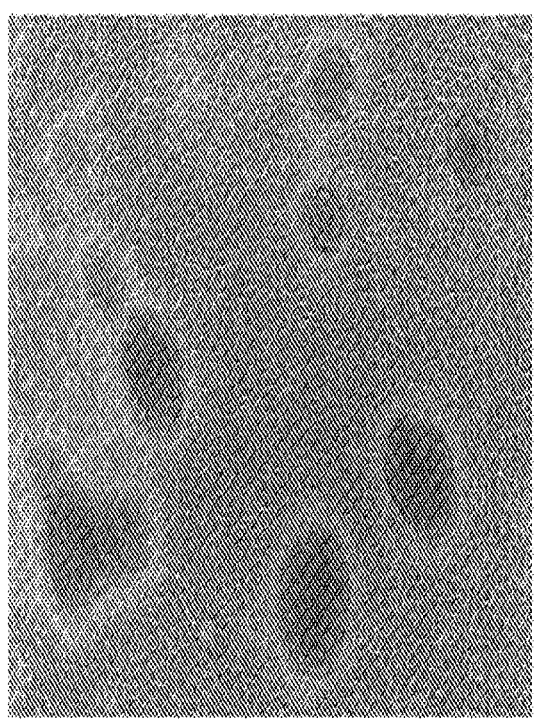
FIG. 8C
FIG. 8D Insulin-10X

10X

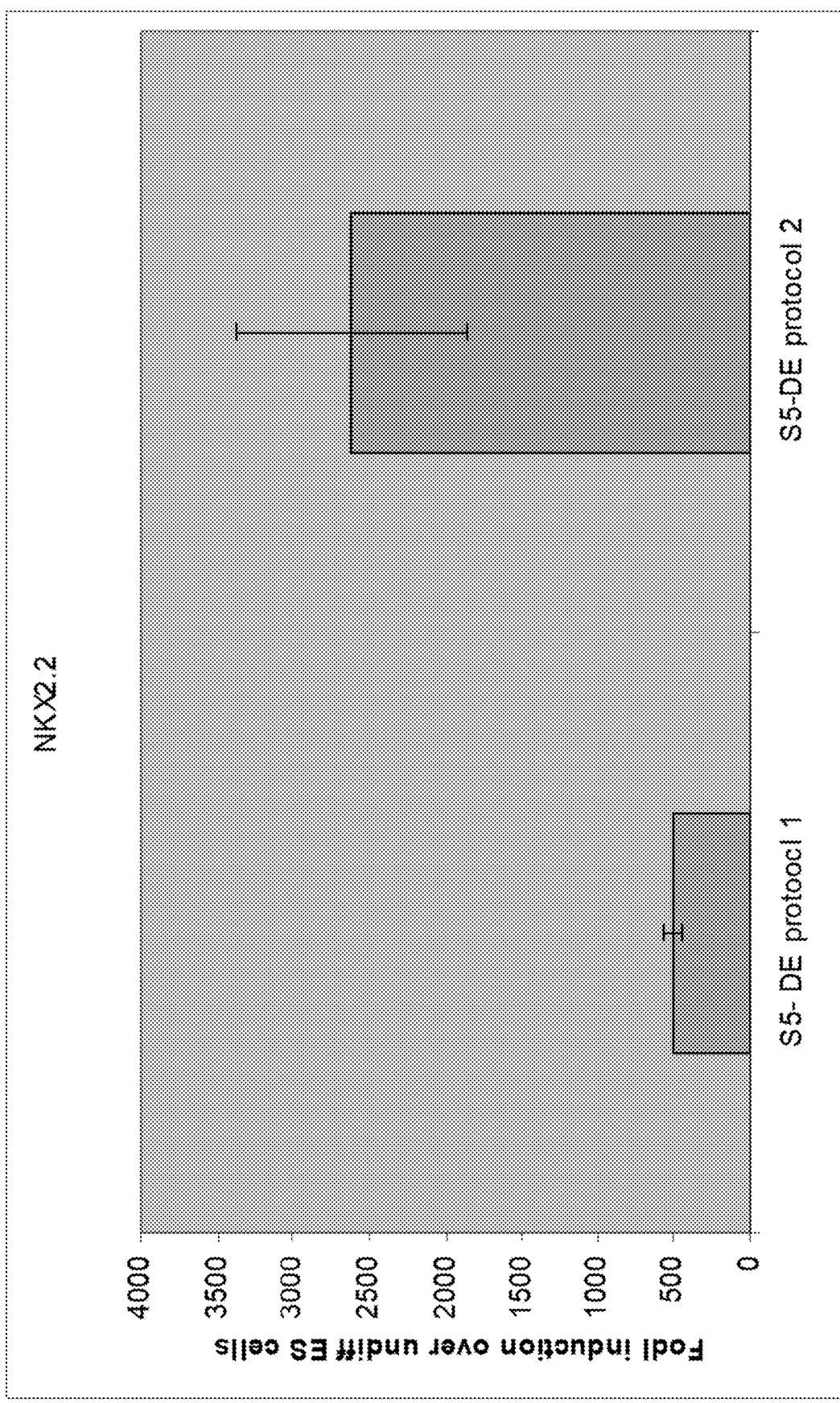

FIG. 16C
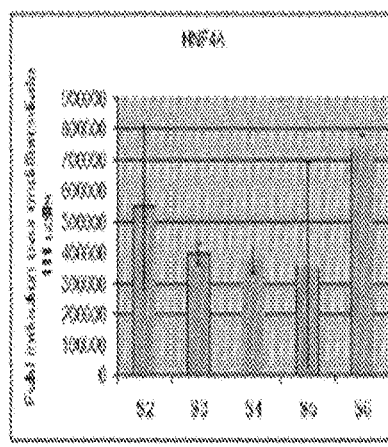
FIG. 16D
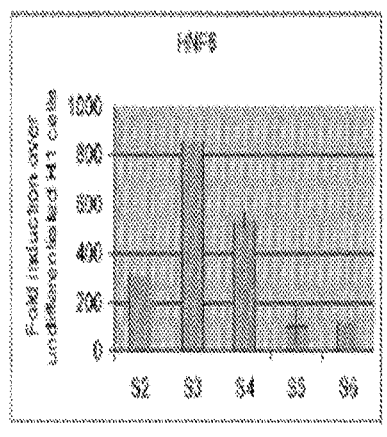
FIG. 16E
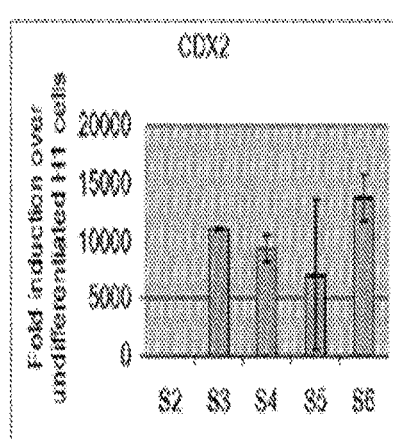
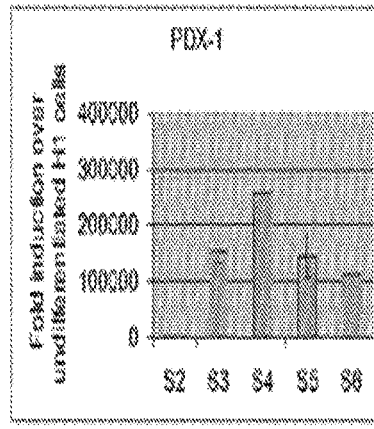
FIG. 16F
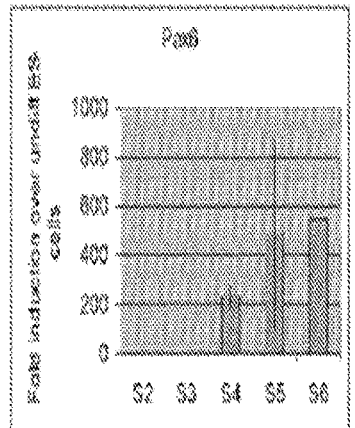
FIG. 16G
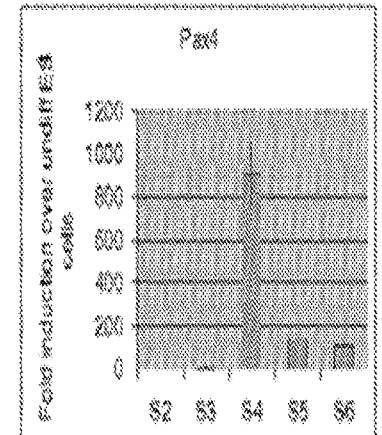
FIG. 16H FIG. 20A
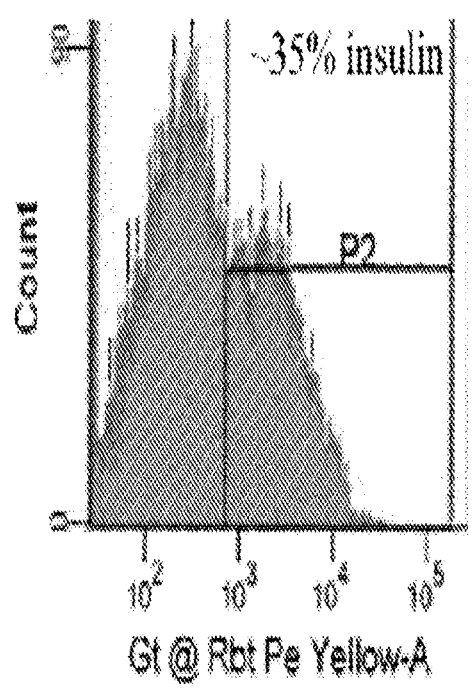
FIG. 20B
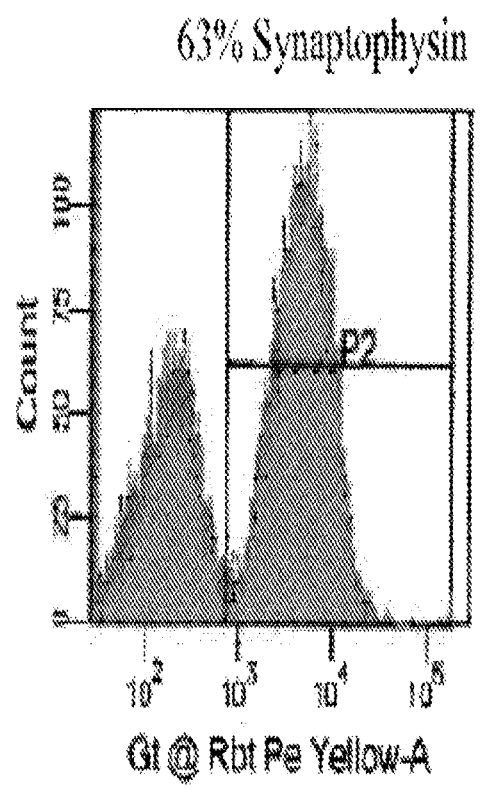
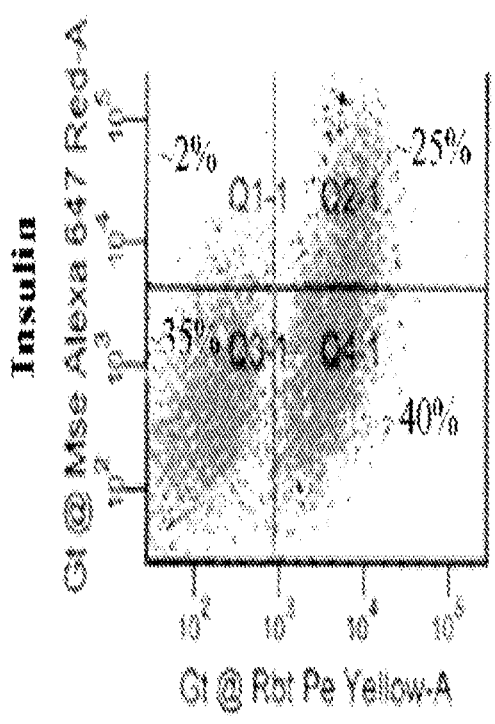
FIG. 20C Synaptophysin Insulin

DIFFERENTIATION OF HUMAN EMBRYONIC STEM CELLS

CROSS-REFERENCE TO RELATED APPLICATIONS

This is continuation of U.S. patent application Ser. No. 15/978,935, filed May 14, 2018, which is a continuation of U.S. patent application Ser. No. 14/719,124, filed May 21, 2015, issued as U.S. Pat. No. 9,969,982, which is a divisional of U.S. patent application Ser. No. 12/277,904, filed Nov. 25, 2008, issued as U.S. Pat. No. 9,062,290, which claims the benefit of U.S. Provisional Patent Application No. 60/990,529, filed Nov. 27, 2007, the contents of all of which are incorporated by reference in their entireties.

FIELD OF THE INVENTION

The present invention provides methods to promote the differentiation of pluripotent stem cells and the products related to or resulting from such methods. In particular, the present invention provides an improved method for the formation of pancreatic hormone expressing cells and pancreatic hormone secreting cells. In addition, the present invention also provides methods to promote the differentiation of pluripotent stem cells without the use of a feeder cell layer and the products related to or resulting from such methods. The present invention also provides methods to promote glucose-stimulated insulin secretion in insulin-producing cells derived from pluripotent stem cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3beta, GATA4, Mix11, CXCR4 and Sox-17.

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express Oct-4 and TERT, as detected by RT-PCR.

Pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al. (Nature Biotechnology 18: 399-404 (2000)) and Thompson et al. (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al., (Stem Cells 21: 546-556, 2003) evaluated a panel of 11 different human adult, fetal and neonatal feeder cell layers for their ability to support human pluripotent stem cell culture. Richards et al., states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al. (Stem Cells 23: 1221-1227, 2005) discloses methods for the long-term growth of human pluripotent stem cells on feeder cell layers derived from human embryonic stem cells.

In another example, Stojkovic et al. (Stem Cells 2005 23: 306-314, 2005) disclose a feeder cell system derived from the spontaneous differentiation of human embryonic stem cells.

In a further example, Miyamoto et al. (Stem Cells 22: 433-440, 2004) disclose a source of feeder cells obtained from human placenta.

Amit et al. (Biol. Reprod 68: 2150-2156, 2003) discloses a feeder cell layer derived from human foreskin.

In another example, Inzunza et al. (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al. (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al. (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al. (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Pluripotent stem cells may be cultured and differentiated on a tissue culture substrate coated with an extracellular matrix. The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

Formation of the pancreas arises from the differentiation of definitive endoderm into pancreatic endoderm. Cells of the pancreatic endoderm express the pancreatic-duodenal homeobox gene, Pdx1. In the absence of Pdx1, the pancreas fails to develop beyond the formation of ventral and dorsal buds. Thus, Pdx1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled 13 cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGF-β2 reproducibly yielded a higher proportion of Pdx1 positive cells (Genes Cells. 2005 June; 10(6): 503-16).

Gordon et al. demonstrated the induction of brachyury+/HNF-3beta+ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristic of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology, 24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al., Stem Cells 2006; 24:1923-1930).

In another example, Odorico et al. reports methods for direct in vitro differentiation of mammalian pluripotent stem cells to cells of the pancreatic lineage. The methods involve culturing the stem cells in the presence of an effective amount of a bone morphogenetic protein to induce differentiation in the direction of mesendoderm. These mesendoderm cells are further cultured to form embryoid bodies (EBs) enriched for definitive endoderm committed cells, which under defined conditions terminally differentiate to cells of the pancreatic lineage (US20070259423).

In another example, Tulachan et al. (Developmental Biology, 305, 2007, Pgs 508-521) state: "Inhibition of TGF-B signaling in the embryonic period may thus allow pancreatic epithelial cells to progress towards the endocrine lineage".

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells, and possess the ability to secrete insulin in response to changes in glucose concentration. An alternative approach has been taken to improve the efficiency of differentiating human embryonic stem cells toward pancreatic endocrine cells that are able to secrete insulin in response to changes in glucose levels.

SUMMARY

In one embodiment, the present invention provides a method for producing cells capable of glucose-stimulated insulin secretion from pluripotent stem cells, comprising the steps of: Culturing the pluripotent stem cells,
 b. Differentiating the pluripotent stem cells into cells expressing markers characteristic of the definitive endoderm lineage,
 c. Differentiating the cells expressing markers characteristic of the definitive endoderm lineage into cells expressing markers characteristic of the pancreatic endoderm lineage, and
 d. Differentiating the cells expressing markers characteristic of the pancreatic endoderm lineage into cells expressing markers characteristic of the pancreatic endocrine lineage.

In one embodiment, the present invention provides a method for promoting glucose-stimulated insulin secretion in cells expressing markers characteristic of the pancreatic endocrine lineage derived from pluripotent stem cells, comprising the steps of:
 a. Culturing the pluripotent stem cells,
 b. Differentiating the pluripotent stem cells into cells expressing markers characteristic of the definitive endoderm lineage,
 c. Differentiating the cells expressing markers characteristic of the definitive endoderm lineage into cells expressing markers characteristic of the pancreatic endoderm lineage, and
 d. Differentiating the cells expressing markers characteristic of the pancreatic endoderm lineage into cells expressing markers characteristic of the pancreatic endocrine lineage.

In one embodiment, cells expressing markers characteristic of the pancreatic endoderm lineage are differentiated from cells expressing markers characteristic of the definitive endoderm lineage by treating cells expressing markers characteristic of the definitive endoderm lineage by any one of the following methods:
 a. Treating the cells expressing markers characteristic of the definitive endoderm lineage with a fibroblast growth factor and a hedgehog signaling pathway inhibitor, then removing the medium containing the fibroblast growth factor and the hedgehog signaling pathway inhibitor and subsequently culturing the cells in medium containing retinoic acid, a fibroblast growth factor and the hedgehog signaling pathway inhibitor, or b. Treating the cells expressing markers characteristic of the definitive endoderm lineage with retinoic acid and at least one fibroblast growth factor, or c. Treating the cells expressing markers characteristic of the definitive endoderm lineage with retinoic acid, a sonic hedgehog inhibitor, at least one fibroblast growth factor, and at least one factor capable of inhibiting BMP, or d. Treating the cells expressing markers characteristic of the definitive endoderm lineage with retinoic acid, a sonic hedgehog inhibitor, at least one fibroblast growth factor, and a netrin, or e. Treating the cells expressing markers characteristic of the definitive endoderm lineage with retinoic acid, a sonic hedgehog inhibitor, at least one fibroblast growth factor, at least one factor capable of inhibiting BMP, and a netrin, or f. Treating the cells expressing markers characteristic of the definitive endoderm lineage with at least one fibroblast growth factor and a sonic hedgehog inhibitor, then removing the at least one fibroblast growth factor and the sonic hedgehog inhibitor and subsequently treating the cells with a sonic hedgehog inhibitor, at least one fibroblast growth factor, and retinoic acid, or g. Treating the cells expressing markers characteristic of the definitive endoderm lineage with at least one fibroblast growth factor and a sonic hedgehog inhibitor, then removing the at least one fibroblast growth factor and the sonic hedgehog inhibitor and subsequently treating the cells with a sonic hedgehog inhibitor, at least one fibroblast growth factor, retinoic acid, and at least one factor capable of inhibiting BMP, or h. Treating the cells expressing markers characteristic of the definitive endoderm lineage with at least one fibroblast growth factor and a sonic hedgehog inhibitor, then removing the at least one fibroblast growth factor and the sonic hedgehog inhibitor and subsequently treating the cells with a sonic hedgehog inhibitor, at least one fibroblast growth factor, retinoic acid, and a netrin, or i. Treating the cells expressing markers characteristic of the definitive endoderm lineage with at least one fibroblast growth factor and a sonic hedgehog inhibitor, then removing the at least one fibroblast growth factor and the sonic hedgehog inhibitor and subsequently treating the cells with a sonic hedgehog inhibitor, at least one fibroblast growth factor, retinoic acid, at least one factor capable of inhibiting BMP, and a netrin.

In one embodiment, cells expressing markers characteristic of the pancreatic endocrine lineage are differentiated from cells expressing markers characteristic of the pancreatic endoderm lineage by treating cells expressing markers characteristic of the pancreatic endoderm lineage by any one of the following methods:

a. Culturing the cells expressing markers characteristic of the pancreatic endoderm lineage in medium containing a γ secretase inhibitor and a GLP-1 agonist, then removing the medium containing a γ secretase inhibitor and a GLP-1 agonist and subsequently culturing the cells in medium containing a GLP-1 agonist, IGF-1 and HGF, or b. Culturing the cells expressing markers characteristic of the pancreatic endoderm lineage in medium containing a GLP-1 agonist, then removing the medium containing a GLP-1 agonist and subsequently culturing the cells in medium containing a GLP-1 agonist, IGF-1 and HGF, or c. Culturing the cells expressing markers characteristic of the pancreatic endoderm lineage in medium containing a γ secretase inhibitor and a GLP-1 agonist, or d. Culturing the cells expressing markers characteristic of the pancreatic endoderm lineage in medium containing a GLP-1 agonist, or e. Treating the cells expressing markers characteristic of the pancreatic endoderm lineage with a factor that inhibits the Notch signaling pathway, or f. Treating the cells expressing markers characteristic of the pancreatic endoderm lineage with a factor that inhibits the TGF-βR-1 pathway, or g. Treating the cells expressing markers characteristic of the pancreatic endoderm lineage with a factor that inhibits the Notch signaling pathway, and a factor that inhibits the TGF-βR-1 pathway, or h. Culturing the cells expressing markers characteristic of the pancreatic endoderm lineage in medium containing from about 10 mM to about 20 mM glucose and a GLP-1 agonist.

BRIEF DESCRIPTION OF THE DRAWINGS

FIG. 1A) refers to the method reported in US patent application Ser. No. 11/736,908, and FIG. 1B) and FIG. 1C) are the methods of the present invention.

FIGS. 5A-5D show real-time PCR analysis of cells of the human embryonic stem cell line H1, differentiated according to the methods disclosed in Example 5. Effect of 1-10 μm ALK5 inhibitors I and II, on the expression of: FIG. 5A) glucagon, FIG. 5B) insulin, FIG. 5C) PDX-1, FIG. 5D)

Figure 1A:
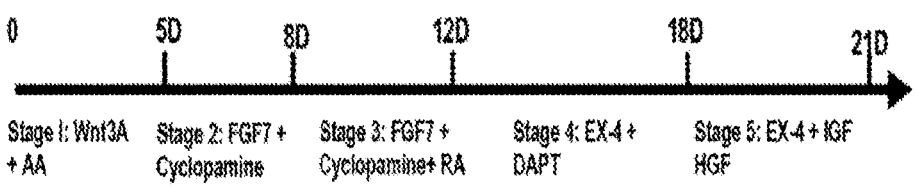
FIGS. 1A-1C show an outline of the differentiation protocol used in the present invention.

NeuroD, is depicted at stages 4 to 5. Control treatment did not include any ALK5 inhibitor during the differentiation process.

FIGS. 6A-6G show real-time PCR analysis of cells of the human embryonic stem cell line H1, differentiated according to the methods disclosed Example 6. Combined effects of 1 µM ALK5 inhibitor and 0-500 ng/ml of recombinant human Noggin on expression of FIG. 6A) albumin, FIG. 6B) CDX2, FIG. 6C) insulin, FIG. 6D) glucagon, FIG. 6E) PDX-1, FIG. 6F) NeuroD, and FIG. 6G) NKX2.2, is depicted at stages 3 to 5. ALK5 inhibitor was added at stages 4 and 5 and Noggin was added at stage 3.

FIGS. 7A-7F show real-time PCR analysis of cells of the human embryonic stem cell line H1, differentiated according to the methods disclosed in Example 7. Combined effects of 1 µM ALK5 inhibitor and 100 ng/ml of recombinant human Noggin on expression of FIG. 7A) insulin, FIG. 7B) glucagon, FIG. 7C) ngn3, FIG. 7D) NeuroD, FIG. 7E) CDX-2, FIG. 7F) PDX-1, is depicted at stages 4 and 5. ALK5 inhibitor was added at stages 4 and 5 and Noggin was added at stage 3, 4, or 3 and 4.

FIGS. 8A-8D show the morphology of cells differentiated according the methods disclosed in Example 7. FIG. 8A) 4× phase contrast image of stage 5 cells at day 6, FIG. 8B) 10× phase contrast image of stage 5 cells at day 6, FIG. 8C) 4× phase contrast image of stage 5 cells at day 12, FIG. 8D) 10× phase contrast image of stage 5 cells at day 12.

Figure 9A:
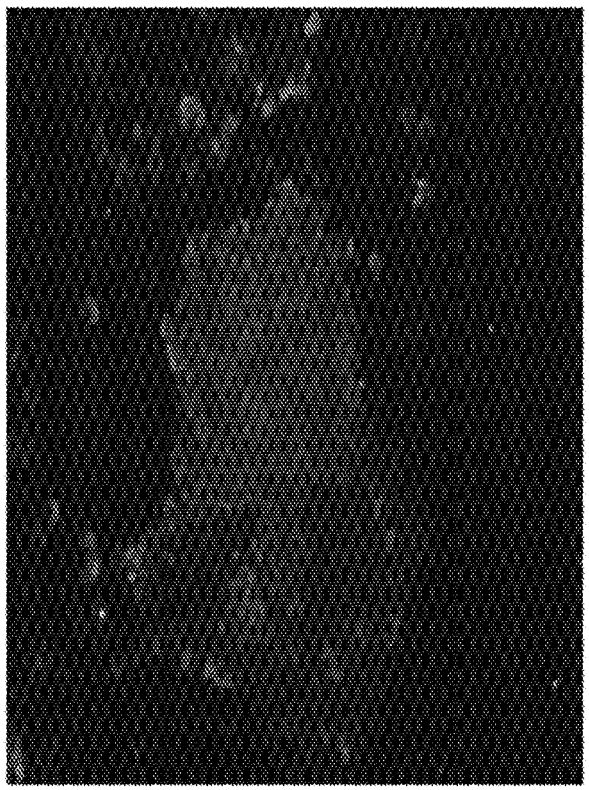
Figure 9B:
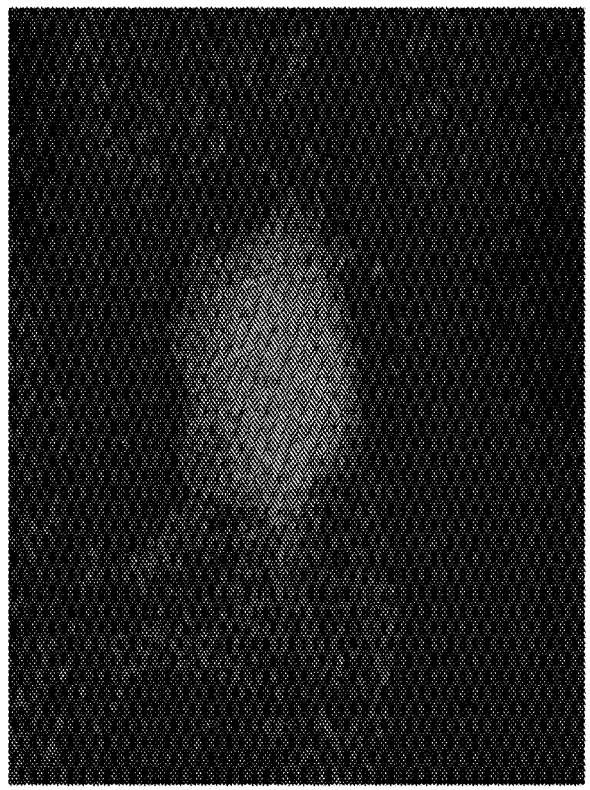

FIGS. 9A-9B show the immunofluorescent images of cells, differentiated according to the methods disclosed in Example 7. Cells are at stage 5 at day 12. FIG. 9A) Insulin staining of a single cluster along with FIG. 9B) DAPI nuclear stain.

Figure 10:
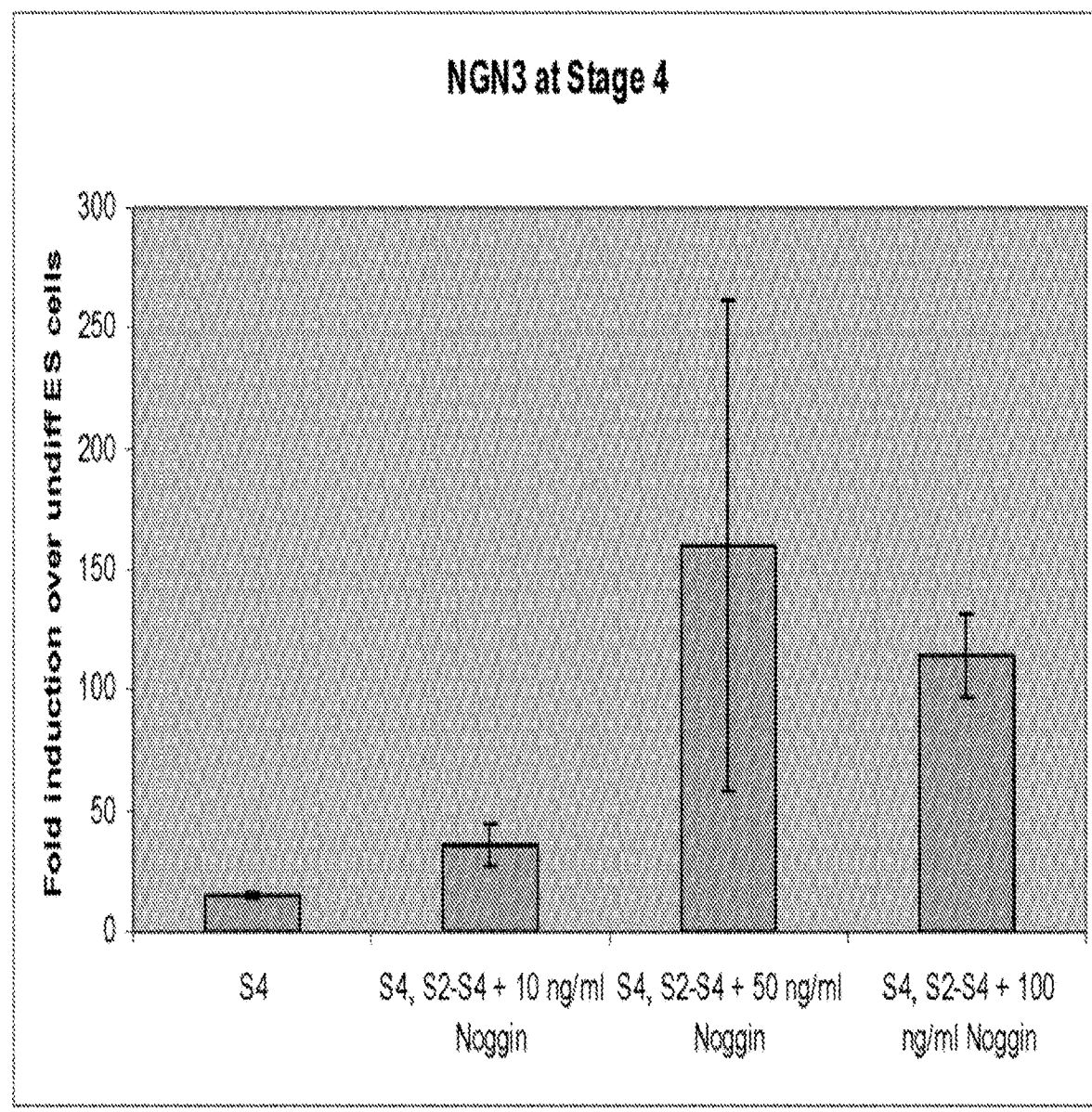
Figure 11A:
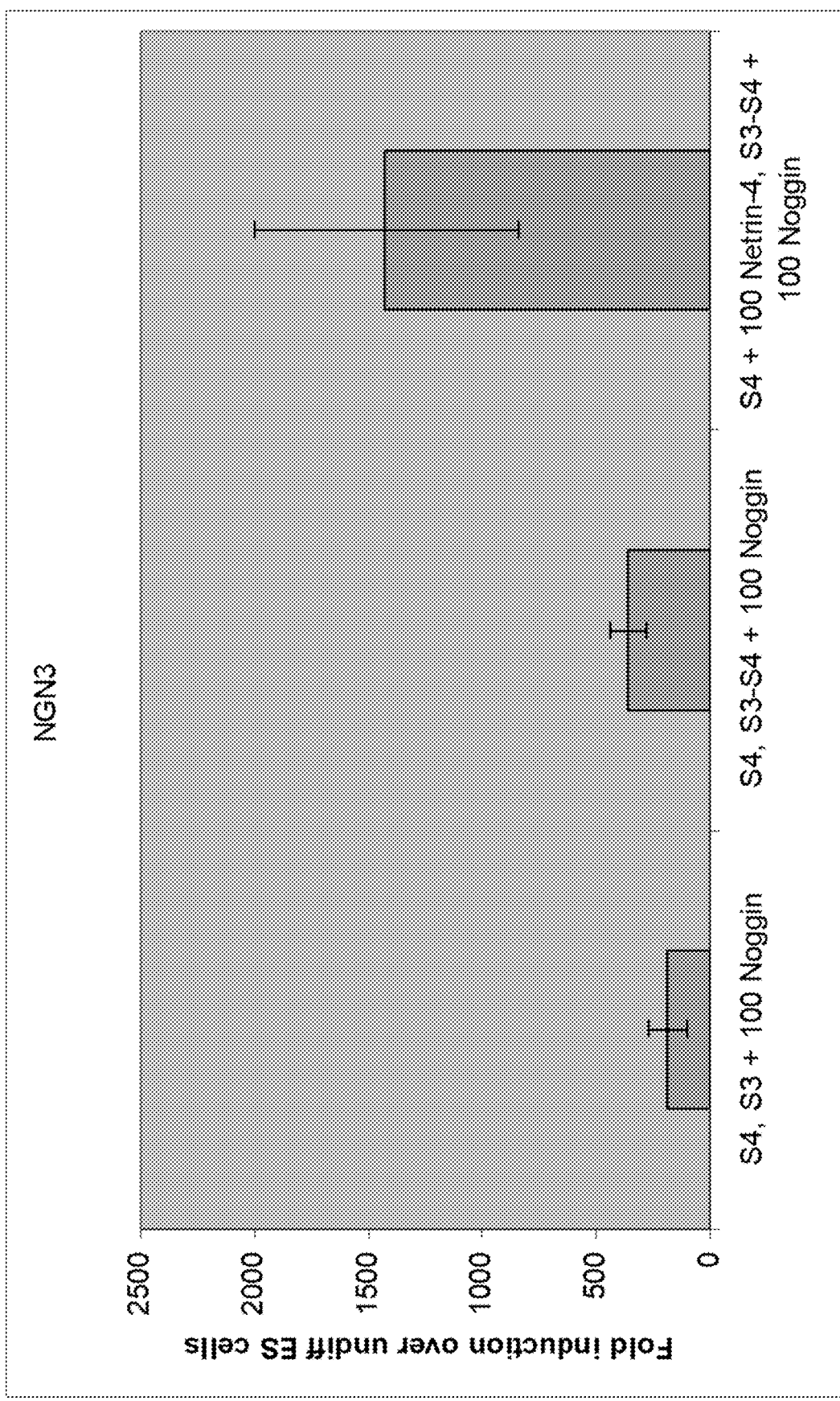
Figure 11B:
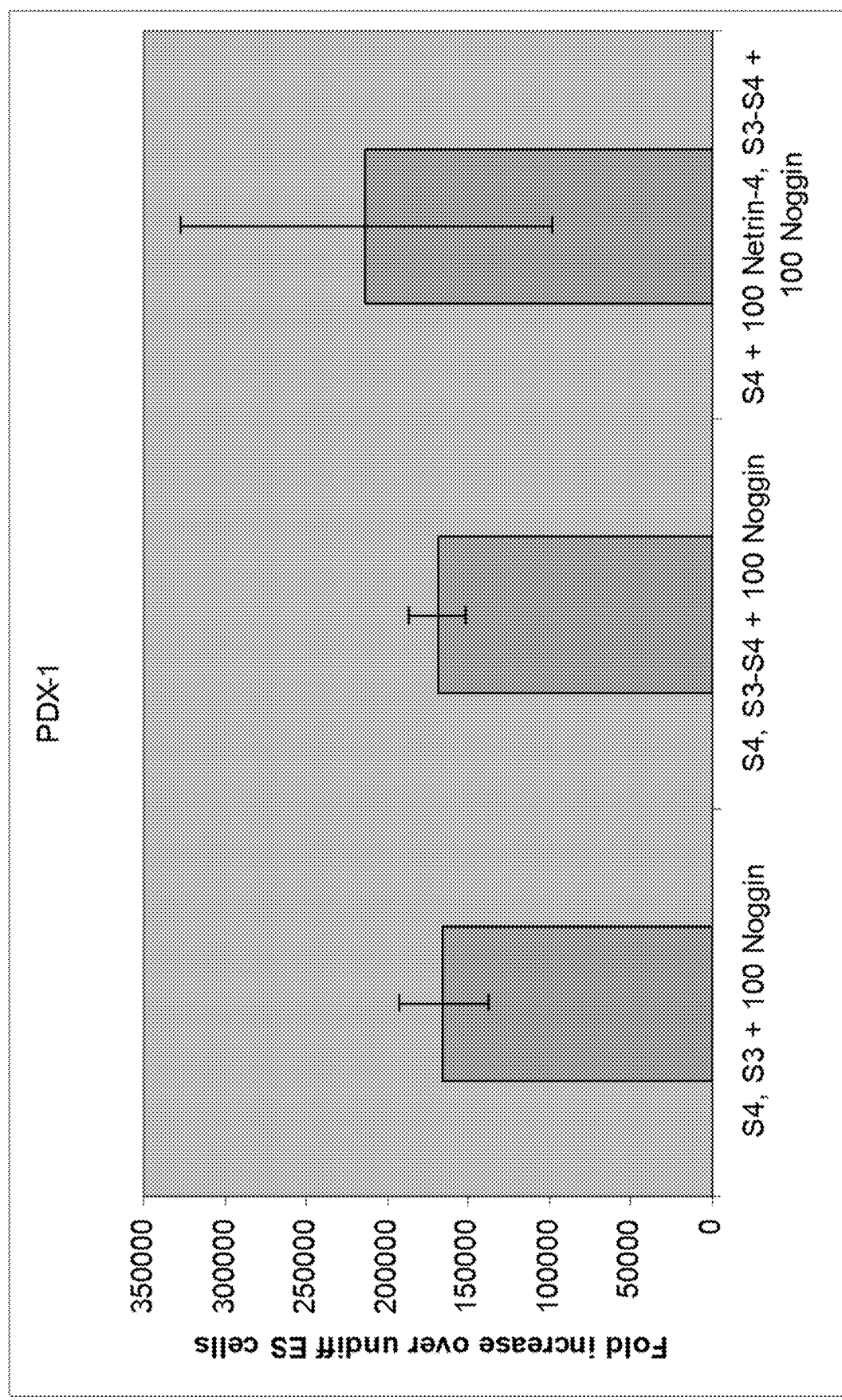
Figure 11C:
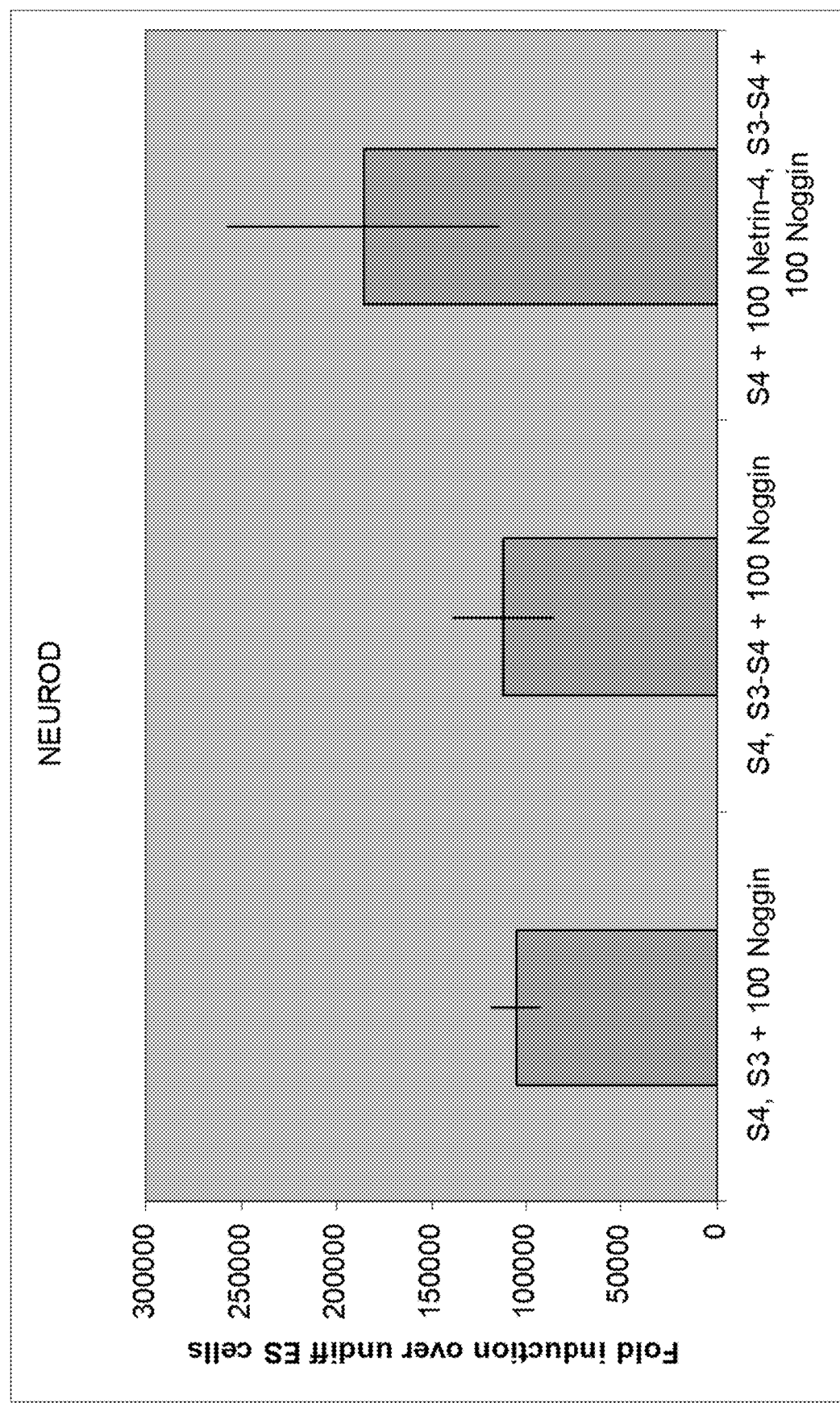
Figure 11D:
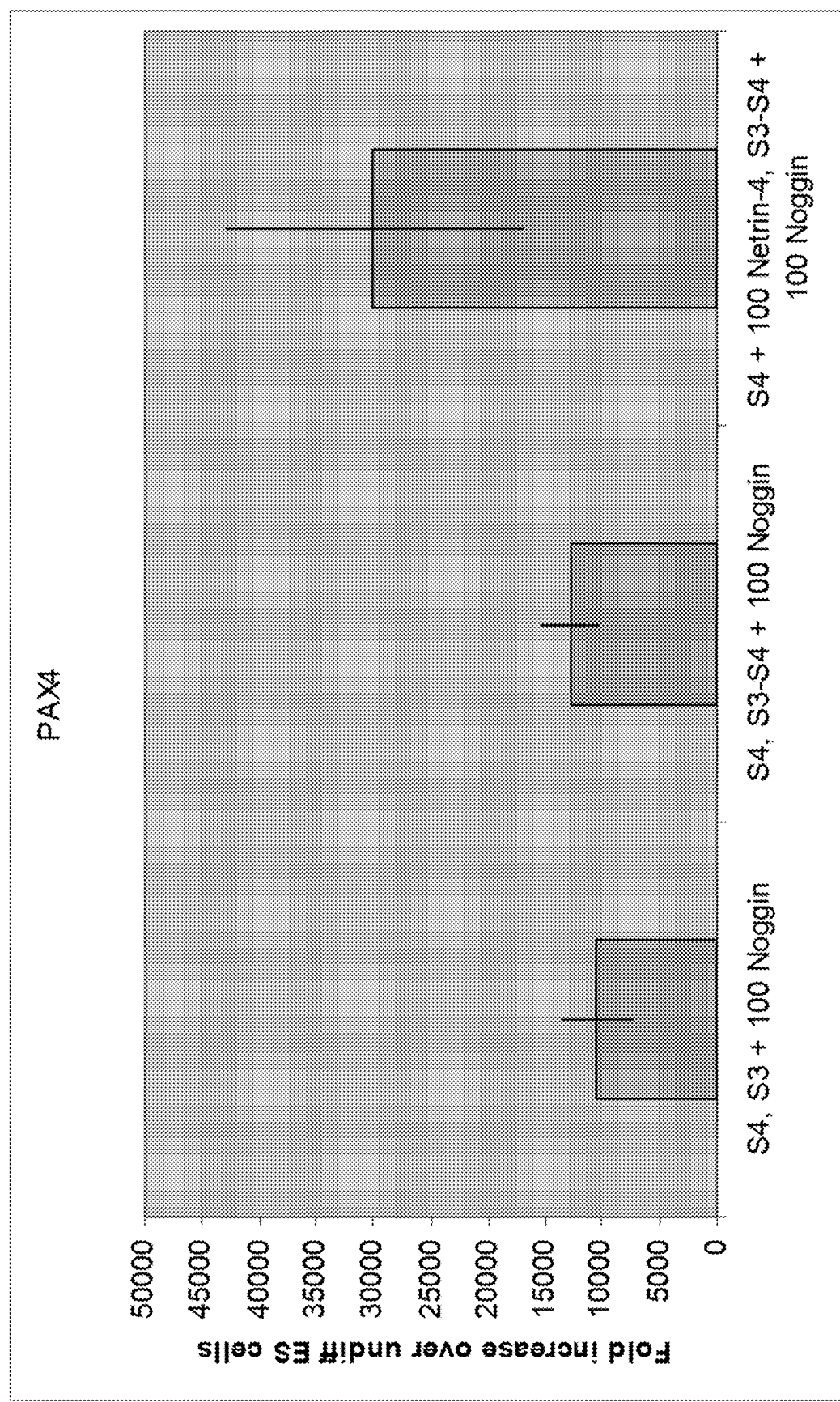
Figure 11E:
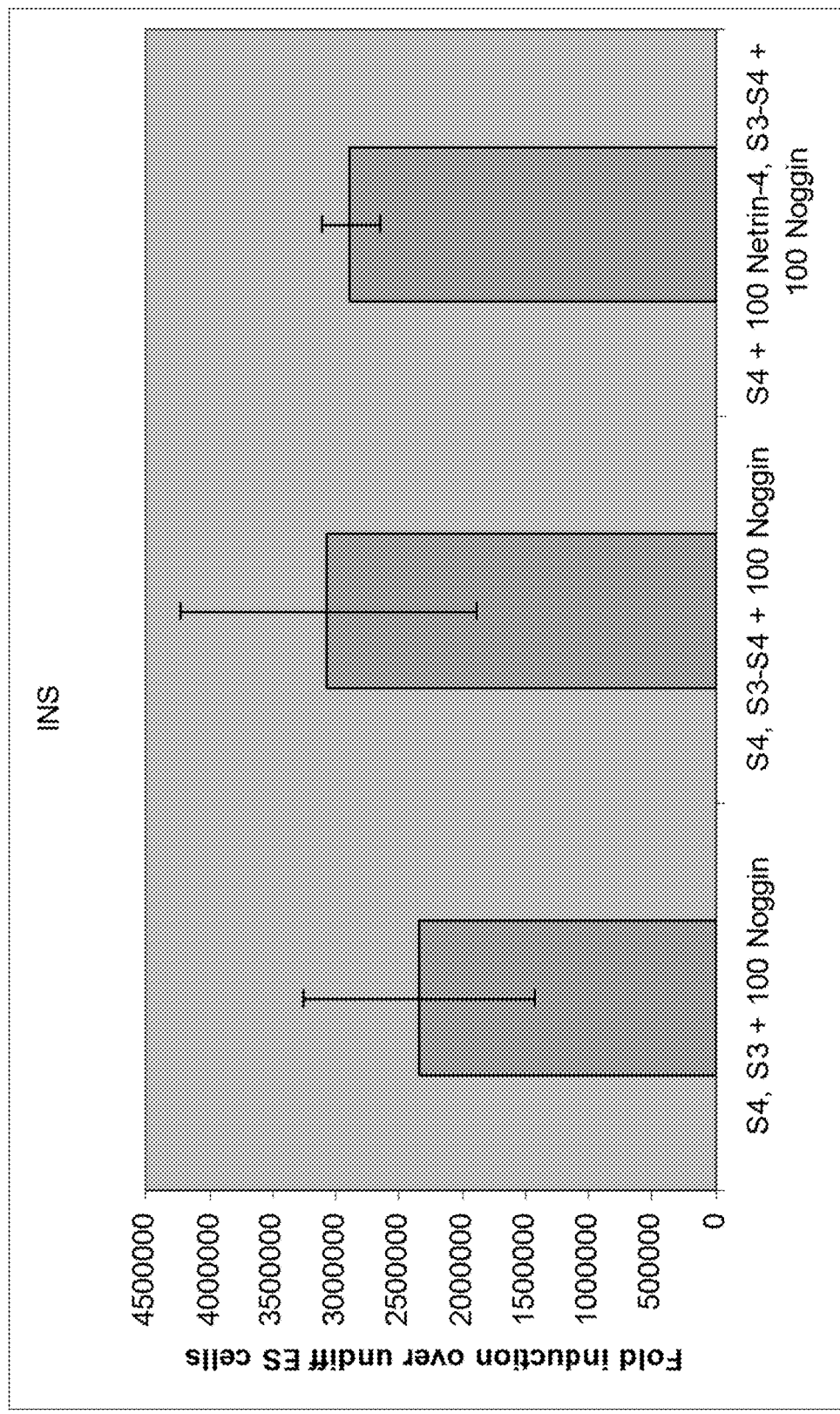
Figure 11F:
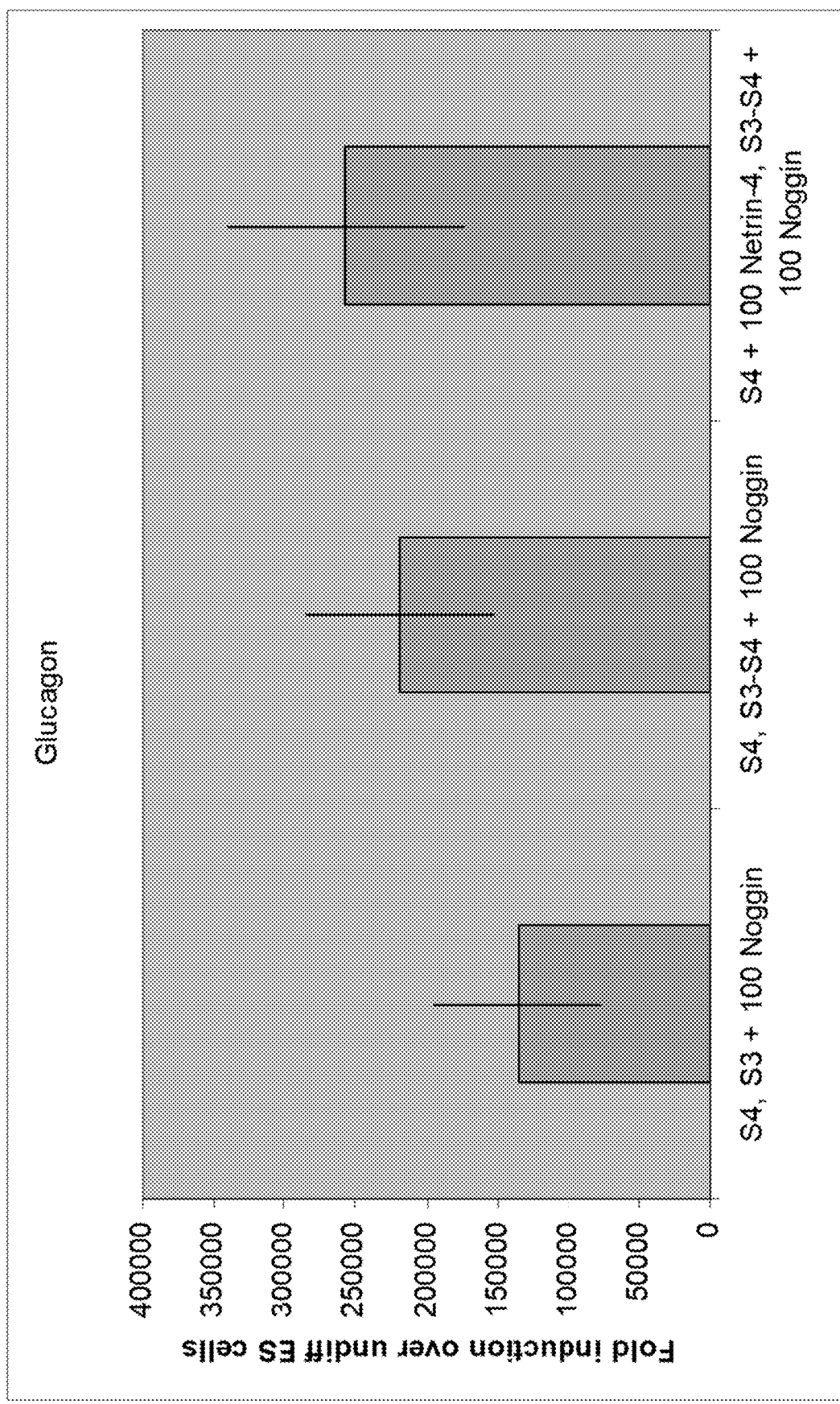

FIG. 10 shows real-time PCR analysis cells of the human embryonic stem cell line H1, differentiated according to the methods disclosed in Example 7.

FIGS. 11A-11F show real-time PCR analysis cells of the human embryonic stem cell line H1, differentiated according to the methods disclosed in Example 8. The data depicts the combined effects of Noggin added at stages 3 and 4, together with Netrin-4 and/or ALK 5 inhibitor added at stage 4 on the expression of FIG. 11A) ngn3, FIG. 11B) PDX-1, FIG. 11C) NeuroD, FIG. 11D) Pax4, FIG. 11E) insulin, and FIG. 11F) glucagon.

Figure 12A:
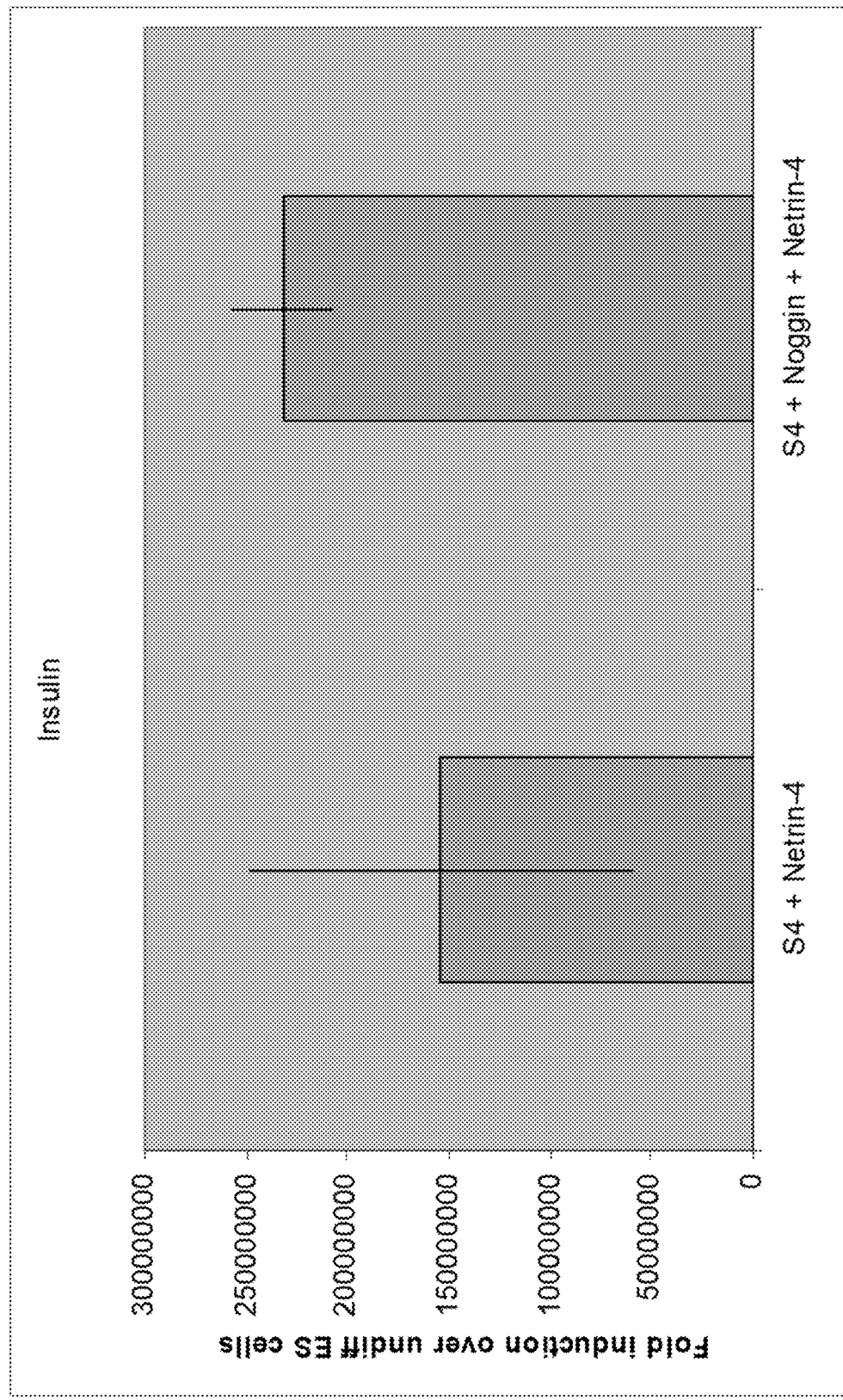
Figure 12B:
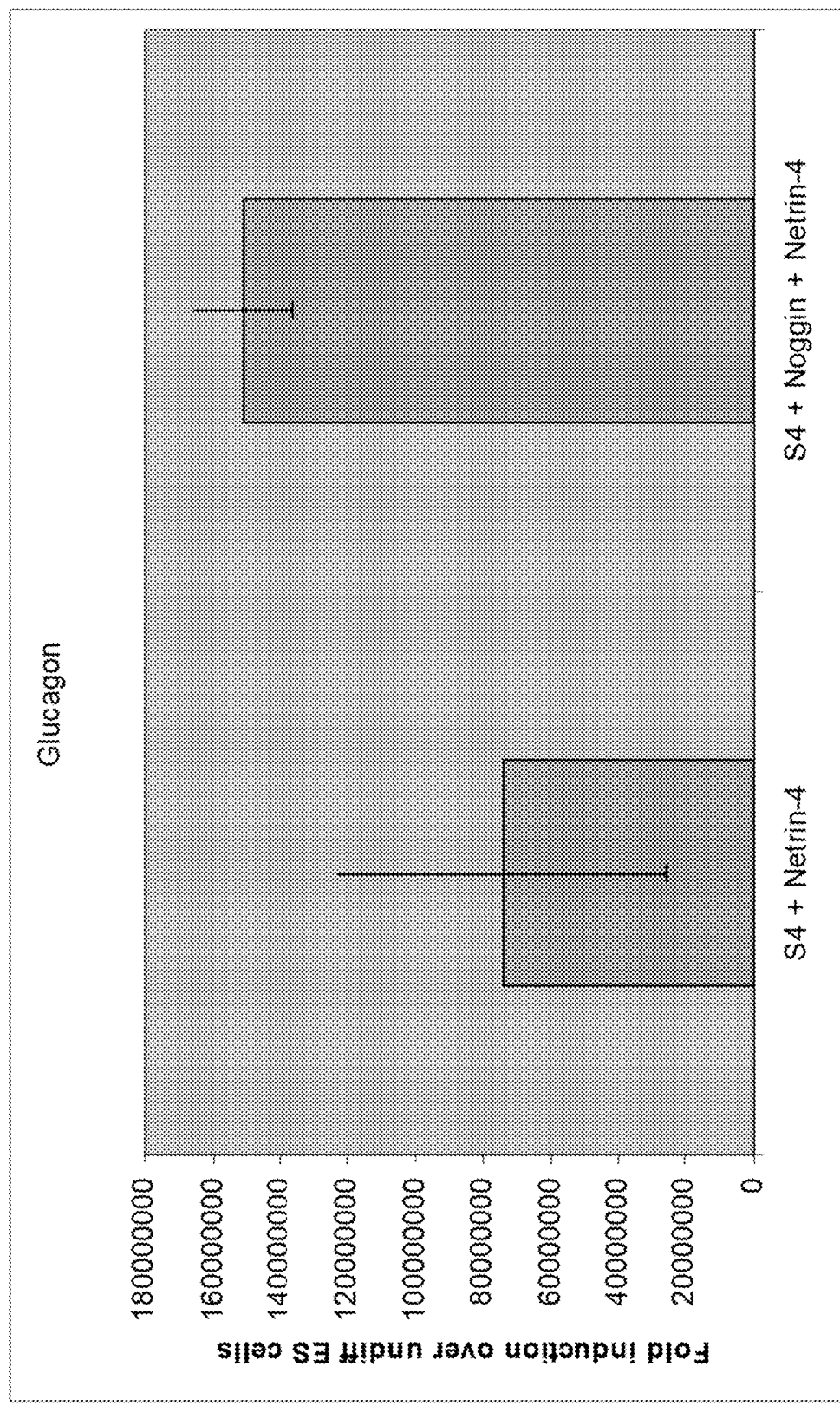
Figure 12C:
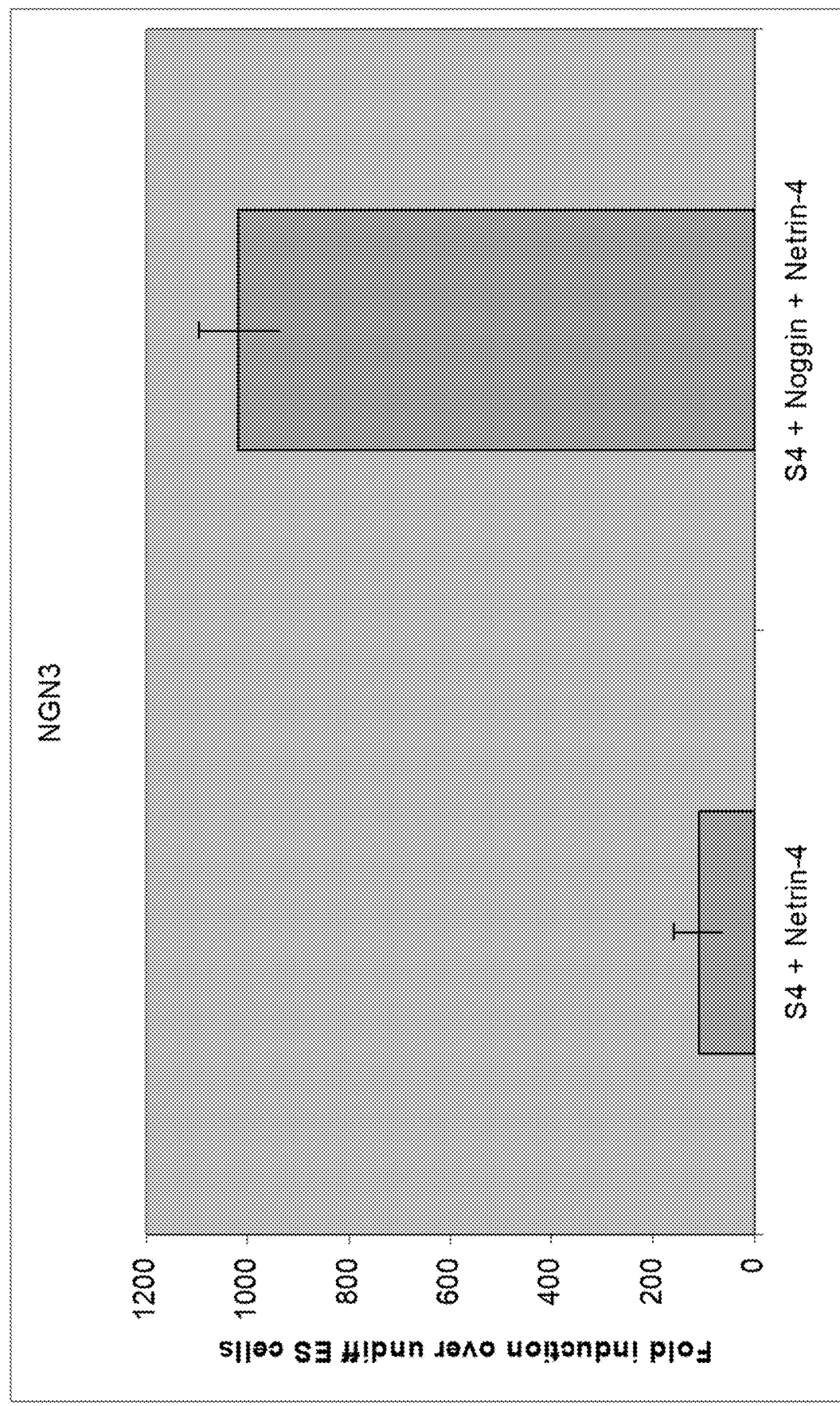
Figure 12D:
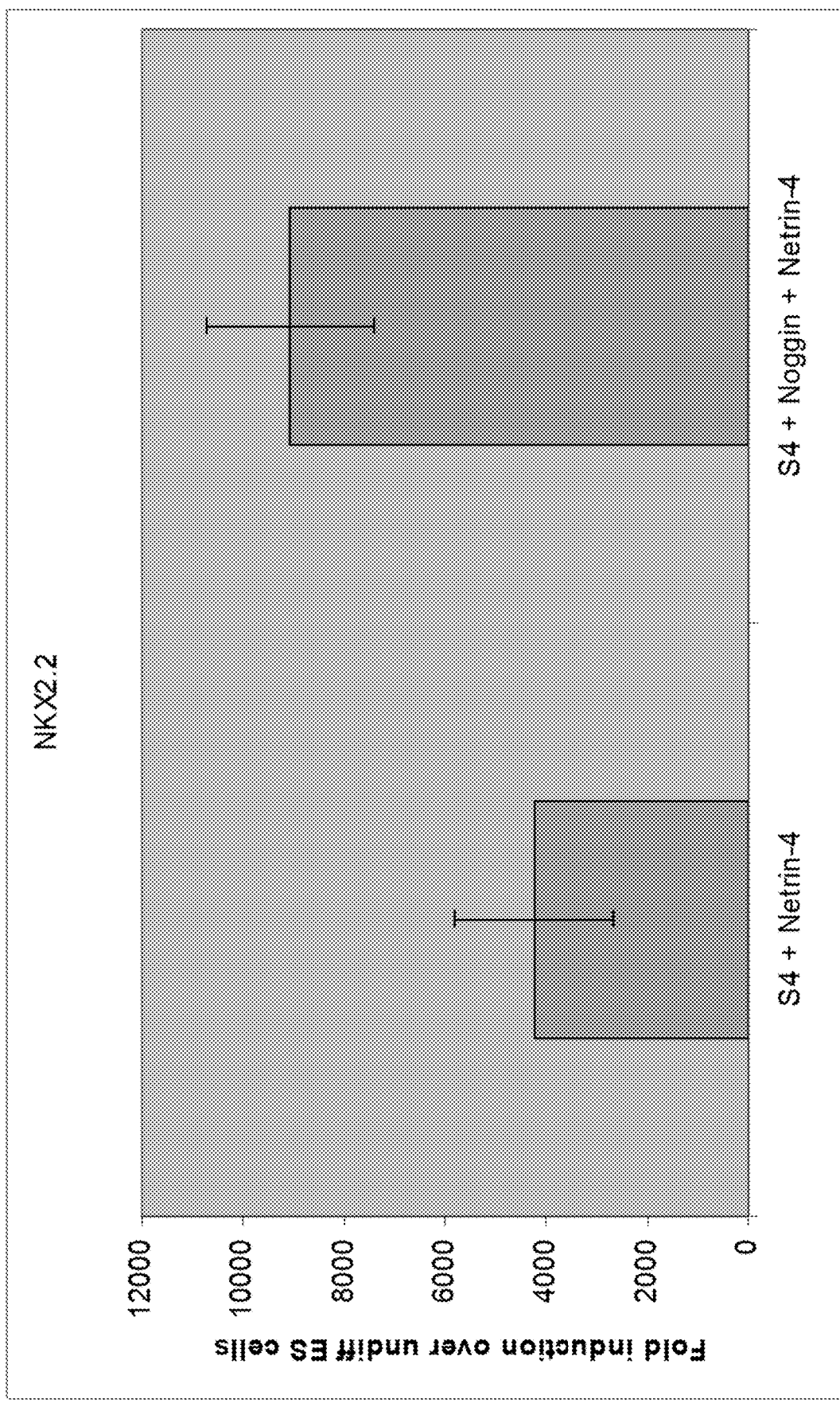
Figure 12E:
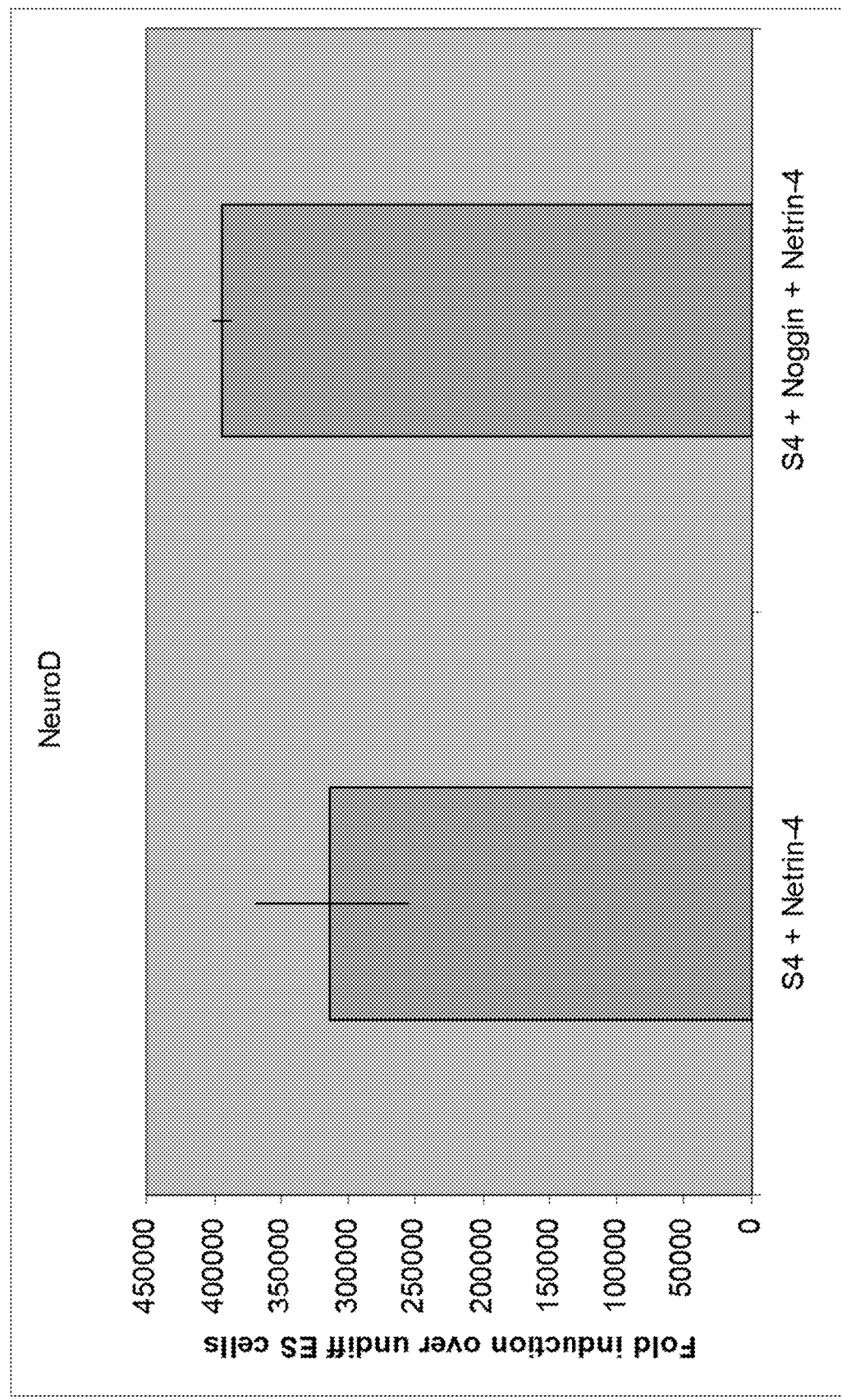
Figure 12F:
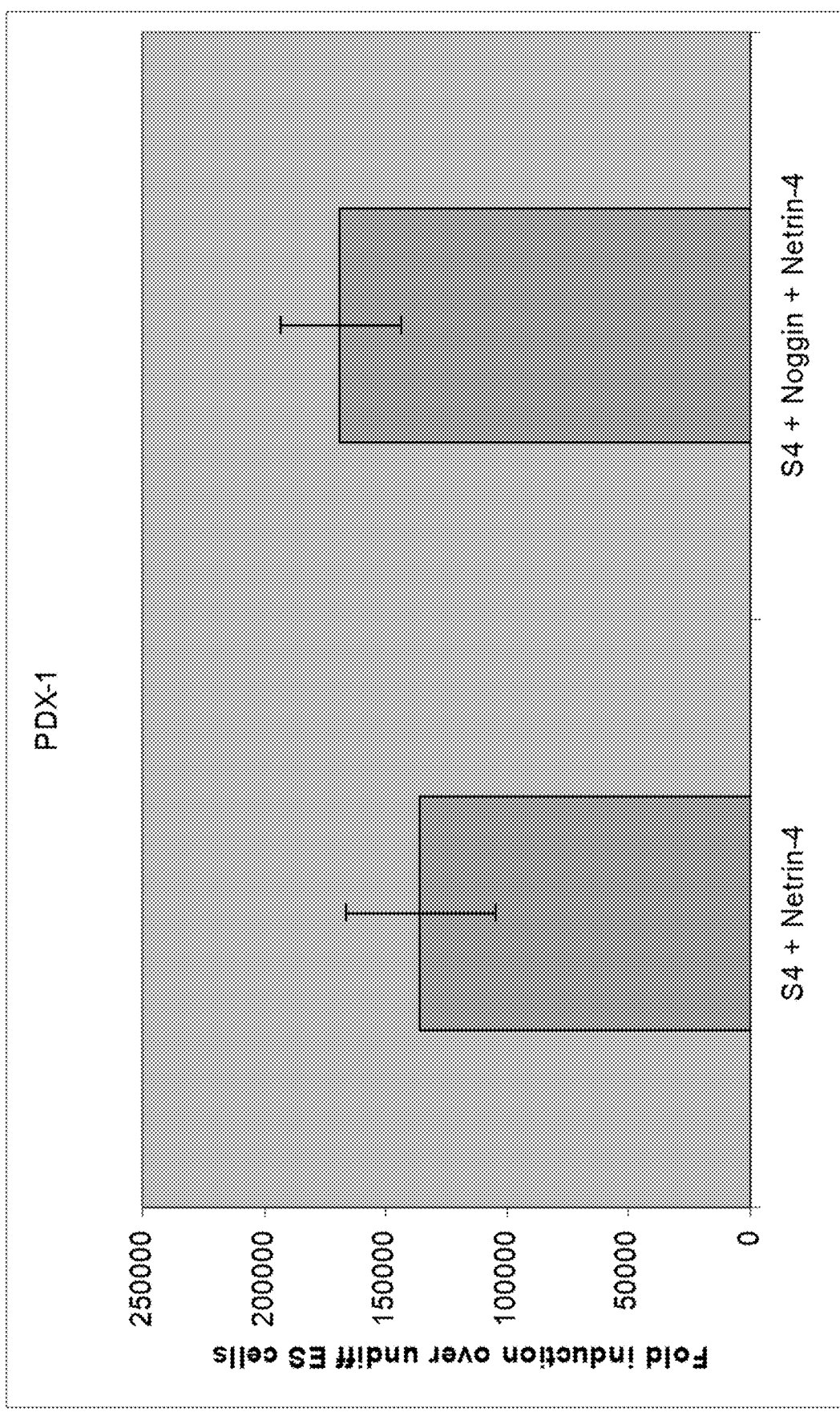

FIGS. 12A-12F show real-time PCR analysis cells of the human embryonic stem cell line H1, differentiated according to the methods disclosed in Example 8. FIG. 12A) insulin, FIG. 12B) glucagon, FIG. 12C) ngn3, FIG. 12D) NKX2.2, FIG. 12E) NeuroD, and FIG. 12F) PDX-1.

Figure 13A:
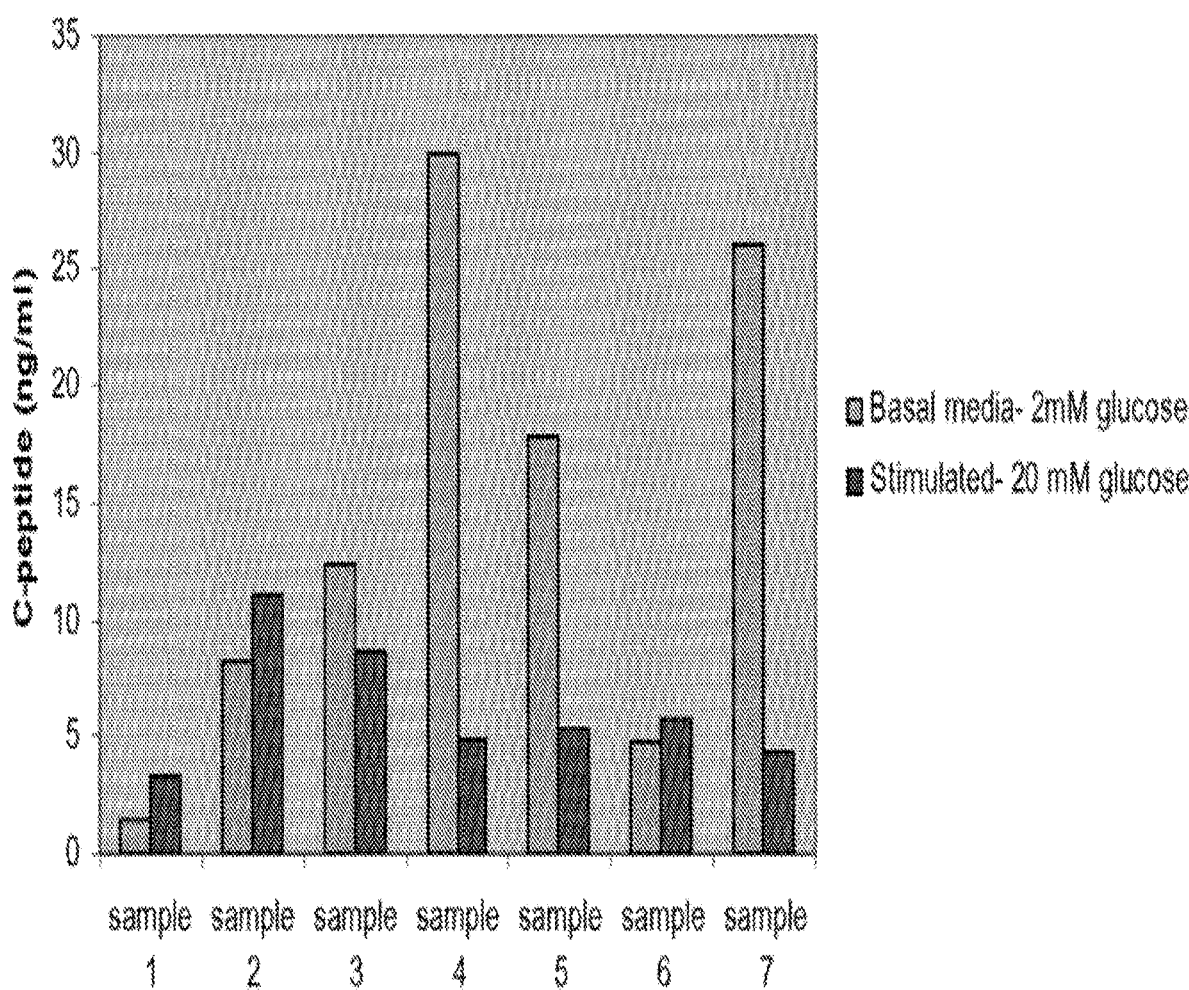
Figure 13B:
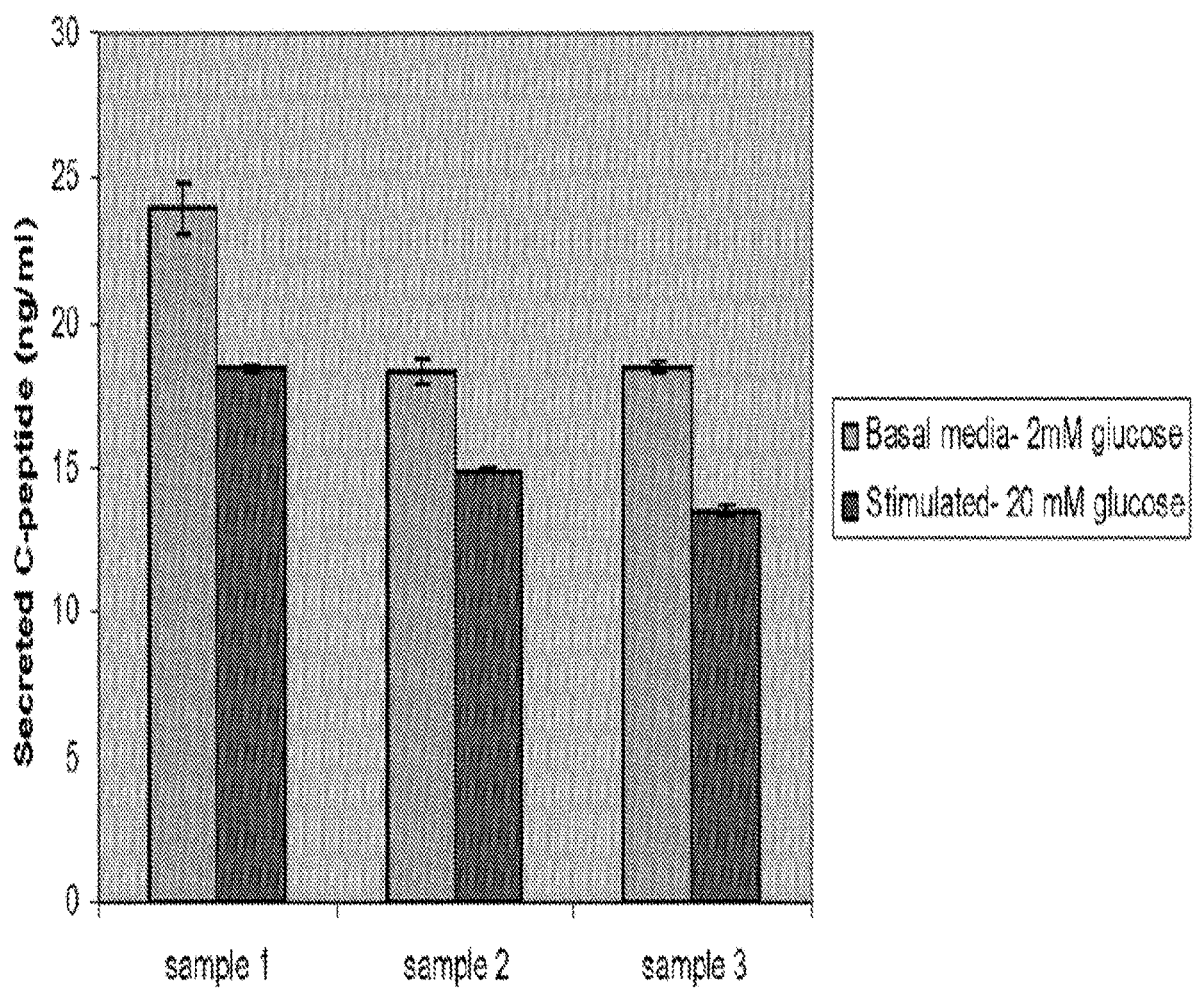
Figure 13C:
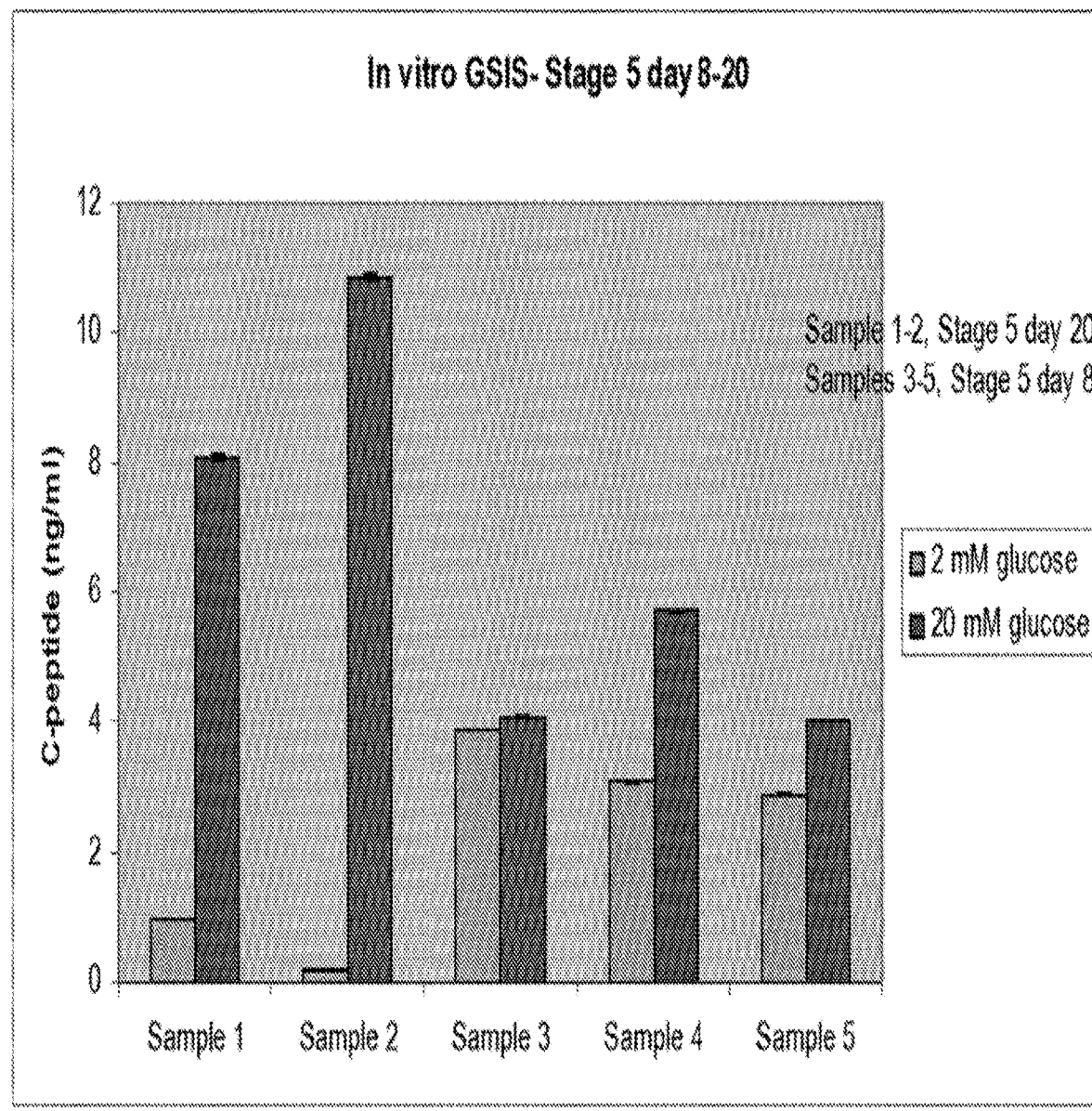

FIGS. 13A-13C show the in vitro Glucose Stimulated Insulin Secretion (GSIS) of extended stage 5 cultures. Stage 5 cells prepared according to the methods disclosed in Example 9 were glucose challenged at days FIG. 13A) 6, FIG. 13B)12, and FIG. 13C) 8-20 days in culture at stage 5.

Figure 14:
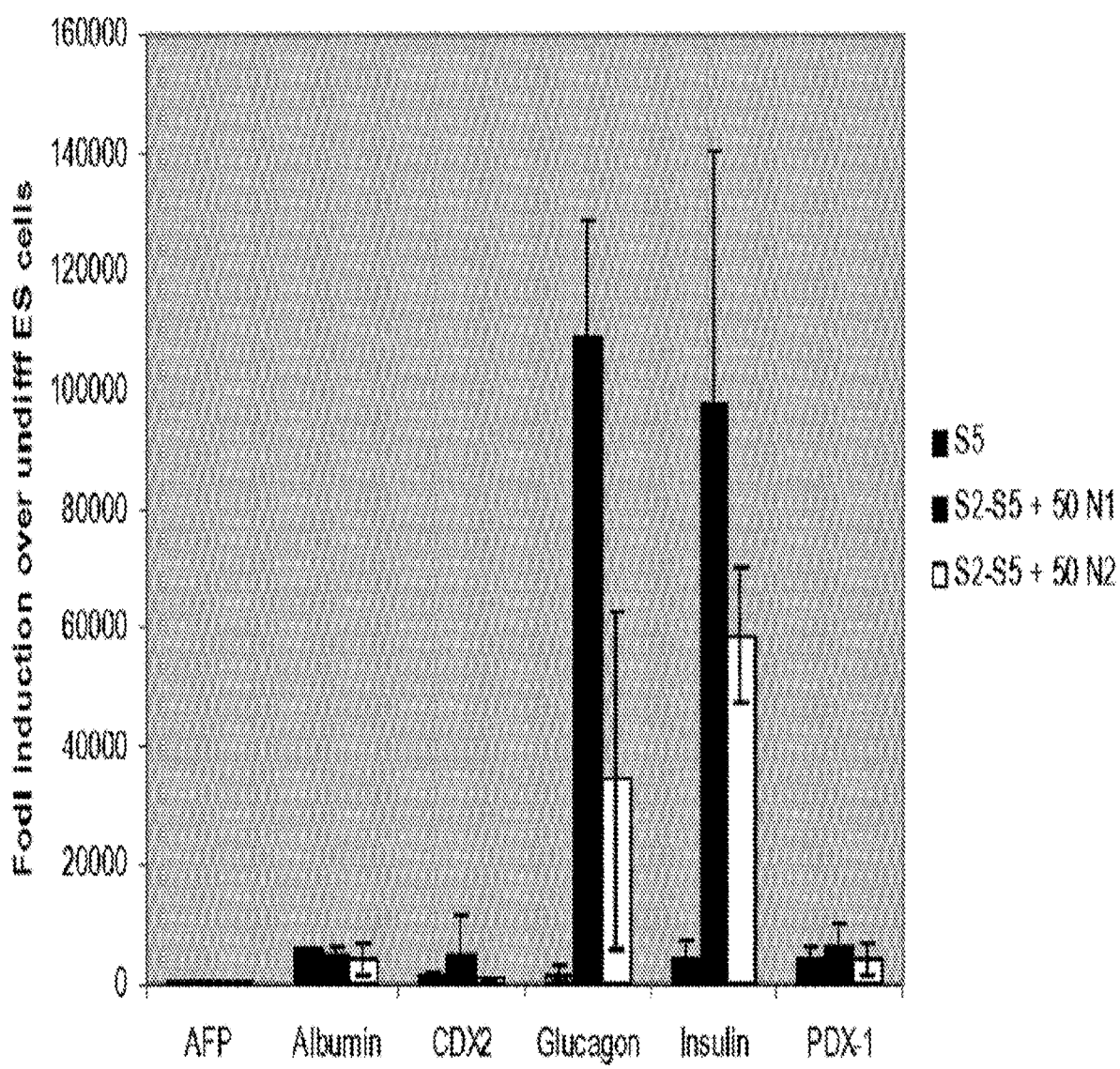

FIG. 14 shows the effect of Netrin-1 or Netrin-2 on expression of endocrine markers. Real-time PCR analysis cells of the human embryonic stem cell line H1, differentiated according to the methods disclosed in Example 10.

Figure 15A:
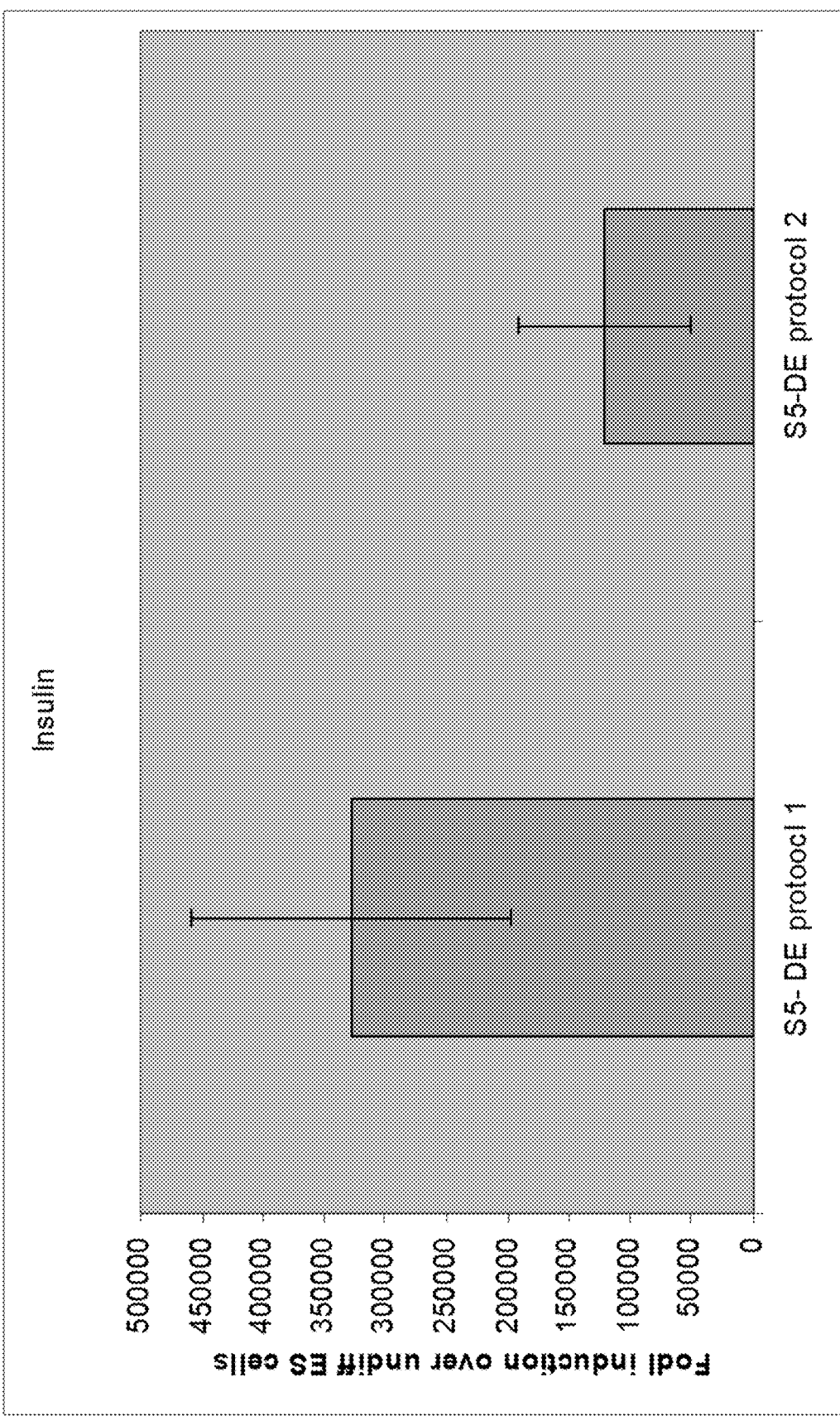
Figure 15B:
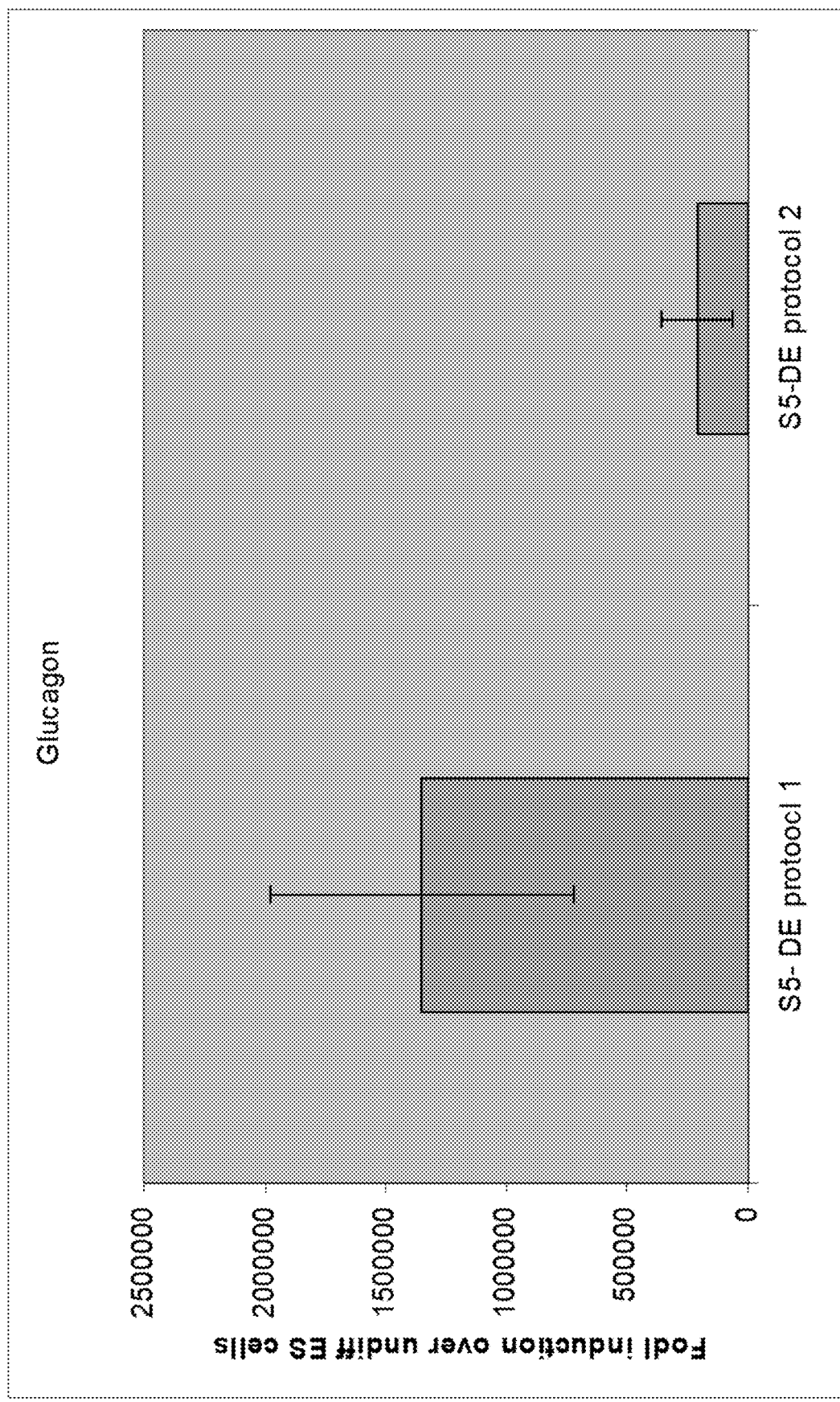
Figure 15D:
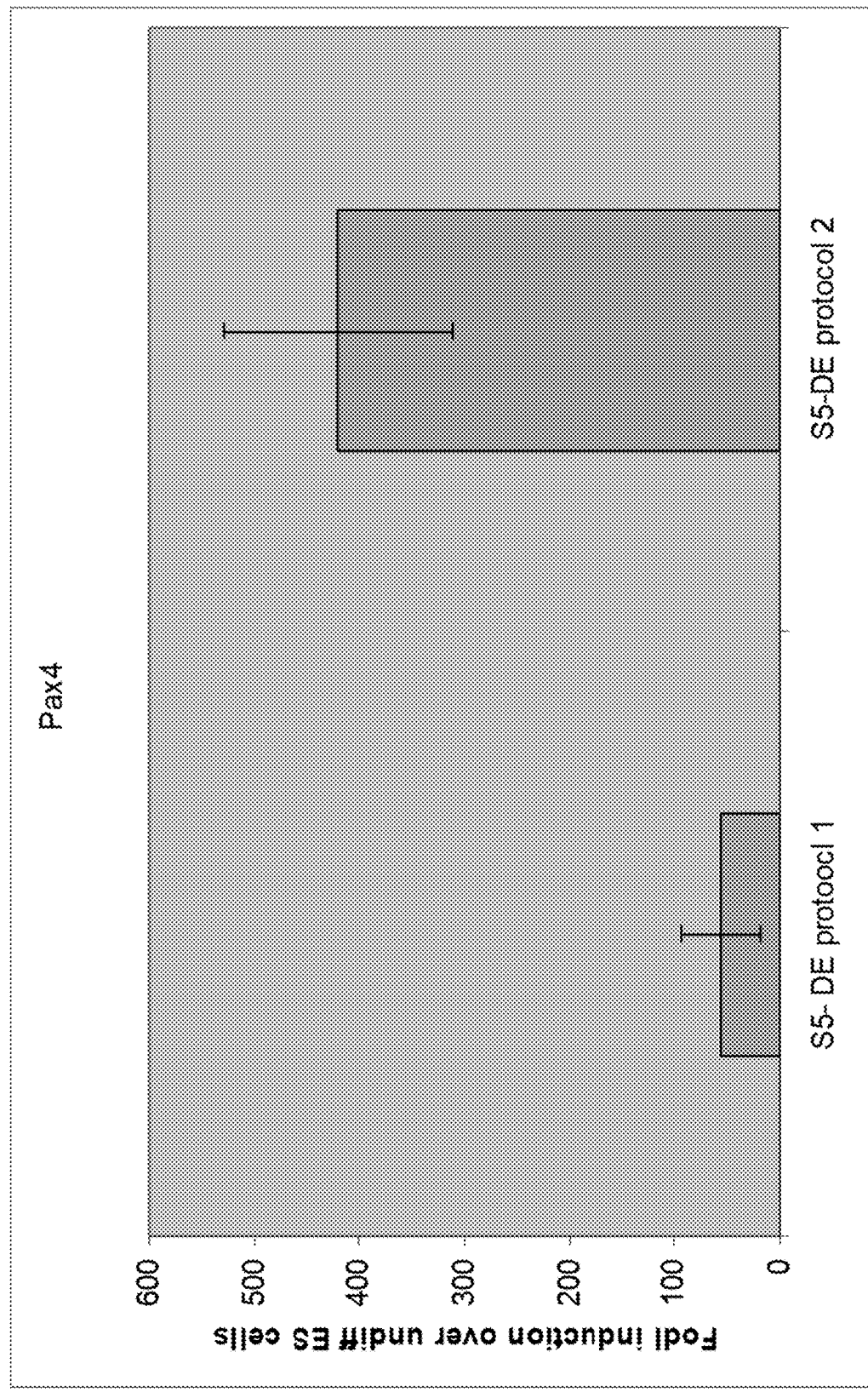
Figure 15E:
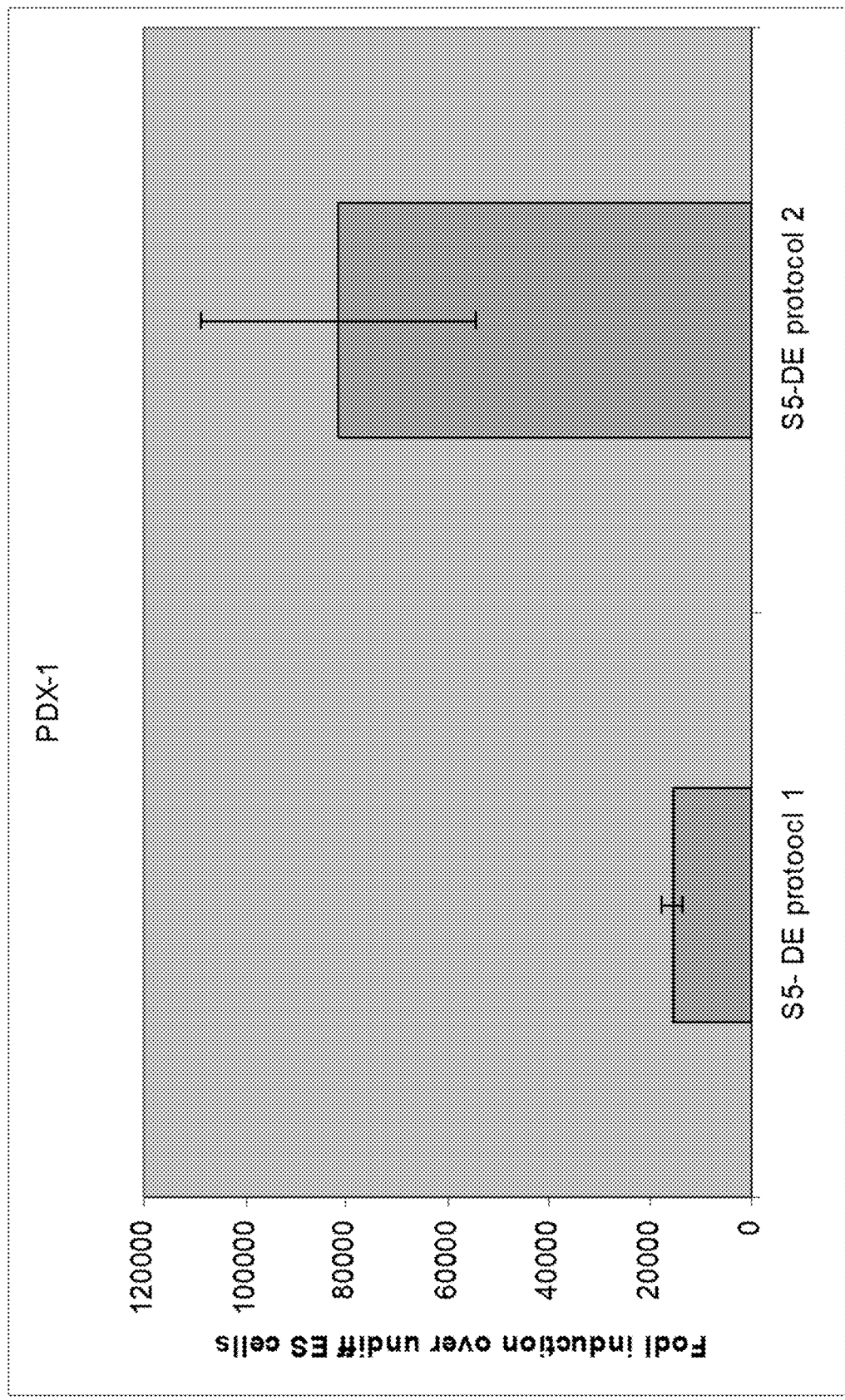
Figure 15F:
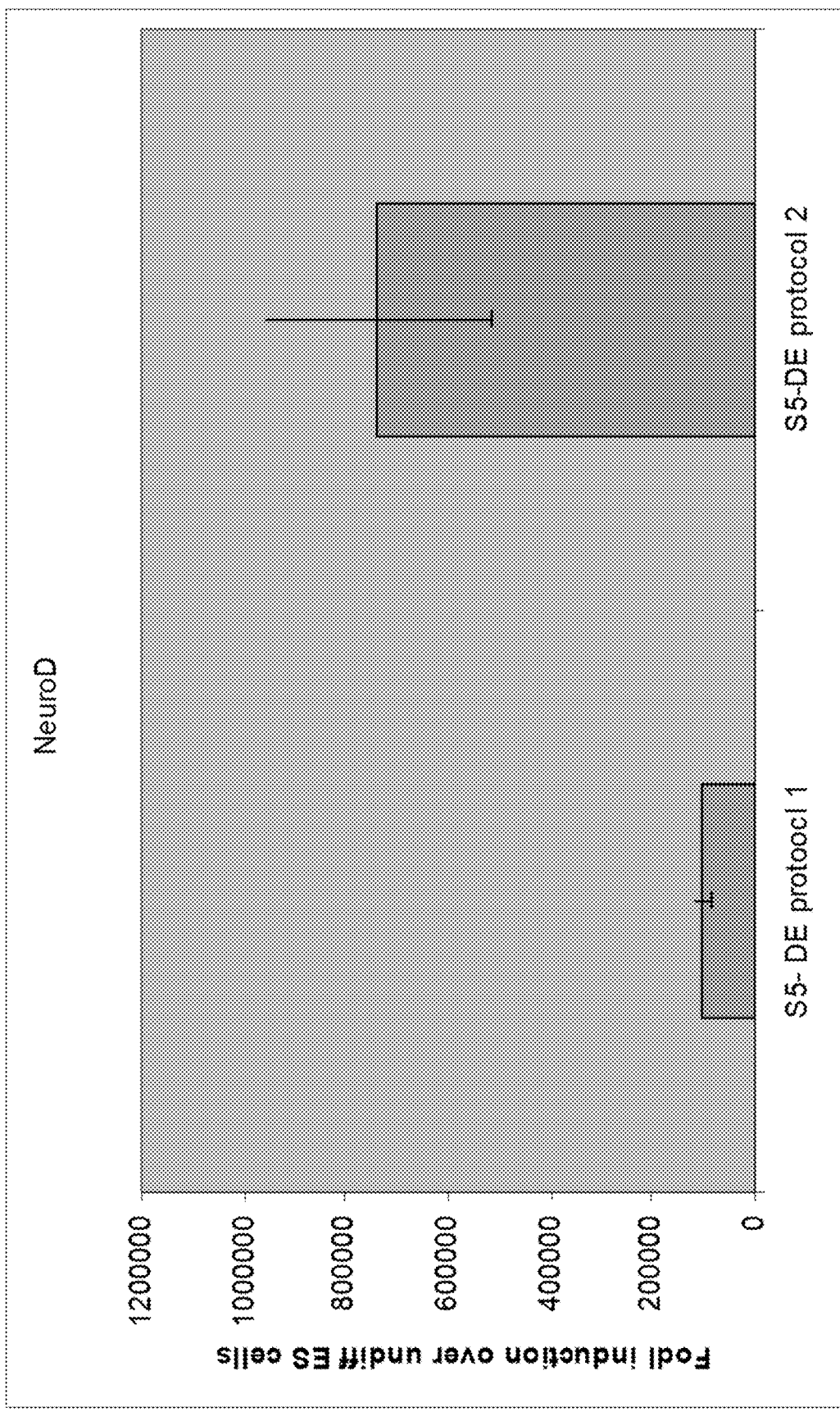

FIGS. 15A-15F show the induction of endocrine markers using an alternative method to induce definitive endoderm. Real-time PCR analysis cells of the human embryonic stem cell line H1, differentiated according to the methods disclosed in Example 11. FIG. 15A) insulin, FIG. 15B) glucagon, FIG. 15C) NKX2.2, FIG. 15D) Pax4, FIG. 15E) PDX-1, and FIG. 15F) NeuroD.

Figure 1B:
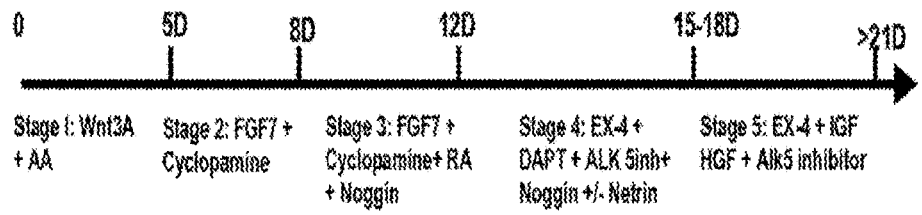
Figure 1C:
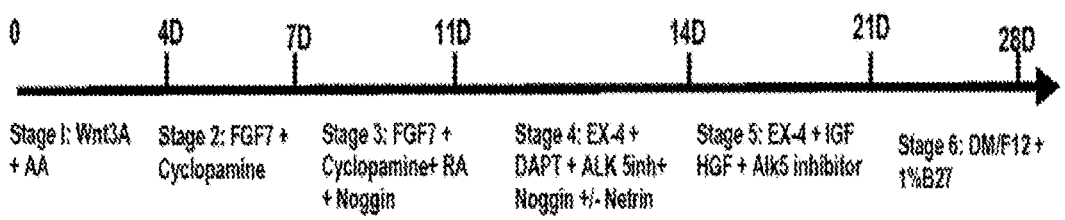
Figure 16A:
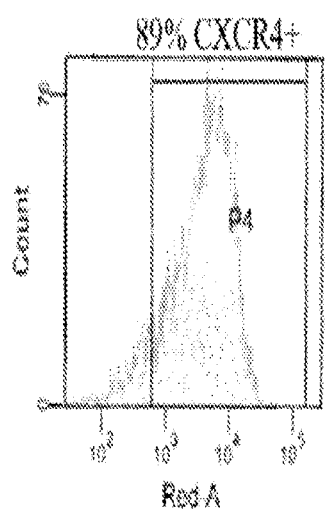
Figure 16B:
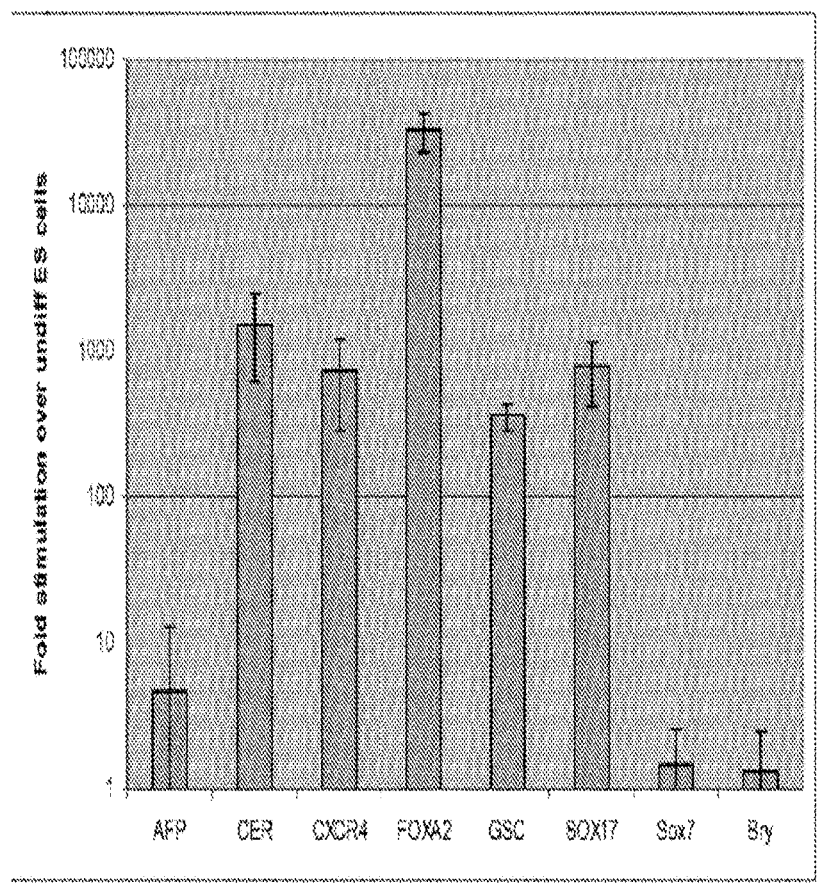
Figure 16I:
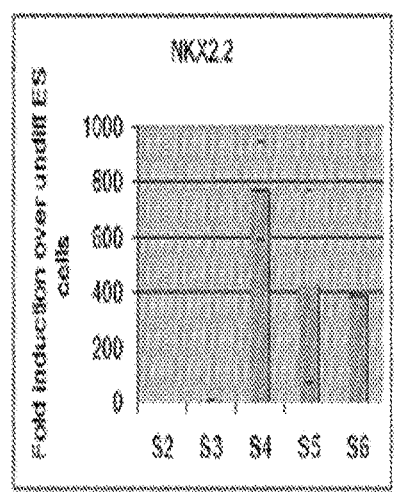
Figure 16J:
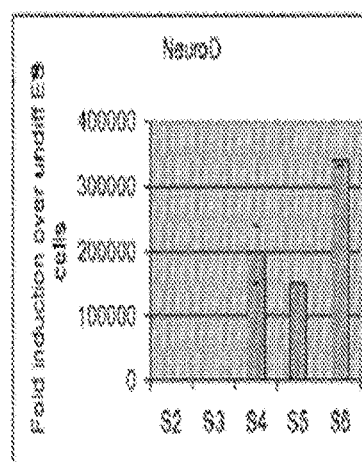
Figure 16K:
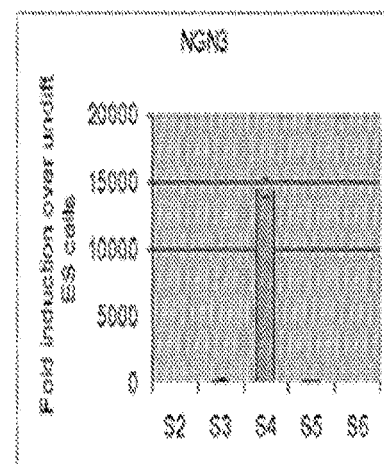
Figure 16L:
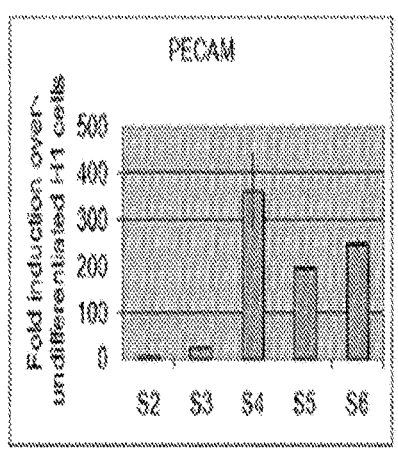
Figure 16M:
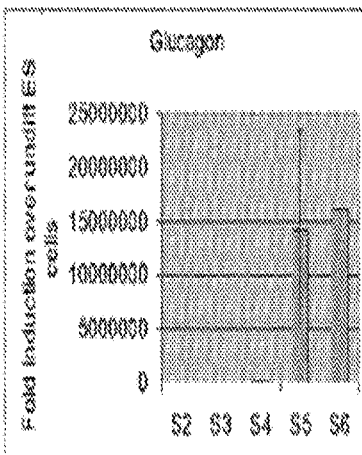
Figure 16N:
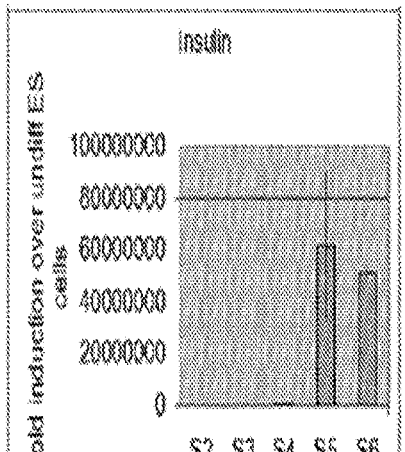

FIGS. 16A-16N show the expression of various markers at the various stages of the differentiation protocol outlined in FIG. 1C. FIG. 16A): shows the expression of CXCR4, as determined by FACS in H1 cells at day three of stage 1. FIG. 16B) shows the expression of markers characteristic of the definitive endoderm lineage and the extra-embryonic lineage, in cells at day three of stage 1, as determined by real-time PCR. FIGS. 16C-16N) show the expression of various genes in cells harvested at the end of stages 2-6, as determined by real-time PCR.

Figure 17:
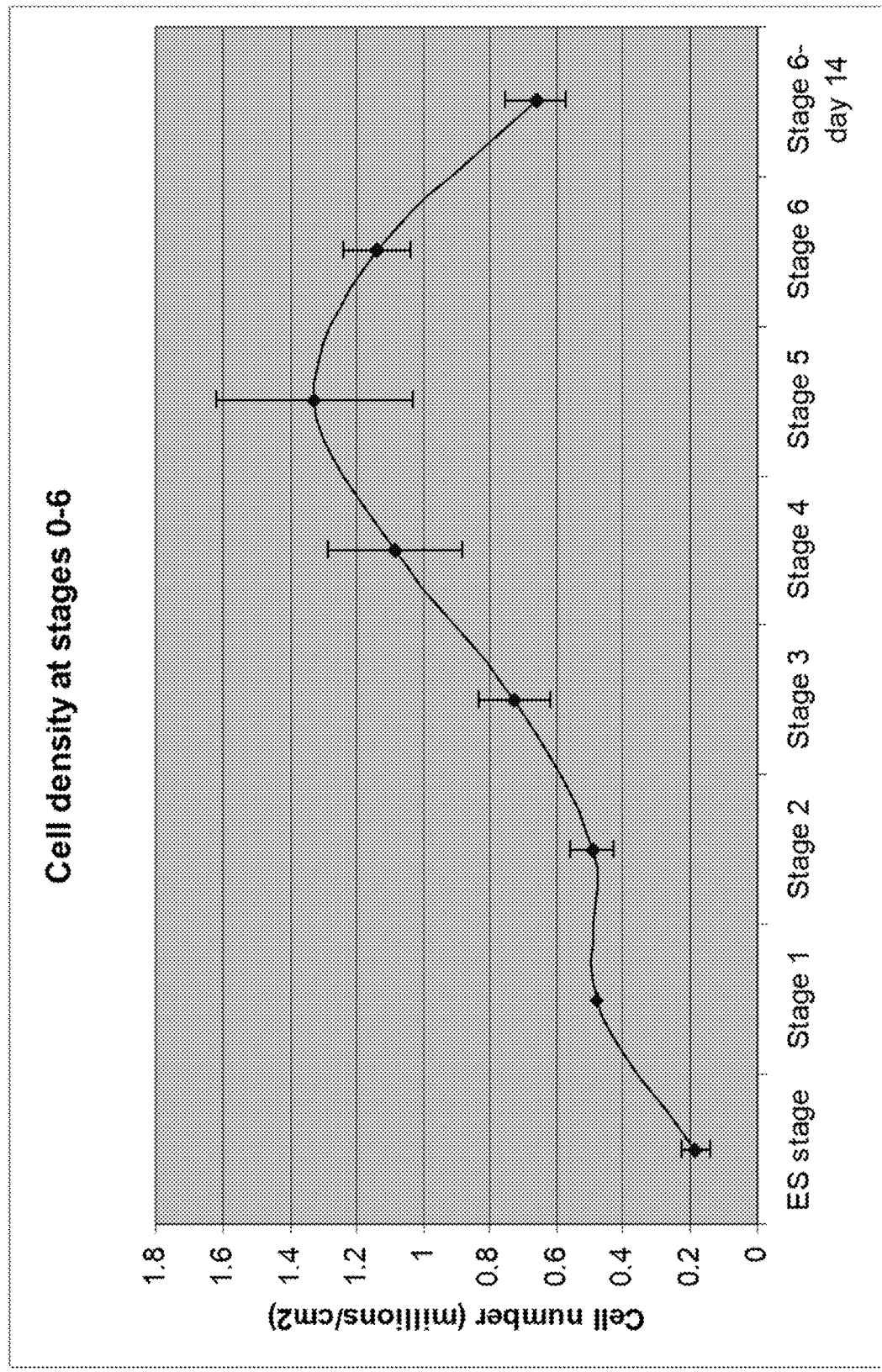

FIG. 17 shows the number of cells at the various stages of the differentiation protocol outlined in FIG. 1C.

Figure 18:
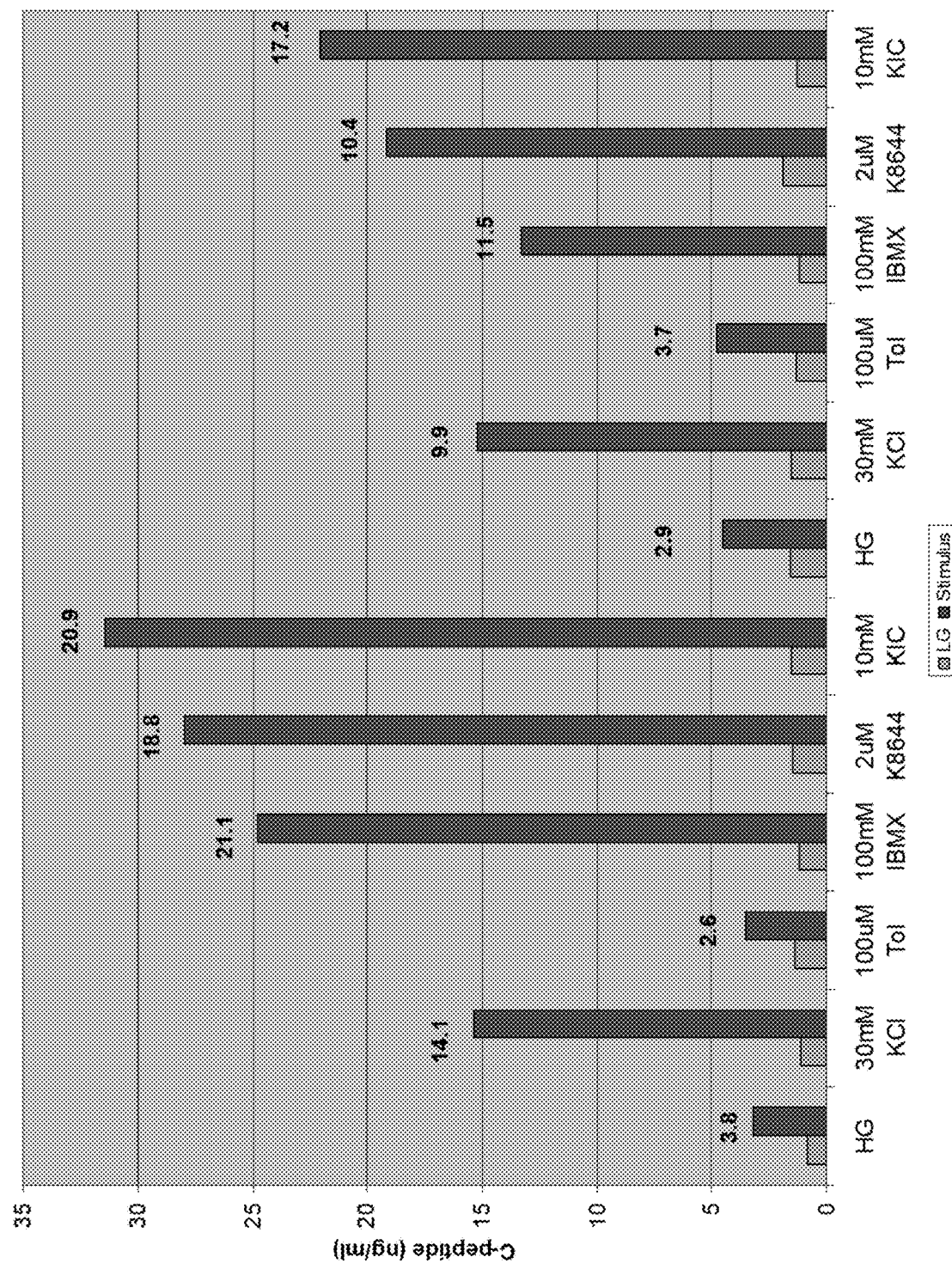

FIG. 18 shows C-peptide release from cells at the end of stage 6 of the differentiation protocol outlined in FIG. 1C in response to various stimuli.

Figure 19:
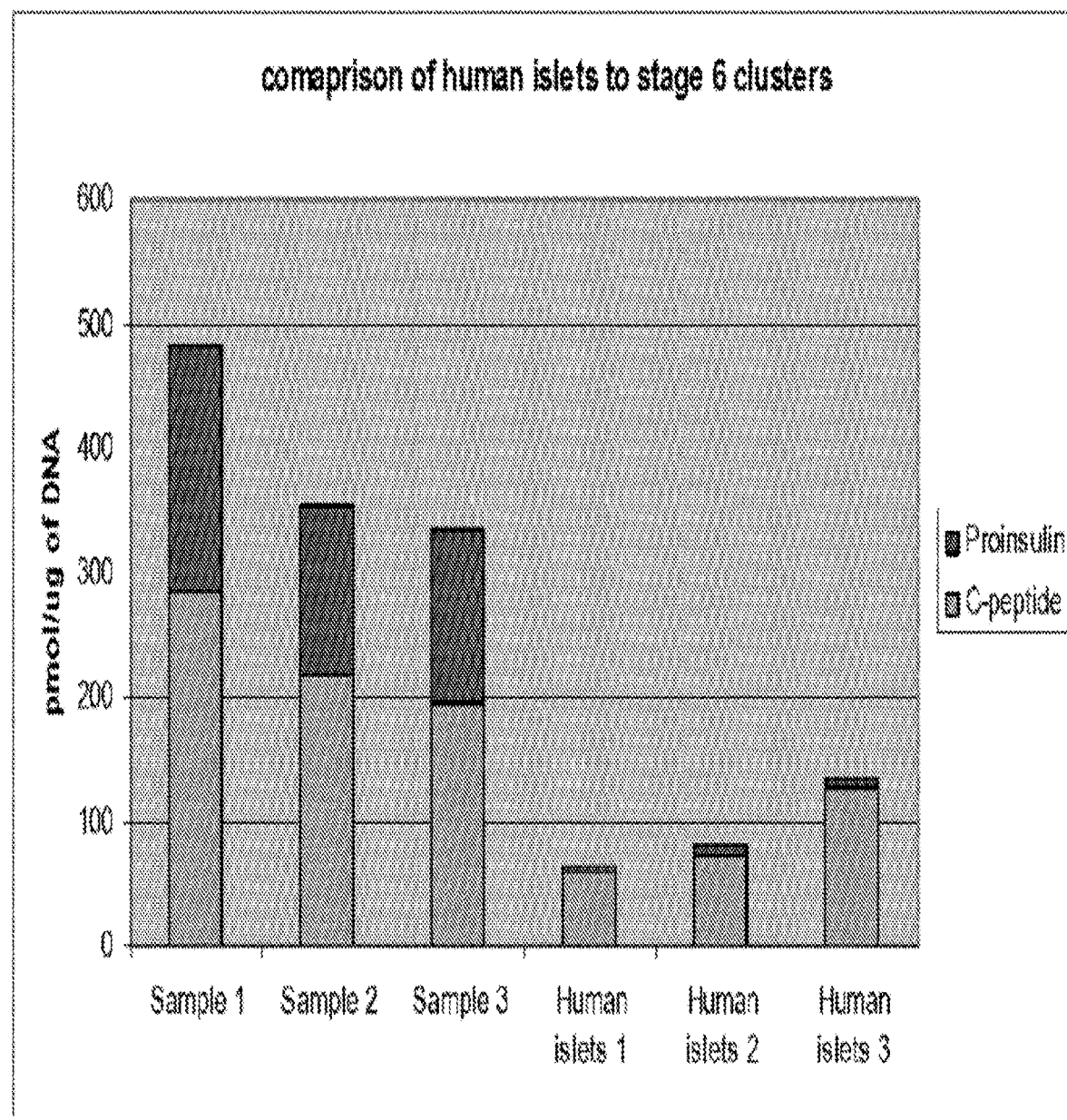
Figure 21A:
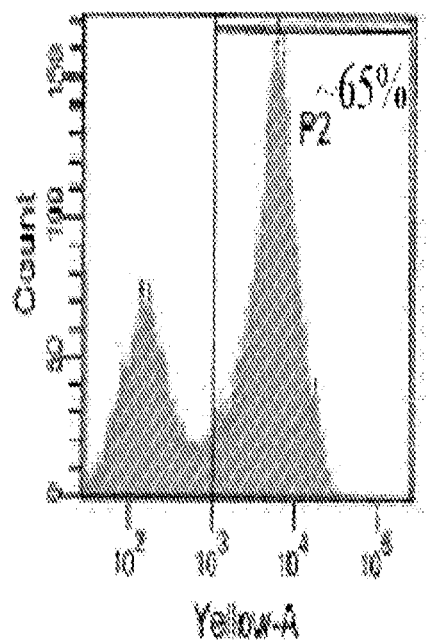
Figure 21B:
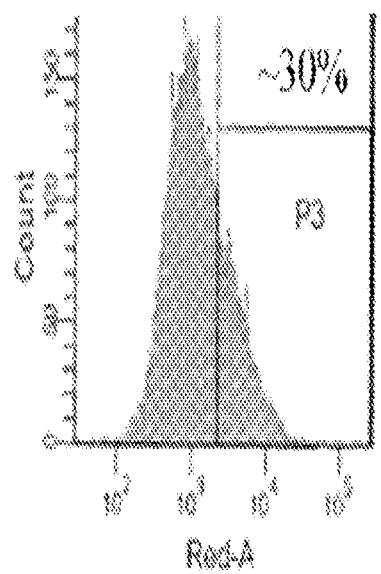
Figure 21C:
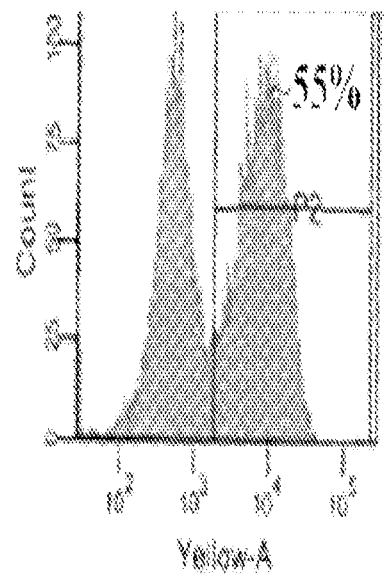
Figure 21D:
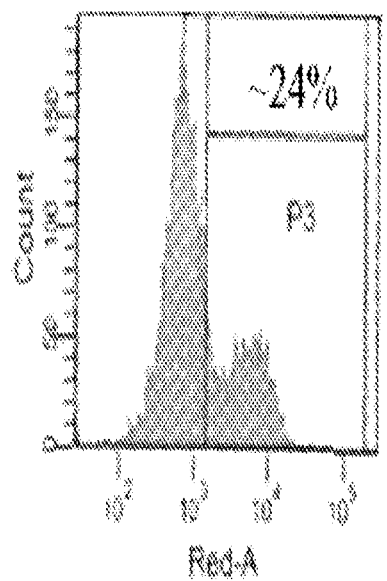
Figure 22A:
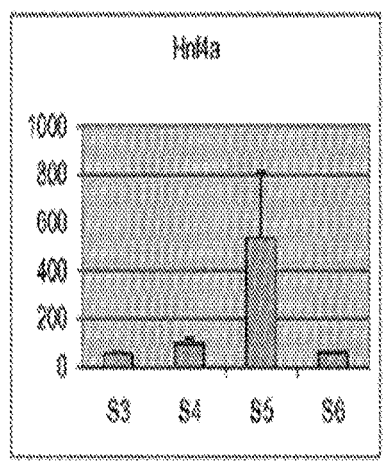
Figure 22B:
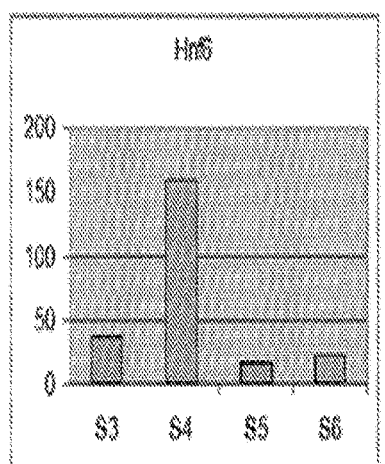
Figure 22C:
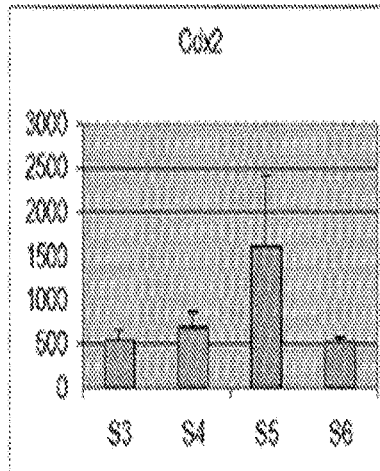
Figure 22D:
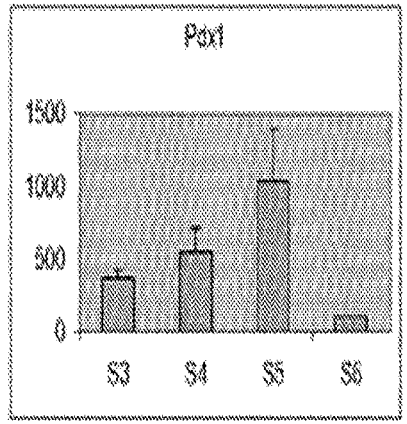
Figure 22E:
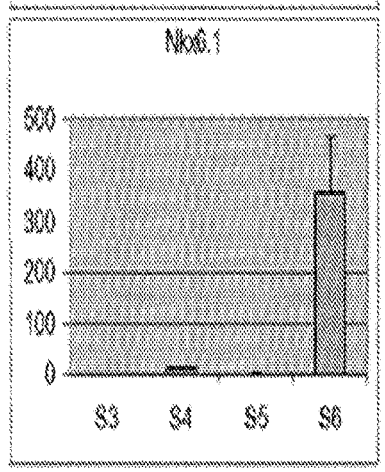
Figure 22F:
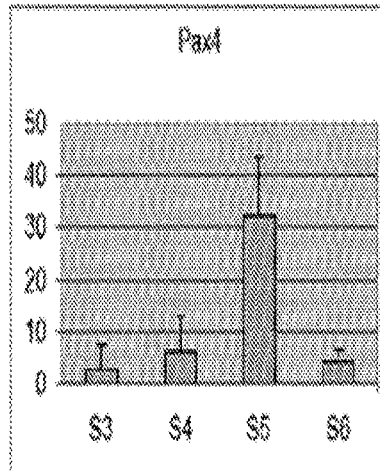
Figure 22G:
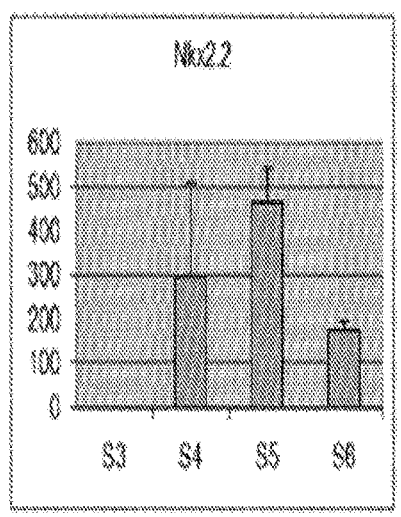
Figure 22H:
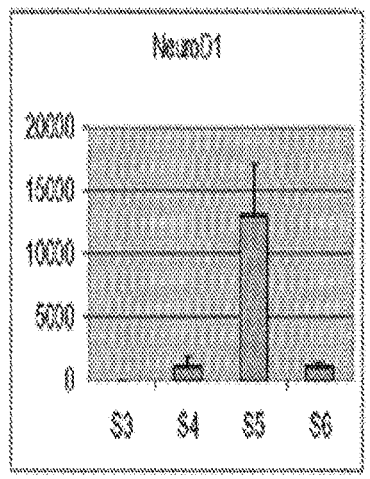
Figure 22I:
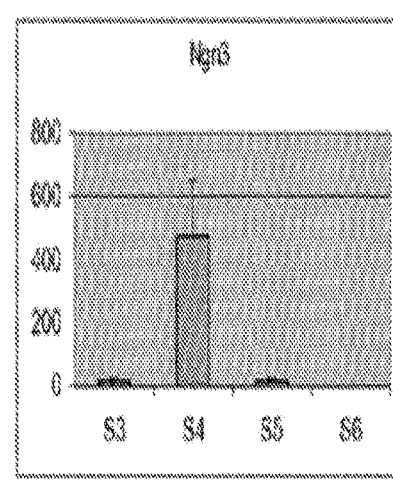
Figure 22J:
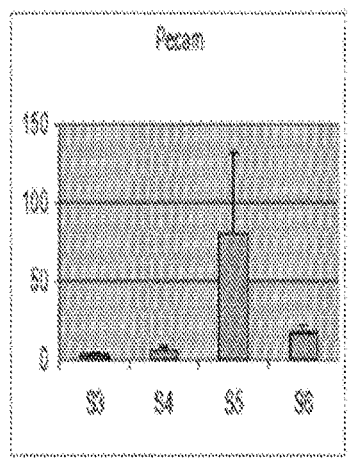
Figure 22K:
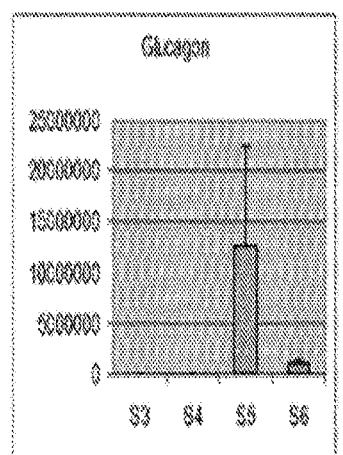
Figure 22L:
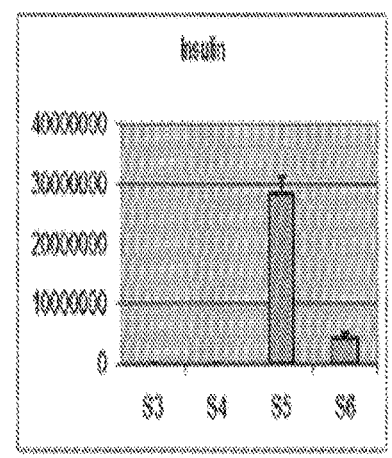
Figure 23A:
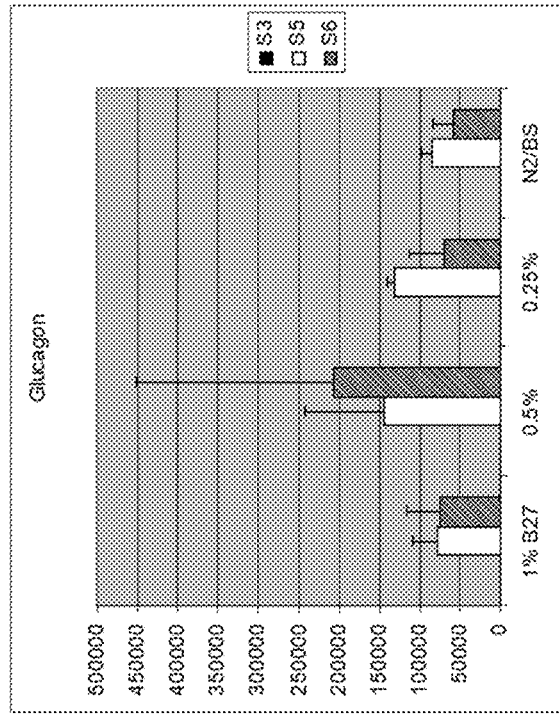
Figure 23B:
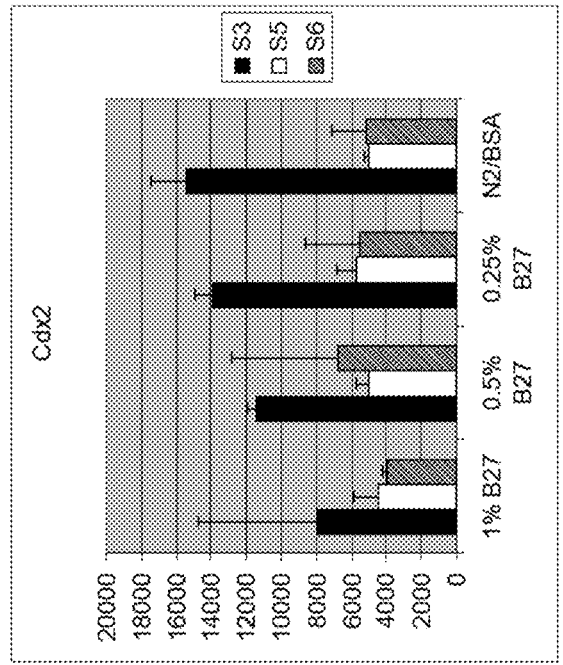
Figures 23C, 23D:
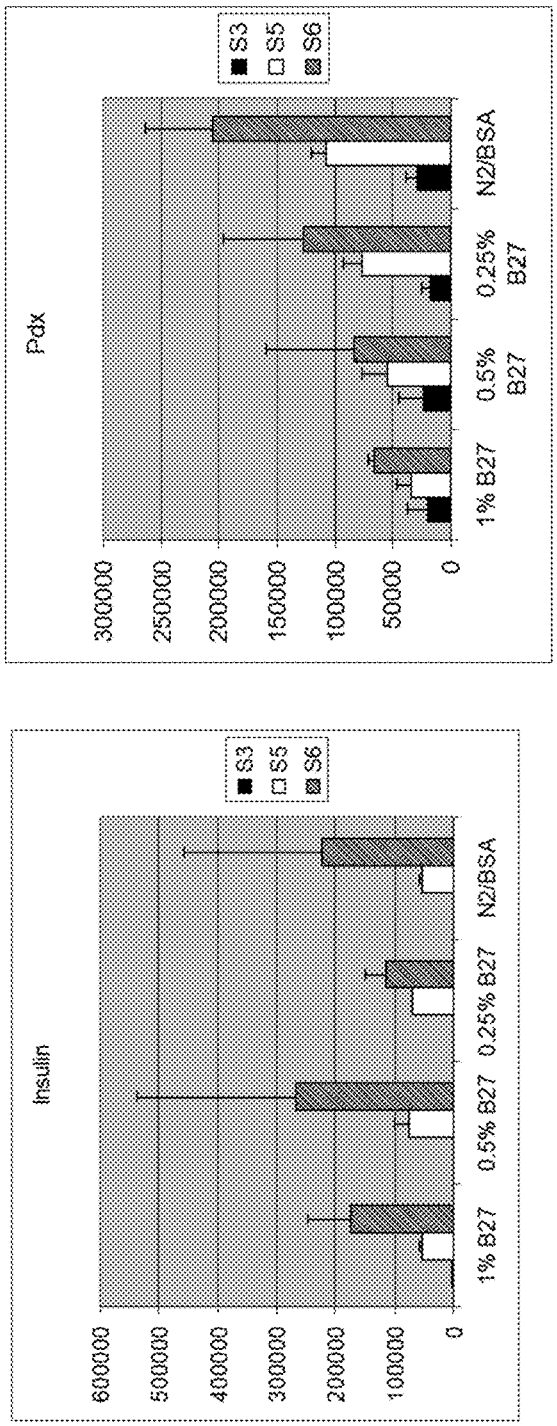

FIG. 19 shows C-peptide and pro-insulin content in cells at the end of stage 6 of the differentiation protocol outlined in FIG. 1C compared to adult human pancreatic islets.

FIGS. 20A-20C show the expression of insulin (FIG. 20A), synaptophysin (FIG. 20B) and co-expression of synaptophysin (X-axis) and insulin (Y-axis) (FIG. 20C) in cells at the end of stage 6 of the differentiation protocol outlined in FIG. 1C.

FIGS. 21A-21D show the expression of synaptophysin (FIG. 21A and FIG. 21C) and insulin (FIG. 21B and FIG. 21D) in cells at the end of stage 6 of the differentiation protocol outlined in FIG. 1C, that were treated with 100 ng/ml of Chordin instead of Noggin at stages 3-4.

FIGS. 22A-22L show the expression of various markers in cells of the human embryonic stem cell line H9 treated according to the differentiation protocol outlined in FIG. 1C. Data shown is the expression of FIG. 22A) HNF4a, FIG. 22B) HNF6, FIG. 22C) CDX2, FIG. 22D) PDX-1, FIG. 22E) NKX6.1, FIG. 22F) Pax4, FIG. 22G) NKX2.2, FIG. 22H) NeuroD, FIG. 22I) NGN3, FIG. 22J) PECAM FIG. 22K) glucagon, and FIG. 22L) insulin, as determined by real-time PCR in cells harvested at the end of stages 3-6.

FIGS. 23A-23D shows the expression of various markers in cells of the human embryonic stem cell line H1 treated according to the differentiation protocol outlined in FIG. 1C, where the cells were treated with either B27 or N2. Data shown is the expression of FIG. 23A) CDX2, FIG. 23B) glucagon, FIG. 23C) insulin, and FIG. 23D) PDX-1, as determined by real-time PCR in cells harvested at the end of stages 3-6.

DETAILED DESCRIPTION

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refers to cells with positive gene expression for the transcription factor PDX-1 and at least one of the following transcription factors: NGN-3, Nkx2.2, Nkx6.1, NeuroD, Isl-1, HNF-3 beta, MAFA, Pax4, and Pax6. Cells expressing markers characteristic of the β cell lineage include β cells.

"Cells expressing markers characteristic of the definitive endoderm lineage", as used herein, refers to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX-1, HNF-1beta, PTF-1 alpha, HNF-6, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", as used herein, refers to cells expressing at least one of the following markers: NGN-3, NeuroD, Islet-1, PDX-1, NKX6.1, Pax-4, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm", as used herein, refers to cells which bear the characteristic of cells arising from the epiblast during gastrulation and which form the gastrointestinal tract and its derivatives. Definitive endoderm cells express the following markers: HNF-3 beta, GATA-4, SOX-17, Cerberus, OTX2, goosecoid, C-Kit, CD99, and Mix11.

"Extraembryonic endoderm", as used herein, refers to a population of cells expressing at least one of the following markers: SOX-7, AFP, and SPARC.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell", as used herein, refers to a cell expressing at least one of the following markers: CD48, eomesodermin (EOMES), SOX-17, DKK4, HNF-3 beta, GSC, FGF17, GATA-6.

"Pancreatic endocrine cell", or "pancreatic hormone expressing cell", as used herein, refers to a cell capable of expressing at least one of the following hormones: insulin, glucagon, somatostatin, and pancreatic polypeptide.

"Pancreatic endoderm cell", as used herein, refers to a cell capable of expressing at least one of the following markers: NGN-3, NeuroD, Islet-1, PDX-1, PAX-4, NKX2.2.

"Pancreatic hormone producing cell", as used herein, refers to a cell capable of producing at least one of the following hormones: insulin, glucagon, somatostatin, and pancreatic polypeptide.

"Pancreatic hormone secreting cell" as used herein, refers to a cell capable of secreting at least one of the following hormones: insulin, glucagon, somatostatin, and pancreatic polypeptide.

"Posterior foregut cell", as used herein, refers to a cell capable of secreting at least one of the following markers: PDX-1, HNF-1, PTF-1A, HNF-6, HB-9, PROX-1.

"Pre-primitive streak cell", as used herein, refers to a cell expressing at least one of the following markers: Nodal, or FGF8.

"Primitive gut tube cell", as used herein, refers to a cell capable of secreting at least one of the following markers: HNF-1, HNF-4A.

"Primitive streak cell", as used herein, refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a suitable culture substrate is MATRIGEL® (Becton Dickenson). MATRIGEL® is a soluble preparation from Engelbreth-Holm-Swarm tumor cells that gels at room temperature to form a reconstituted basement membrane. Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristic. All these characteristic benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; 13-mercaptoethanol, Sigma #M7522; human recombinant basic fibroblast growth factor (bFGF), Gibco #13256-029.

Formation of Cells Capable of Glucose-Stimulated Insulin Secretion from Pluripotent Stem Cells In one embodiment, the present invention provides a method for producing cells capable of glucose-stimulated insulin secretion from pluripotent stem cells, comprising the steps of:
a. Culturing the pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

In one embodiment, the present invention provides a method for promoting glucose-stimulated insulin secretion in cells expressing markers characteristic of the pancreatic endocrine lineage derived from pluripotent stem cells, comprising the steps of:
a. Culturing the pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FoxD3, Connexin43, Connexin45, Oct4, Sox2, Nanog, hTERT, UTF-1, ZFP42, SSEA-3, SSEA-4, Tra1-60, Tra1-81.

Markers characteristic of the definitive endoderm lineage are selected from the group consisting of SOX-17, GATA4, Hnf-3beta, GSC, Cer1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN-3, NeuroD, Islet-1, Pdx-1, NKX6.1, Pax-4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN-3, Nkx2.2, Nkx6.1, NeuroD, Isl-1, HNF-3 beta, MAFA, Pax4, and Pax6. In one aspect of the present invention, a cell expressing markers characteristic of the 13 cell lineage is a 13 cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al., Nature Biotechnology 23, 1534-1541 (2005).

For example, pluripotent stem cells may be differentiated into cells expressing markers characteristic of the definitive endoderm lineage according to the methods disclosed in Shinozaki et al., Development 131, 1651-1662 (2004).

For example, pluripotent stem cells may be differentiated into cells expressing markers characteristic of the definitive endoderm lineage according to the methods disclosed in McLean et al., Stem Cells 25, 29-38 (2007).

For example, pluripotent stem cells may be differentiated into cells expressing markers characteristic of the definitive endoderm lineage according to the methods disclosed in D'Amour et al., Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in D'Amour et al., Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al., Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in US patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Detection of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristic of pluripotent stem cells are well known to those skilled in the art, and additional characteristic of pluripotent stem cells continue to be identified. Pluripotent stem cell markers include, for example, the expression of one or more of the following: ABCG2, cripto, FoxD3, Connexin43, Connexin45, Oct4, Sox2, Nanog, hTERT, UTF-1, ZFP42, SSEA-3, SSEA-4, Tra1-60, Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al., Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one embodiment, the present invention provides a method for differentiating cells expressing markers characteristic of the definitive endoderm lineage into cells expressing markers characteristic of the pancreatic endoderm lineage, comprising the steps of:
  a. Culturing cells expressing markers characteristic of the definitive endoderm lineage, and
  b. Treating the cells expressing markers characteristic of the definitive endoderm lineage with at least one factor selected from the group consisting of retinoic acid, FGF-2, FGF-4, FGF-7, FGF-10, a sonic hedgehog inhibitor, a factor capable of inhibiting BMP, and a netrin.

In one embodiment, the cells expressing markers characteristic of the definitive endoderm are treated with at least one factor selected from the group consisting of retinoic acid, FGF-2, FGF-4, FGF-7, FGF-10, a sonic hedgehog inhibitor, a factor capable of inhibiting BMP, and a netrin for about one to about six days. In one embodiment, the cells expressing markers characteristic of the definitive endoderm are treated with at least one factor selected from the group consisting of retinoic acid, FGF-2, FGF-4, FGF-7, FGF-10, a sonic hedgehog inhibitor, a factor capable of inhibiting BMP, and a netrin for about six days.

Any cell expressing markers characteristic of the definitive endoderm lineage is suitable for differentiating into a cell expressing markers characteristic of the pancreatic endoderm lineage using this method.

In an alternate embodiment, the present invention provides a method for differentiating cells expressing markers characteristic of the definitive endoderm lineage into cells expressing markers characteristic of the pancreatic endoderm lineage, comprising the steps of:
  a. Culturing cells expressing markers characteristic of the definitive endoderm lineage,
  b. Treating the cells expressing markers characteristic of the definitive endoderm lineage treating the cells with at least one factor selected from the group consisting of retinoic acid, and a fibroblast growth factor, and
  c. Removing the at least one factor selected from the group consisting of retinoic acid, and a fibroblast growth factor and subsequently treating the cells with at least one factor selected from the group consisting of a sonic hedgehog inhibitor, retinoic acid, a fibroblast growth factor, a factor capable of inhibiting BMP, and a netrin.

In one embodiment, the cells expressing markers characteristic of the definitive endoderm are treated with at least one factor selected from the group consisting of retinoic acid, and a fibroblast growth factor for about one to about three days. In one embodiment, the cells expressing markers characteristic of the definitive endoderm are treated with at least one factor selected from the group consisting of retinoic acid, and a fibroblast growth factor for about three days. In one embodiment, the cells expressing markers characteristic of the definitive endoderm are treated with at least one factor selected from the group consisting of a sonic hedgehog inhibitor, retinoic acid, a fibroblast growth factor, a factor capable of inhibiting BMP, and a netrin for about one to about four days. In one embodiment, the cells expressing markers characteristic of the definitive endoderm are treated with at least one factor selected from the group consisting of a sonic hedgehog inhibitor, retinoic acid, a fibroblast growth factor, a factor capable of inhibiting BMP, and a netrin for about four days.

Any cell expressing markers characteristic of the definitive endoderm lineage is suitable for differentiating into a cell expressing markers characteristic of the pancreatic endoderm lineage using this method.

In one embodiment, cells expressing markers characteristic of the pancreatic endoderm lineage produced by the methods of the present invention show a decreased level of expression of markers associated with liver and intestinal tissues. In one embodiment, cells expressing markers characteristic of the pancreatic endoderm lineage produced by the methods of the present invention show a decreased level of expression of albumin and CDX-2.

The at least one fibroblast growth factor is selected from the group consisting of FGF-2, FGF-4, FGF-7 and FGF-10.

In one embodiment, the BMP is BMP4. In one embodiment, the at least one factor capable of inhibiting BMP4 is noggin.

The netrin is selected from the group consisting of netrin 1, netrin 2, and netrin 4.

Retinoic acid may be used at a concentration from about 1 nM to about 1 mM. In one embodiment, retinoic acid is used at a concentration of 1 µM.

FGF-2 may be used at a concentration from about 50 pg/ml to about 50 µg/ml. In one embodiment, FGF-2 is used at a concentration of 50 ng/ml.

FGF-4 may be used at a concentration from about 50 pg/ml to about 50 µg/ml. In one embodiment, FGF-4 is used at a concentration of 50 ng/ml.

FGF-7 may be used at a concentration from about 50 pg/ml to about 50 µg/ml. In one embodiment, FGF-7 is used at a concentration of 50 ng/ml.

FGF-10 may be used at a concentration from about 50 pg/ml to about 50 µg/ml. In one embodiment, FGF-10 is used at a concentration of 50 ng/ml.

Noggin may be used at a concentration from about 500 ng/ml to about 500 µg/ml. In one embodiment, noggin is used at a concentration of 100 ng/ml.

Netrin 1 may be used at a concentration from about 500 ng/ml to about 500 µg/ml. In one embodiment, netrin 1 is used at a concentration of 100 ng/ml.

Netrin 2 may be used at a concentration from about 500 ng/ml to about 500 µg/ml. In one embodiment, netrin 2 is used at a concentration of 100 ng/ml.

Netrin 4 may be used at a concentration from about 500 ng/ml to about 500 µg/ml. In one embodiment, netrin 4 is used at a concentration of 100 ng/ml.

In one embodiment, the cells expressing markers characteristic of the definitive endoderm lineage are treated with at least one of the following factors: retinoic acid, FGF-2, FGF-4, FGF-7, FGF-10, cyclopamine, noggin, netrin 1, netrin 2, or netrin 4.

In one embodiment, the cells expressing markers characteristic of the definitive endoderm lineage are treated with retinoic acid, FGF-2, cyclopamine, and noggin. In an alternate embodiment, the cells expressing markers characteristic of the definitive endoderm lineage are treated with retinoic acid, FGF-4, cyclopamine, and noggin. In an alternate embodiment, the cells expressing markers characteristic of the definitive endoderm lineage are treated with retinoic acid, FGF-7, cyclopamine, and noggin. In an alternate embodiment, the cells expressing markers characteristic of the definitive endoderm lineage are treated with retinoic acid, FGF-10, cyclopamine, and noggin.

In one embodiment, the cells expressing markers characteristic of the definitive endoderm lineage are treated with retinoic acid, FGF-2, cyclopamine, and a netrin. In an alternate embodiment, the cells expressing markers characteristic of the definitive endoderm lineage are treated with retinoic acid, FGF-4, cyclopamine, and a netrin. In an alternate embodiment, the cells expressing markers characteristic of the definitive endoderm lineage are treated with retinoic acid, FGF-7, cyclopamine, and a netrin. In an alternate embodiment, the cells expressing markers characteristic of the definitive endoderm lineage are treated with retinoic acid, FGF-10, cyclopamine, and a netrin.

The netrin is selected from the group consisting of netrin 1, netrin 2, and netrin 4.

In one embodiment, the cells expressing markers characteristic of the definitive endoderm lineage are treated with retinoic acid, FGF-2, cyclopamine, noggin and a netrin. In an alternate embodiment, the cells expressing markers characteristic of the definitive endoderm lineage are treated with retinoic acid, FGF-4, cyclopamine, noggin and a netrin. In an alternate embodiment, the cells expressing markers characteristic of the definitive endoderm lineage are treated with retinoic acid, FGF-7, cyclopamine, noggin and a netrin. In an alternate embodiment, the cells expressing markers characteristic of the definitive endoderm lineage are treated with retinoic acid, FGF-10, cyclopamine, noggin and a netrin.

The netrin is selected from the group consisting of netrin 1, netrin 2, and netrin 4.

Cells expressing markers characteristic of the definitive endoderm lineage may be treated with at least one other additional factor that may enhance the formation of cells expressing markers characteristic of the pancreatic endoderm lineage.

Alternatively, the at least one other additional factor may enhance the proliferation of the cells expressing markers characteristic of the pancreatic endoderm lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloids such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, Hlxb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al., Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al., Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al., Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al., Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the TGF-βR-1 pathway. The factor that inhibits the TGF-βR-1 pathway may be an antagonist for the TGF-β extracellular receptor-1. Alternatively, the factor may inhibit the biological activity of the TGF-βR-1 receptor. Alternatively, the factor may inhibit or be an antagonist of an element in the TGF-βR-1 signal transduction pathway within a cell.

The cells expressing markers characteristic of the pancreatic endoderm lineage are treated with the factor inhibits the TGF-βR-1 pathway for about one to about twelve days. Alternatively, the cells expressing markers characteristic of the pancreatic endoderm lineage are treated with the factor that inhibits the TGF-βR-1 pathway for about five to about twelve days. Alternatively, the cells expressing markers characteristic of the pancreatic endoderm lineage are treated with the factor that inhibits the TGF-βR-1 pathway for about twelve days.

Any cell expressing markers characteristic of the pancreatic endoderm lineage is suitable for differentiating into a cell expressing markers characteristic of the pancreatic endocrine lineage using this method.

In one embodiment, the present invention provides a method for differentiating cells expressing markers characteristic of the pancreatic endoderm lineage into cells expressing markers characteristic of the pancreatic endocrine lineage, comprising the steps of:
 a. Culturing cells expressing markers characteristic of the pancreatic endoderm lineage, and
 b. Treating the cells with a factor that inhibits the Notch signaling pathway, and a factor that inhibits the TGF-βR-1 signaling pathway.

The cells expressing markers characteristic of the pancreatic endoderm lineage are treated with the factor that inhibits the Notch signaling pathway and the factor that inhibits the TGF-βR-1 pathway for about one to about twelve days. Alternatively, the cells expressing markers characteristic of the pancreatic endoderm lineage are treated with the factor that inhibits the Notch signaling pathway and the factor that inhibits the TGF-βR-1 pathway for about five to about twelve days. Alternatively, the cells expressing markers characteristic of the pancreatic endoderm lineage are treated with the factor that inhibits the Notch signaling pathway and the factor that inhibits the TGF-βR-1 pathway for about twelve days.

Any cell expressing markers characteristic of the pancreatic endoderm lineage is suitable for differentiating into a cell expressing markers characteristic of the pancreatic endocrine lineage using this method.

In one embodiment, the factor that inhibits the Notch signaling pathway is a γ-secretase inhibitor. In one embodiment, the γ-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

L-685,458 may be used at a concentration from about 0.1 µM to about 100 µM. In one embodiment, L-685,458 is used at a concentration of about 90 µM. In one embodiment, L-685,458 is used at a concentration of about 80 µM. In one embodiment, L-685,458 is used at a concentration of about 70 µM. In one embodiment, L-685,458 is used at a concentration of about 60 µM. In one embodiment, L-685,458 is used at a concentration of about 50 µM. In one embodiment, L-685,458 is used at a concentration of about 40 µM. In one embodiment, L-685,458 is used at a concentration of about 30 µM. In one embodiment, L-685,458 is used at a concentration of about 20 µM. In one embodiment, L-685,458 is used at a concentration of about 10 µM.

In one embodiment the factor that inhibits the TGF-βR-1 signaling pathway is an inhibitor of TGF-βR-1 kinase. In one embodiment, the TGF-βR-1 kinase inhibitor is (2-(3-(6-Methylpyridin-2-yl)-1H-pyrazol-4-yl)-1,5-naphthyridine). In another embodiment, the TGF-βR-1 kinase inhibitor is [3-(Pyridin-2-yl)-4-(4-quinonyl)]-1H-pyrazole.

The TGF-βR-1 kinase inhibitor may be used at a concentration from about 0.1 µM to about 100 µM. In one embodiment, TGF-βR-1 kinase inhibitor is used at a concentration of about 90 µM. In one embodiment, TGF-βR-1 kinase inhibitor is used at a concentration of about 80 µM. In one embodiment, TGF-βR-1 kinase inhibitor is used at a concentration of about 70 µM. In one embodiment, TGF-βR-1 kinase inhibitor is used at a concentration of about 60 µM. In one embodiment, TGF-βR-1 kinase inhibitor is used at a concentration of about 50 µM. In one embodiment, TGF-βR-1 kinase inhibitor is used at a concentration of about 40 µM. In one embodiment, TGF-βR-1 kinase inhibitor is used at a concentration of about 30 µM. In one embodiment, TGF-βR-1 kinase inhibitor is used at a concentration of about 20 µM. In one embodiment, TGF-βR-1 kinase inhibitor is used at a concentration of about 10 µM. In one embodiment, TGF-βR-1 kinase inhibitor is used at a concentration of about 1 µM. In one embodiment, TGF-βR-1 kinase inhibitor is used at a concentration of about 0.1 µM.

Cells expressing markers characteristic of the pancreatic endoderm lineage may be treated with at least one other additional factor that may enhance the formation of cells expressing markers characteristic of the pancreatic endocrine lineage. Alternatively, the at least one other additional factor may enhance the proliferation of the cells expressing markers characteristic of the pancreatic endocrine lineage formed by the methods of the present invention. Further, the at least one other additional factor may enhance the ability of the cells expressing markers characteristic of the pancreatic endocrine lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloids such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN-3, NeuroD, Islet-1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristic include the expression of one or more transcription factors such as, for example, Pdx1 (pancreatic and duodenal homeobox gene-1), Nkx2.2, Nkx6.1, Isl1, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the 13 cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

In one aspect of the present invention, the efficiency of differentiation is determined by measuring the percentage of insulin positive cells in a given cell culture following treatment. In one embodiment, the methods of the present invention produce about 100% insulin positive cells in a given culture. In an alternate embodiment, the methods of the present invention produce about 90% insulin positive cells in a given culture. In an alternate embodiment, the methods of the present invention produce about 80% insulin positive cells in a given culture. In an alternate embodiment, the methods of the present invention produce about 70% insulin positive cells in a given culture. In an alternate embodiment, the methods of the present invention produce about 60% insulin positive cells in a given culture. In an alternate embodiment, the methods of the present invention produce about 50% insulin positive cells in a given culture. In an alternate embodiment, the methods of the present invention produce about 40% insulin positive cells in a given culture. In an alternate embodiment, the methods of the present invention produce about 30% insulin positive cells in a given culture. In an alternate embodiment, the methods of the present invention produce about 20% insulin positive cells in a given culture. In an alternate embodiment, the methods of the present invention produce about 10% insulin positive cells in a given culture. In an alternate embodiment, the methods of the present invention produce about 5% insulin positive cells in a given culture.

In one aspect of the present invention, the efficiency of differentiation is determined by measuring glucose-stimulated insulin secretion, as detected by measuring the amount of C-peptide released by the cells. In one embodiment, cells produced by the methods of the present invention produce about 1000 ng C-peptide/pg DNA. In an alternate embodiment, cells produced by the methods of the present invention produce about 900 ng C-peptide/pg DNA. In an alternate embodiment, cells produced by the methods of the present invention produce about 800 ng C-peptide/pg DNA. In an alternate embodiment, cells produced by the methods of the present invention produce about 700 ng C-peptide/pg DNA. In an alternate embodiment, cells produced by the methods of the present invention produce about 600 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 300 ng C-peptide/pg DNA. In an alternate embodiment, cells produced by the methods of the present invention produce about 200 ng C-peptide/pg DNA. In an alternate embodiment, cells produced by the methods of the present invention produce about 100 ng C-peptide/pg DNA. In an alternate embodiment, cells produced by the methods of the present invention produce about 90 ng C-peptide/pg DNA. In an alternate embodiment, cells produced by the methods of the present invention produce about 80 ng C-peptide/pg DNA. In an alternate embodiment, cells produced by the methods of the present invention produce about 70 ng C-peptide/pg DNA. In an alternate embodiment, cells produced by the methods of the present invention produce about 60 ng C-peptide/pg DNA. In an alternate embodiment, cells produced by the methods of the present invention produce about 50 ng C-peptide/pg DNA. In an alternate embodiment, cells produced by the methods of the present invention produce about 40 ng C-peptide/pg DNA. In an alternate embodiment, cells produced by the methods of the present invention produce about 30 ng C-peptide/pg DNA. In an alternate embodiment, cells produced by the methods of the present invention produce about 20 ng C-peptide/pg DNA. In an alternate embodiment, cells produced by the methods of the present invention produce about 10 ng C-peptide/pg DNA.

Therapies

In one aspect, the present invention provides a method for treating a patient suffering from, or at risk of developing, Type 1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264, 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7,-11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Frog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

EXAMPLES

Example 1

Human Embryonic Stem Cell Culture

The human embryonic stem cell lines H1, H7 and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM betamercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 µg/ml mitomycin C (Sigma, St. Louis, Mo.) for 3h to arrest cell division, then trypsinized and plated at $2 \times 10^4/cm^2$ on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5-7 days after plating), human embryonic stem cells were treated with lmg/ml collagenase type IV (Invitrogen/GIBCO) for 5-10 min and then gently scraped off the surface using a 5-ml pipette. Cells were spun at 900 rpm for 5 min, and the pellet was resuspended and re-plated at a 1:3 to 1:4 ratio of cells in fresh culture medium.

Example 2

Differentiation of Human Embryonic Stem Cells Cultured on Tissue Culture Substrate Coated with MATRIGEL™ to Pancreatic Endocrine Cells Cells of the human embryonic stem cell line H1, at passage 45 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days, followed by treatment with DMEM/F12 media supplemented with 2% FBS and 100 ng/ml Activin-A (AA) for an additional three days. Next the cultures were treated with DMEM/F12+2% FBS+ 20 ng/ml FGF7+0.25 µm Cyclopamine-KAAD (#239804, Calbiochem, CA) for three days followed by four day incubation in DMEM/F12+1% B27 (Invitrogen, CA)+20 ng/ml FGF7+0.25 µm Cyclopamine-KAAD+2 µm Retinoic acid (RA) (Sigma, MO).

Figure 2:
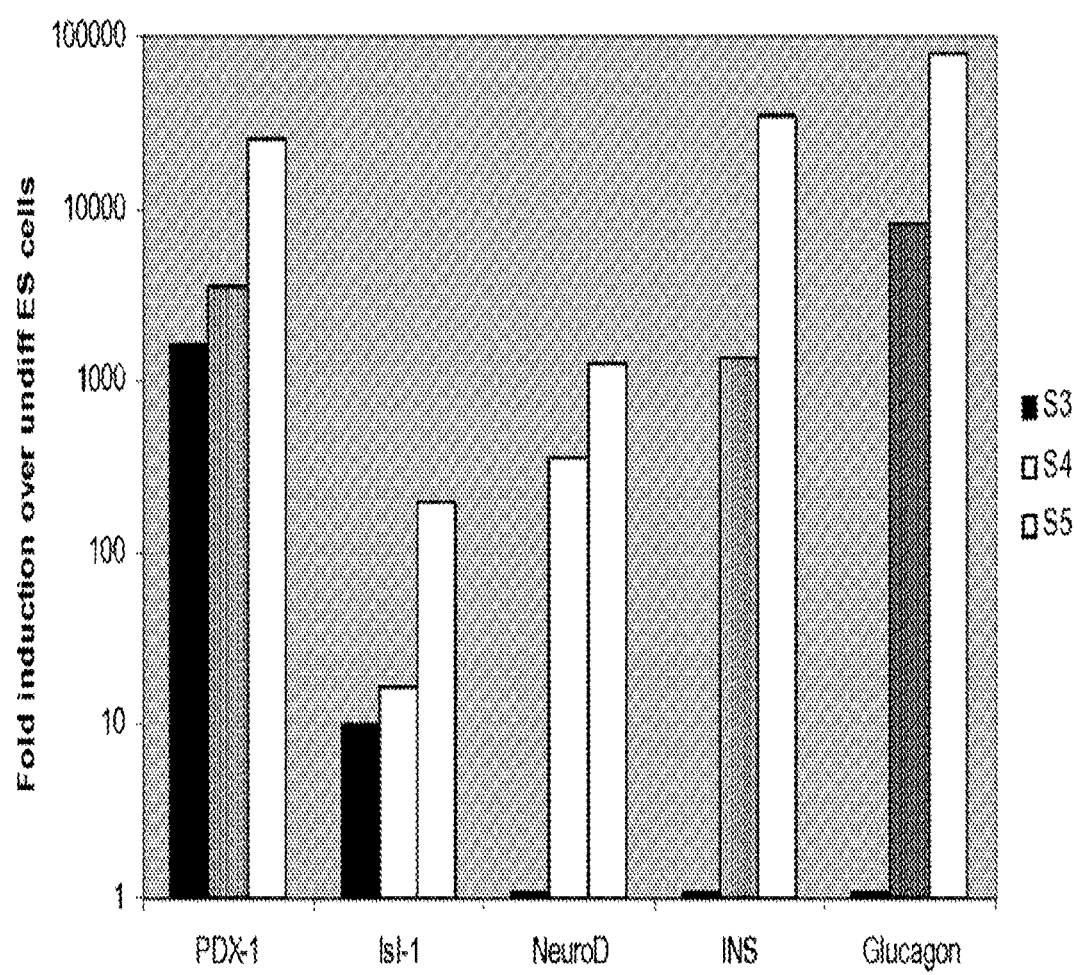
FIG. 2 shows real-time PCR analysis of cells of the human embryonic stem cell line H1, differentiated according to the methods disclosed in Example 2. Expression of pancreatic endoderm (PDX-1, ISL-1) and endocrine markers (NeuroD, Insulin, and glucagon) is depicted at stages 3 to 5 (S3-S5). There was a significant increase in expression of insulin and glucagon at stages 4 to 5.
Figure 3A:
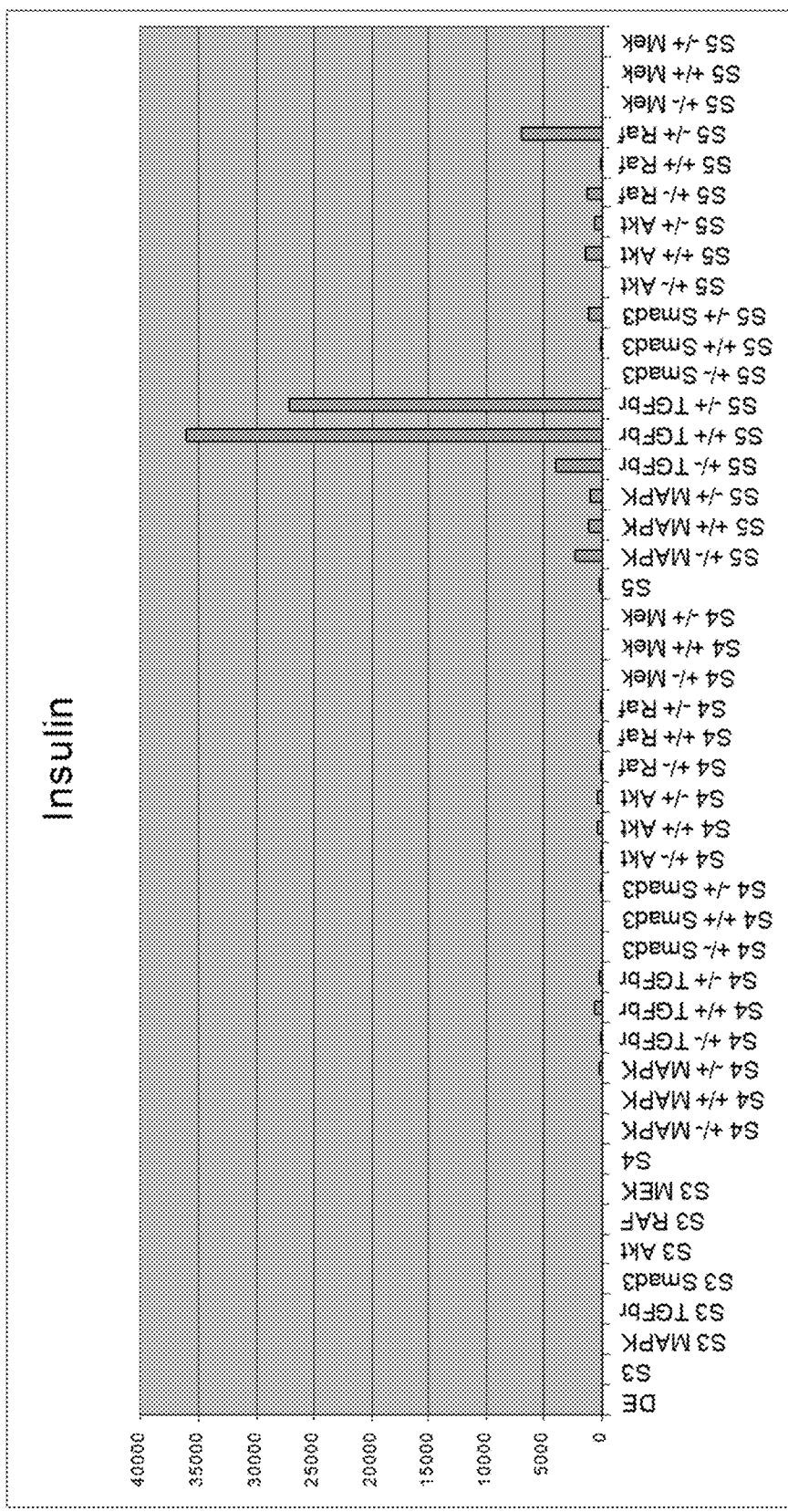
FIGS. 3A-3E show real-time PCR analysis of cells of the human embryonic stem cell line H1, differentiated according to the methods disclosed in Example 3. Pancreatic endocrine FIG. 3A) insulin, FIG. 3B) NKX2, FIG. 3C) glucagon, FIG. 3D) NeuroD, and pancreatic endoderm marker FIG. 3E) PDX-1 at stages 3 to 5. The effect of various kinase inhibitors were evaluated at either stage 3, stage 4, or at stages 3 and 4. (+/+ refers to the presence of a particular compound at both stages 3 and 4, +/− refers to the presence of a particular compound at stage 3 and its absence at stage 4, −/+ refers to the presence of a particular compound at stage 4 and its absence at stage 3).
Figure 3B:
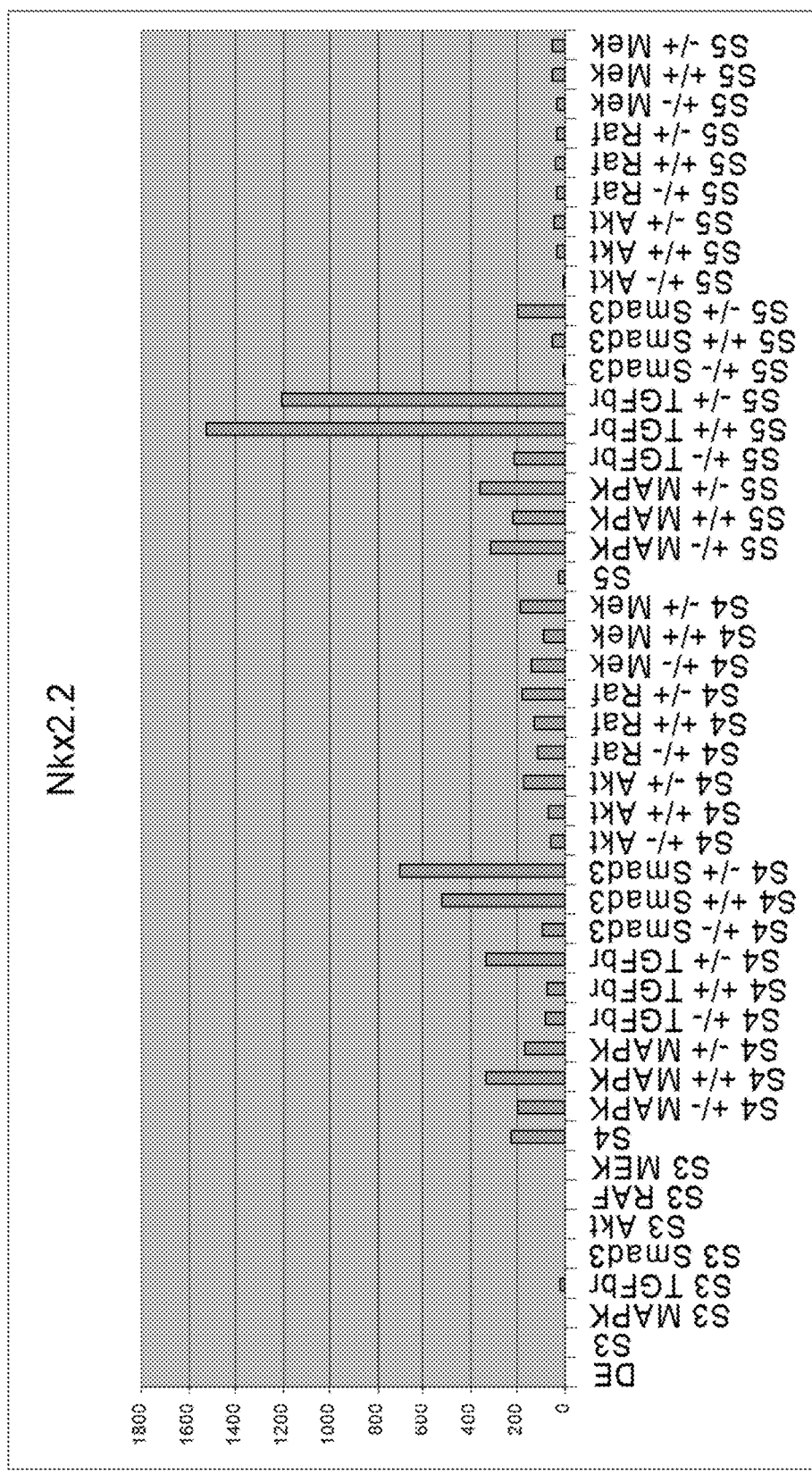
Figure 3C:
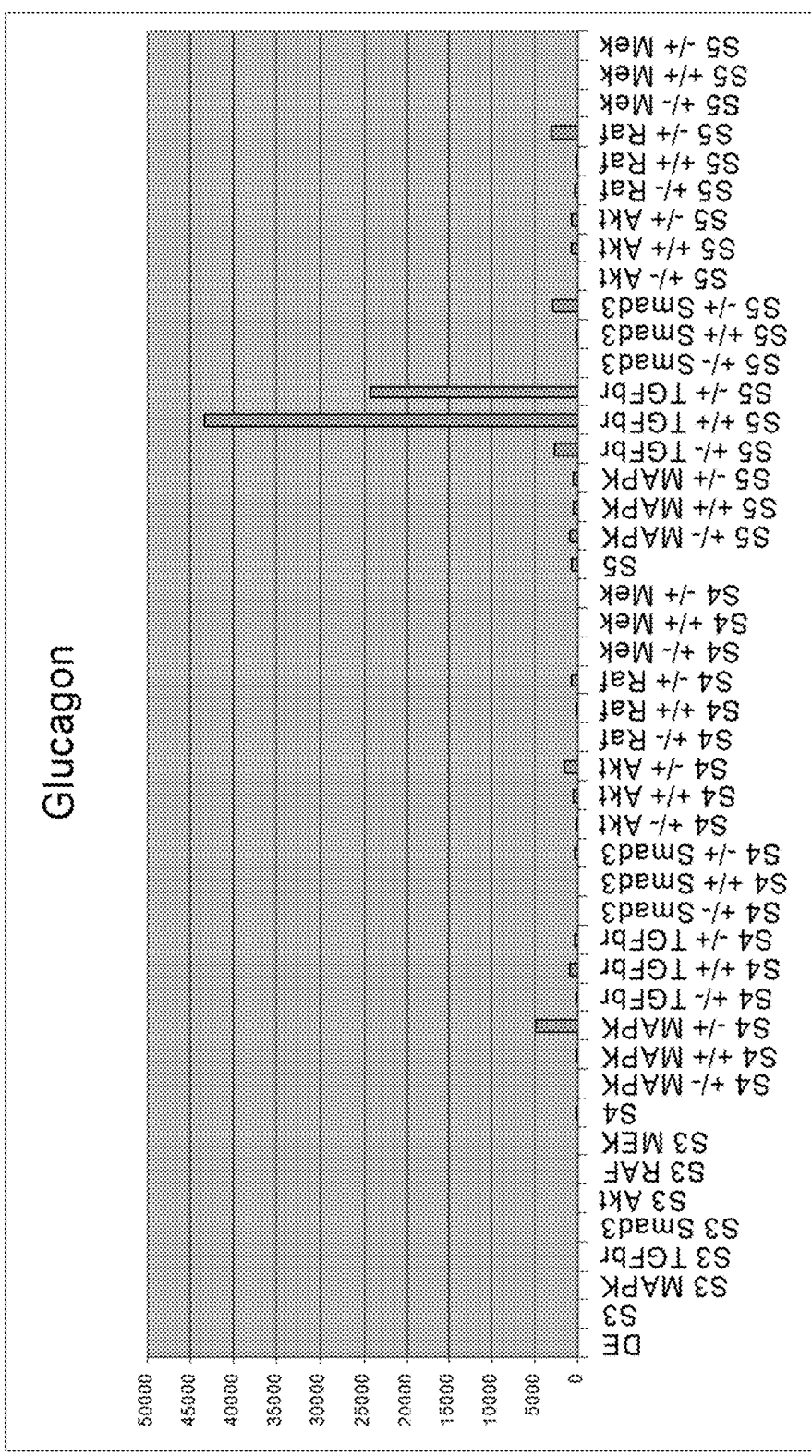
Figure 3D:
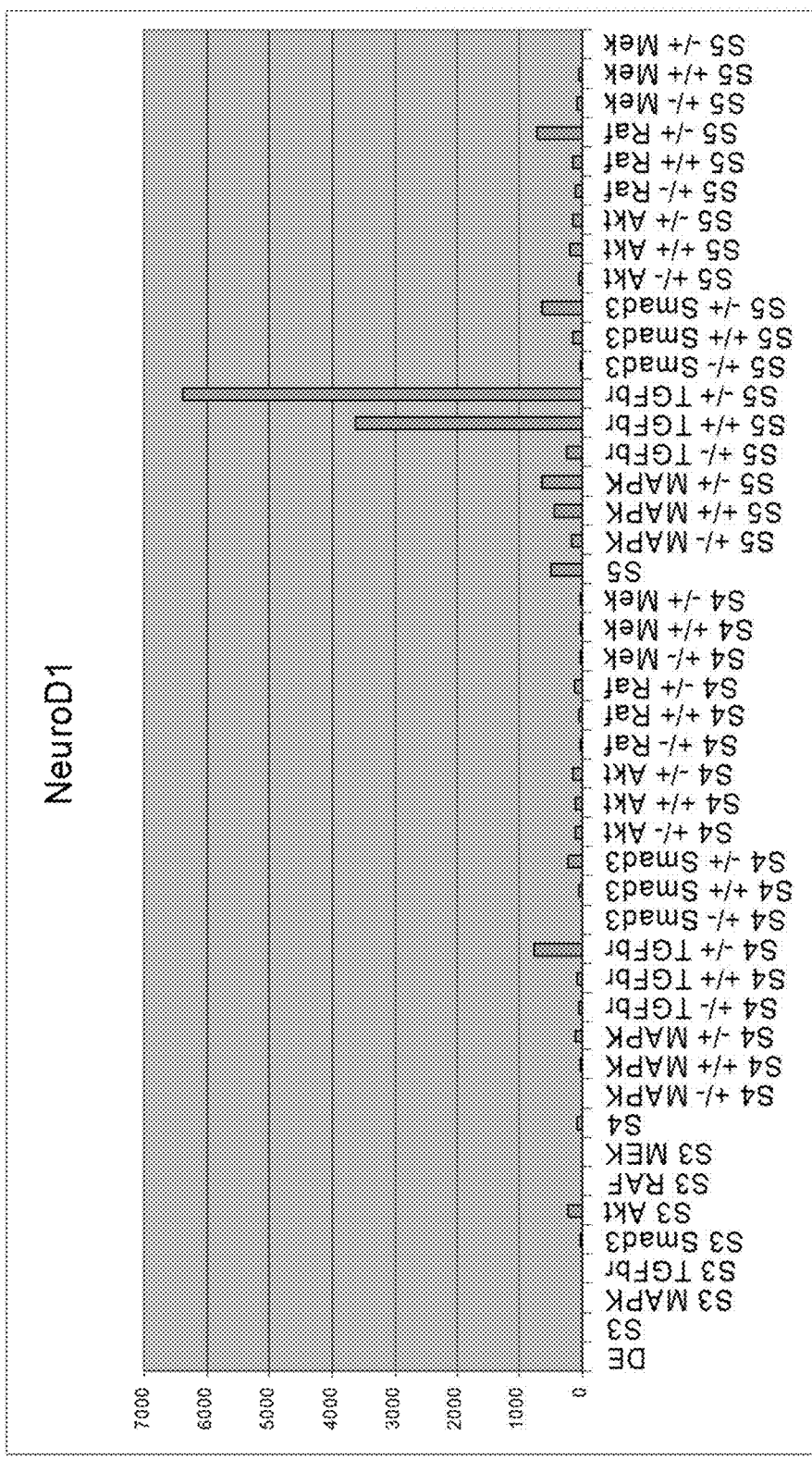
Figure 3E:
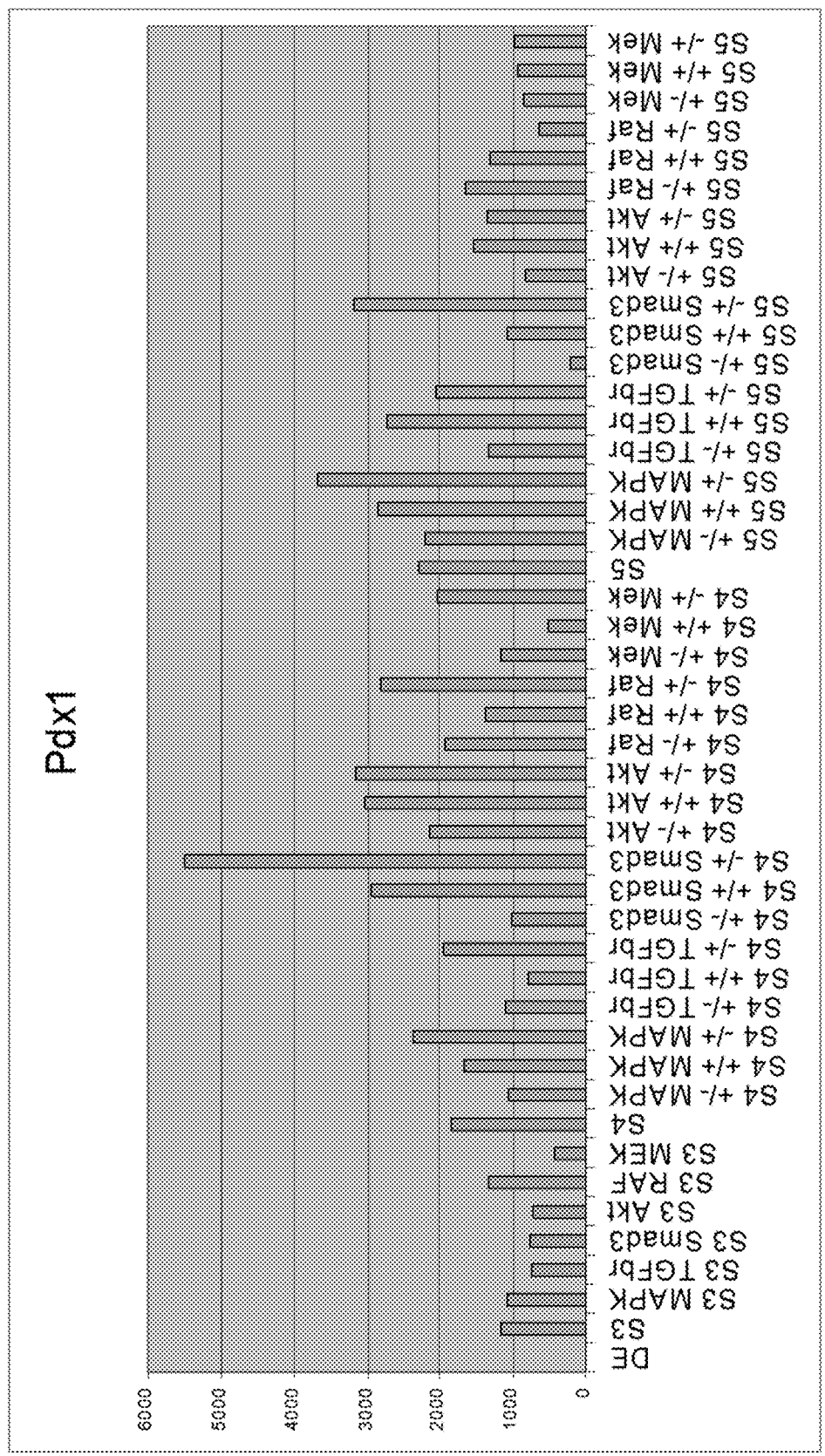
Figure 4A:
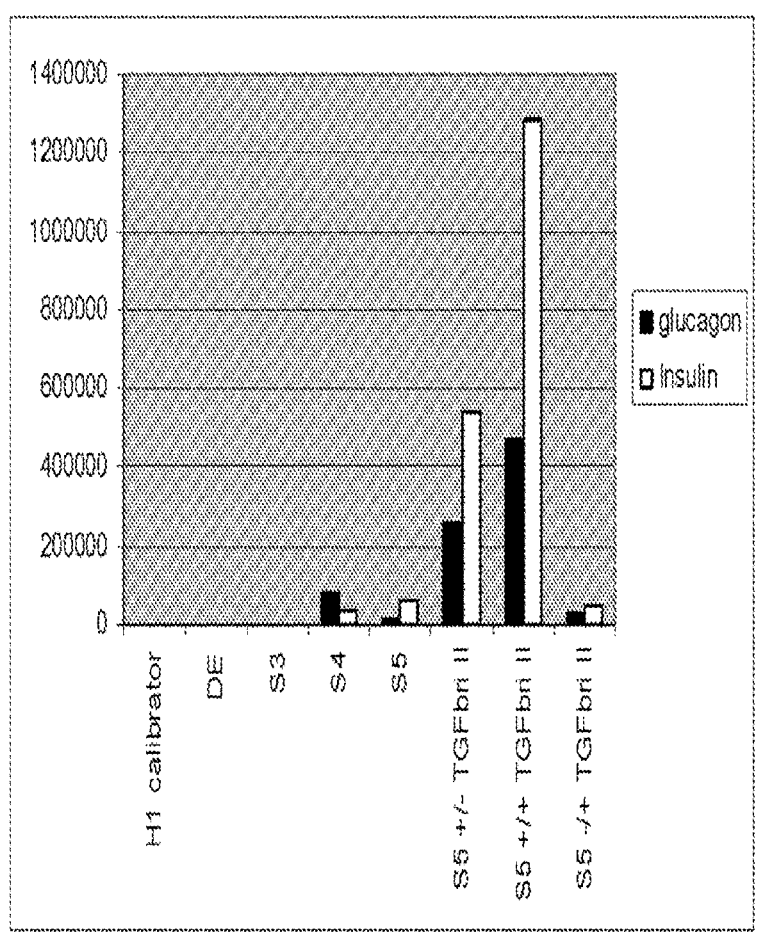
FIGS. 4A-4D show real-time PCR analysis of cells of the human embryonic stem cell line H1, differentiated according to the methods disclosed in Example 4. Pancreatic markers FIG. 4A) glucagon and insulin, FIG. 4B) HAND1 and NeuroD, FIG. 4C) HNF4a and PDX-1, FIG. 4D) NKX2.2 and Sox17, is depicted at stages 3 to 5. The effect of ALK5 inhibitor II was valuated at either stage 4, stage 5, or at stages 4 and 5. (+/+ refers to the presence of the inhibitor at both stages 4+5, +/− refers to the presence of the inhibitor at stage 4 and its absence at stage 5, −/+ refers to the presence of the inhibitor at stage Sand its absence at stage 4).
Figure 4B:
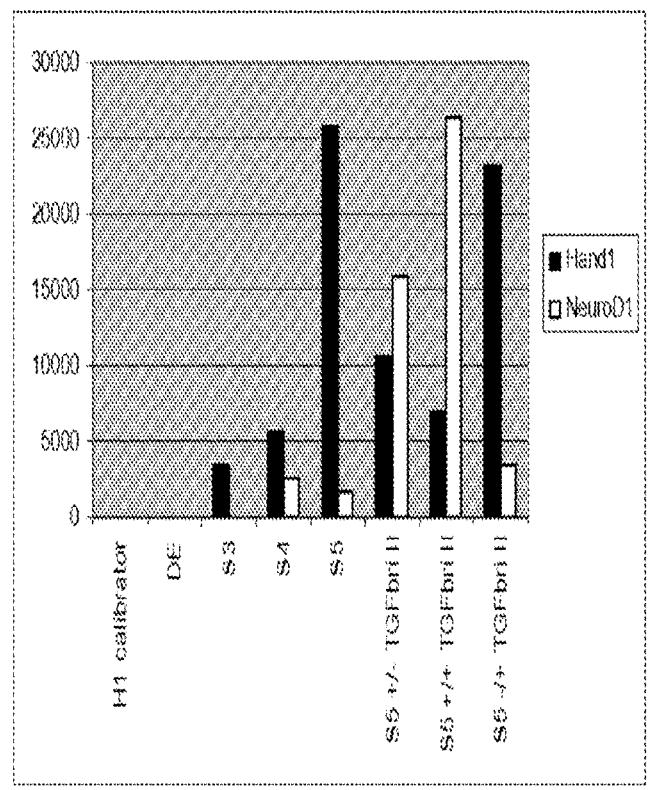
Figure 4C:
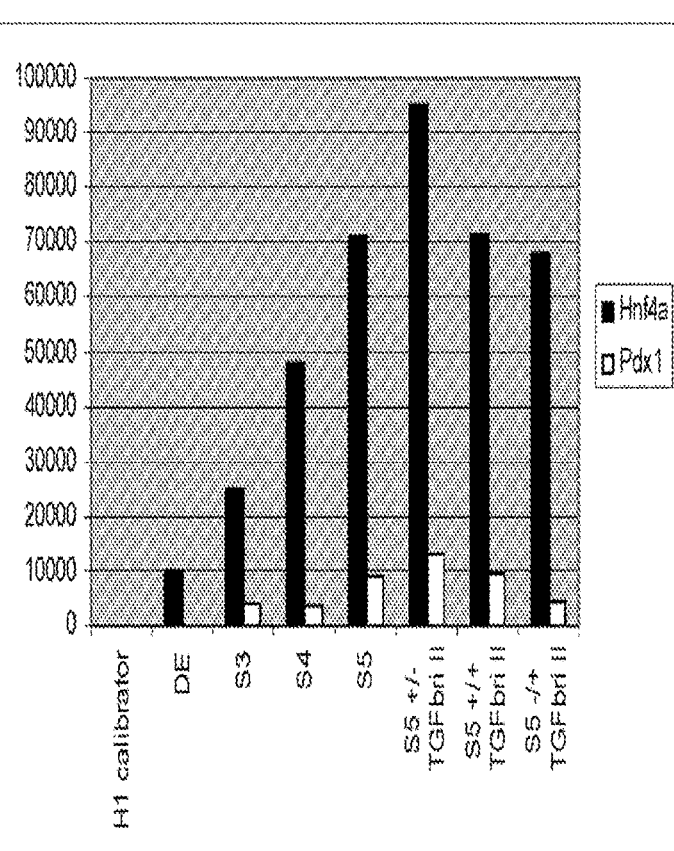
Figure 4D:
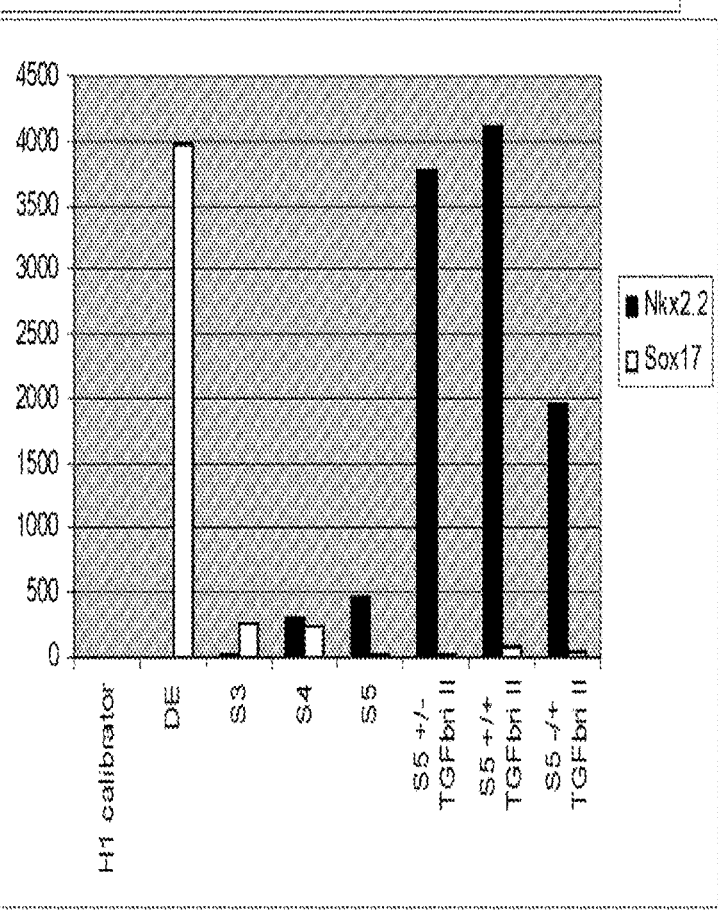
Figure 5A:
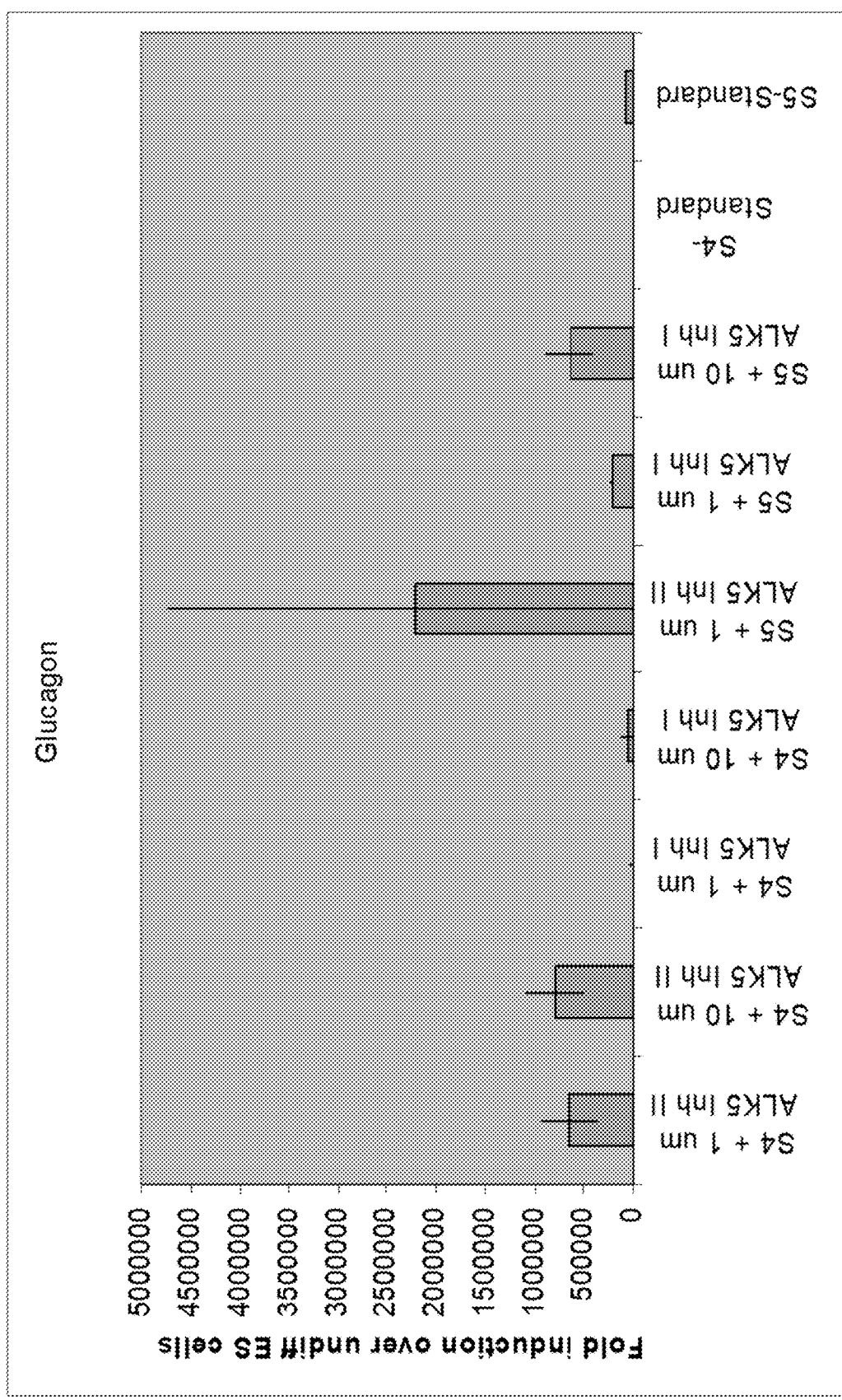
Figure 5B:
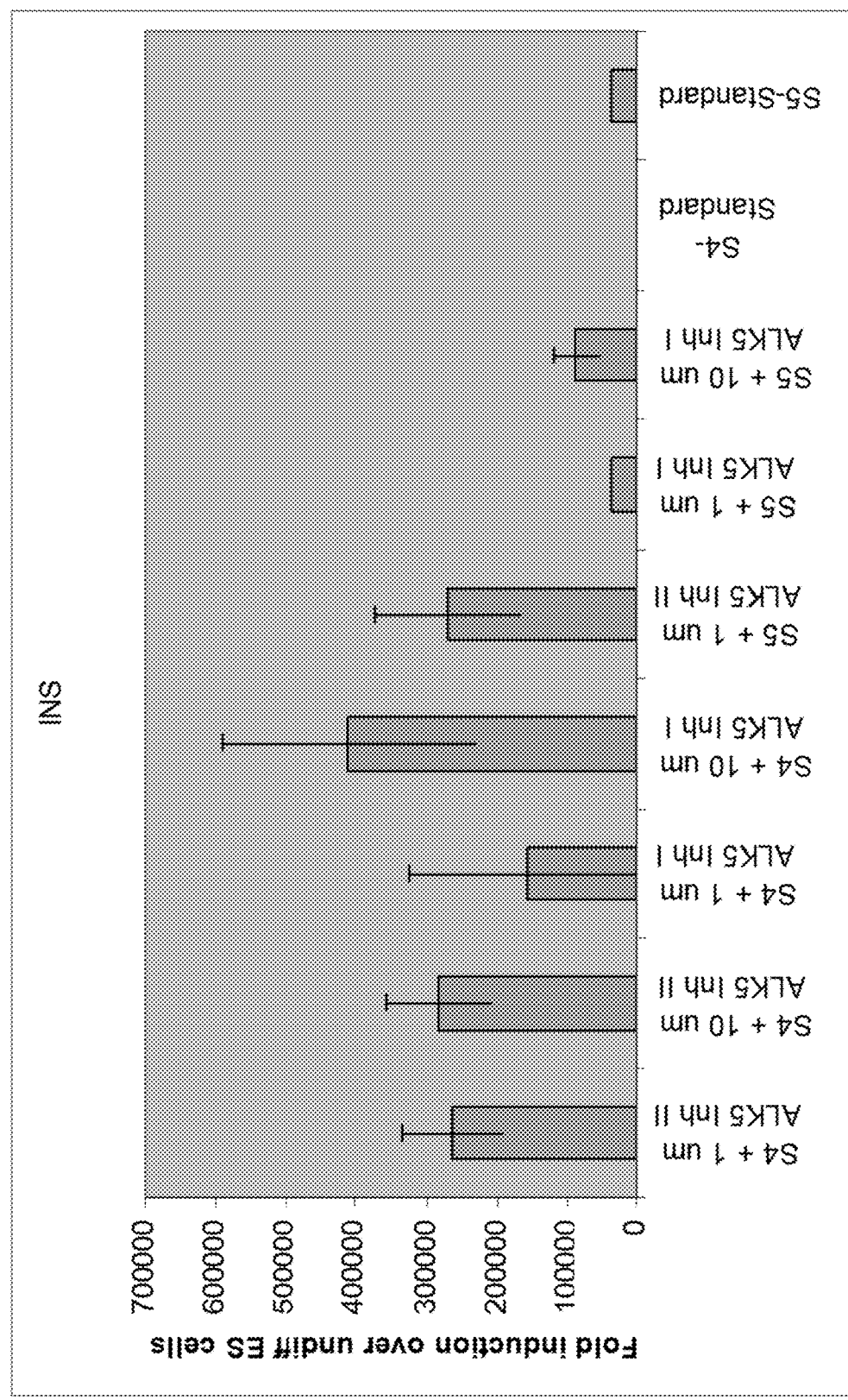
Figure 5C:
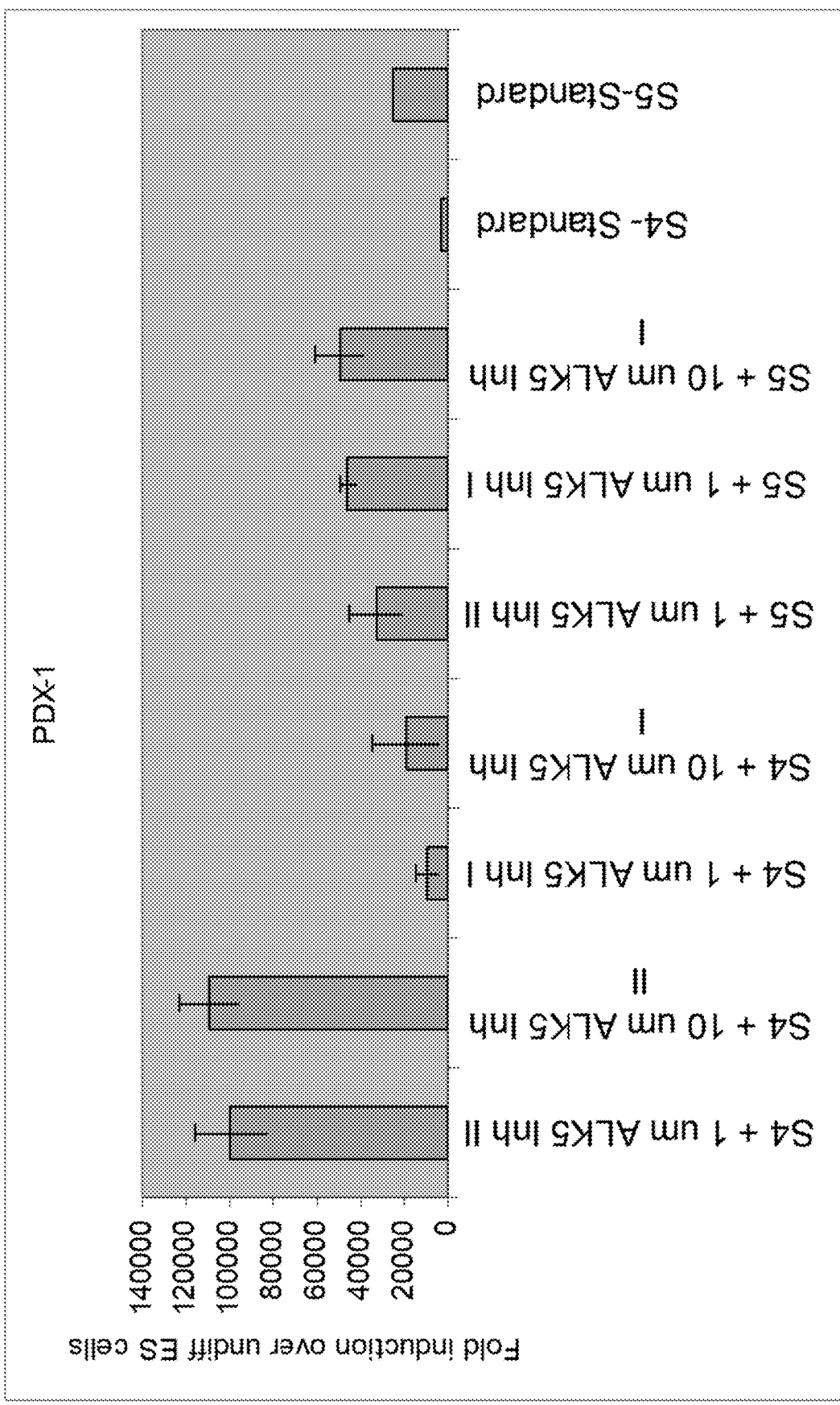
Figure 5D:
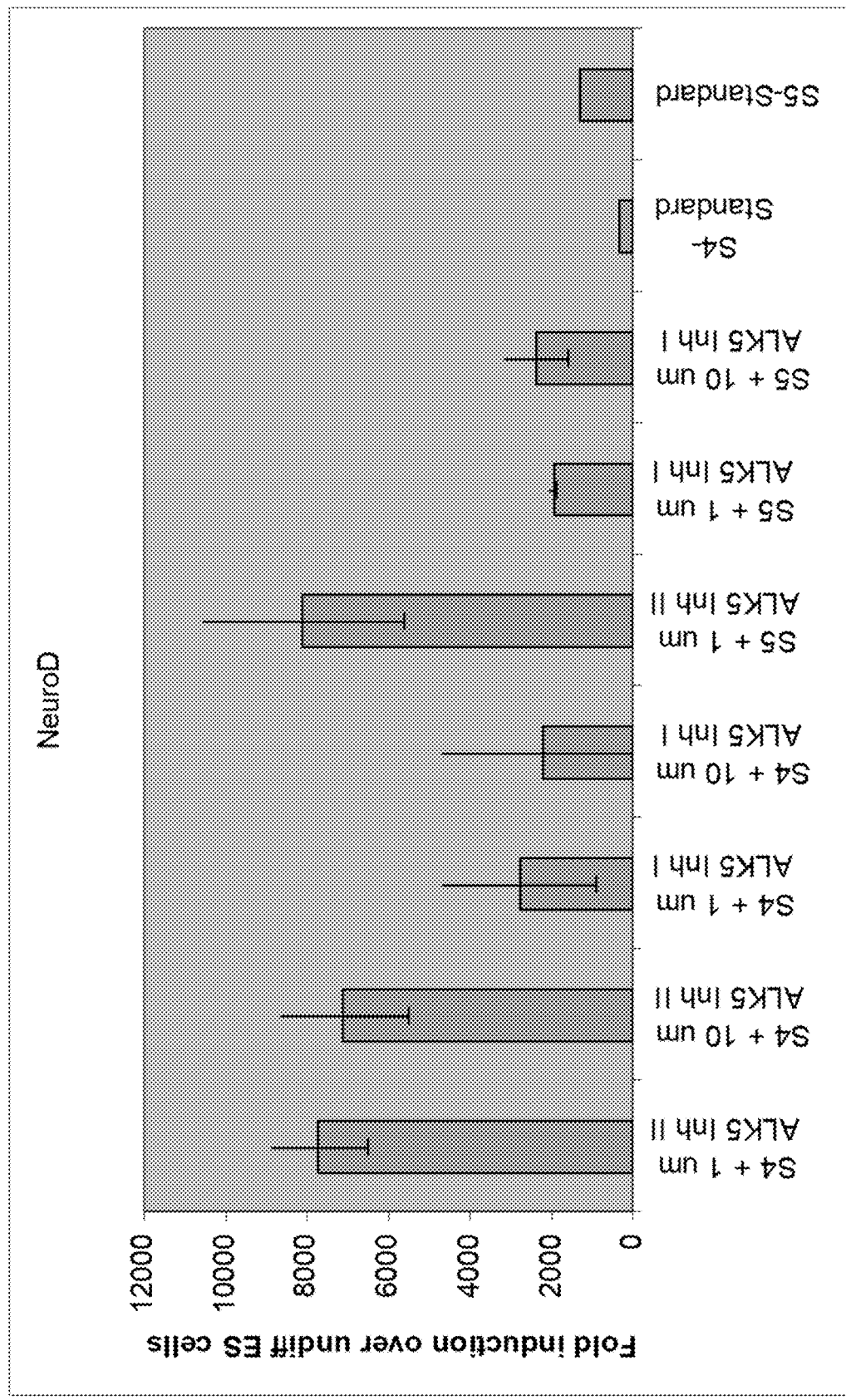
Figure 6A:
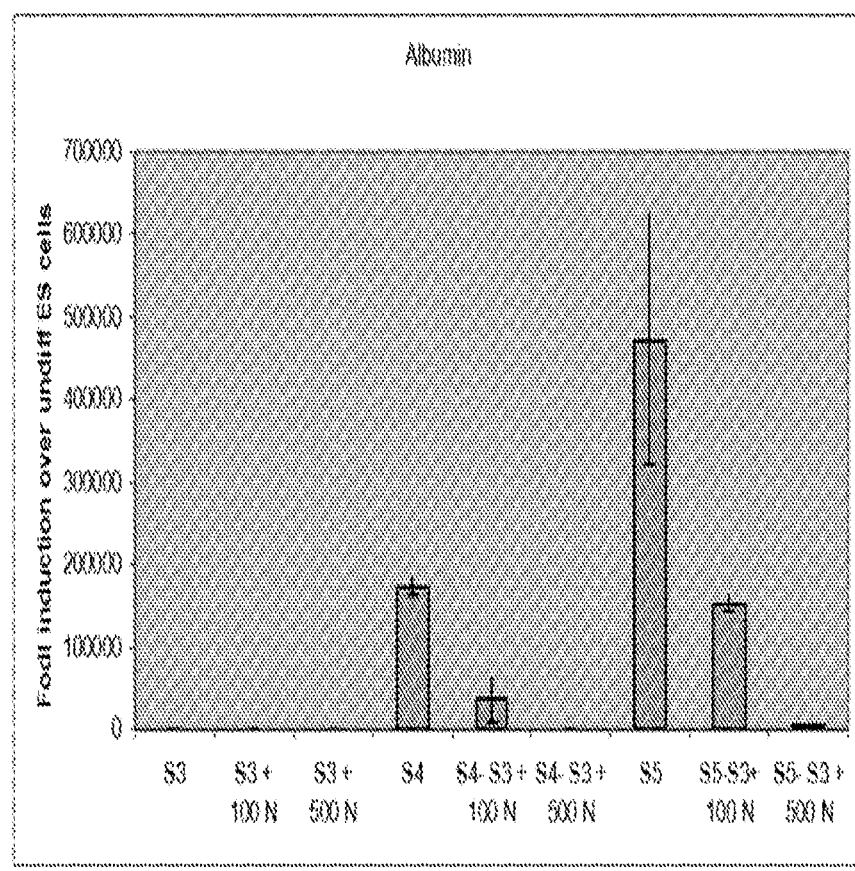
Figure 6B:
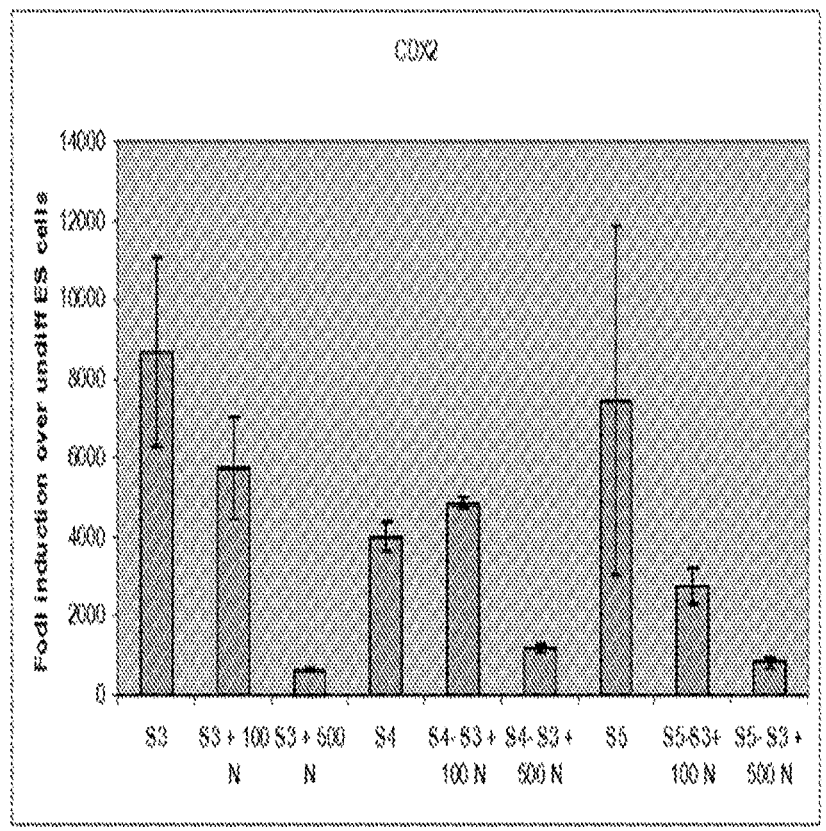
Figure 6C:
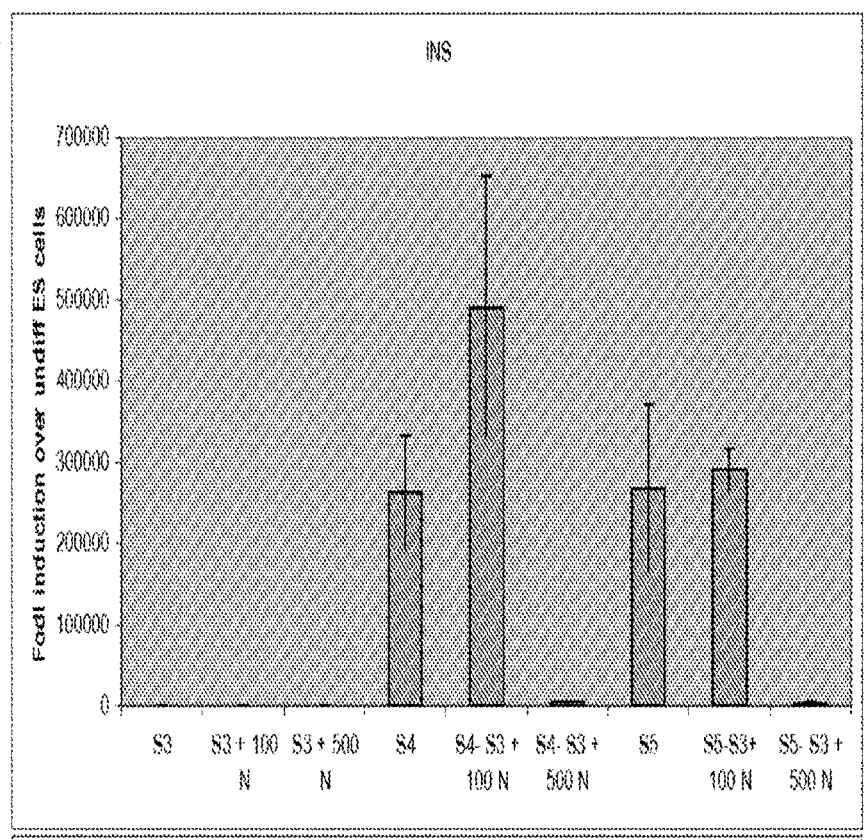
Figure 6D:
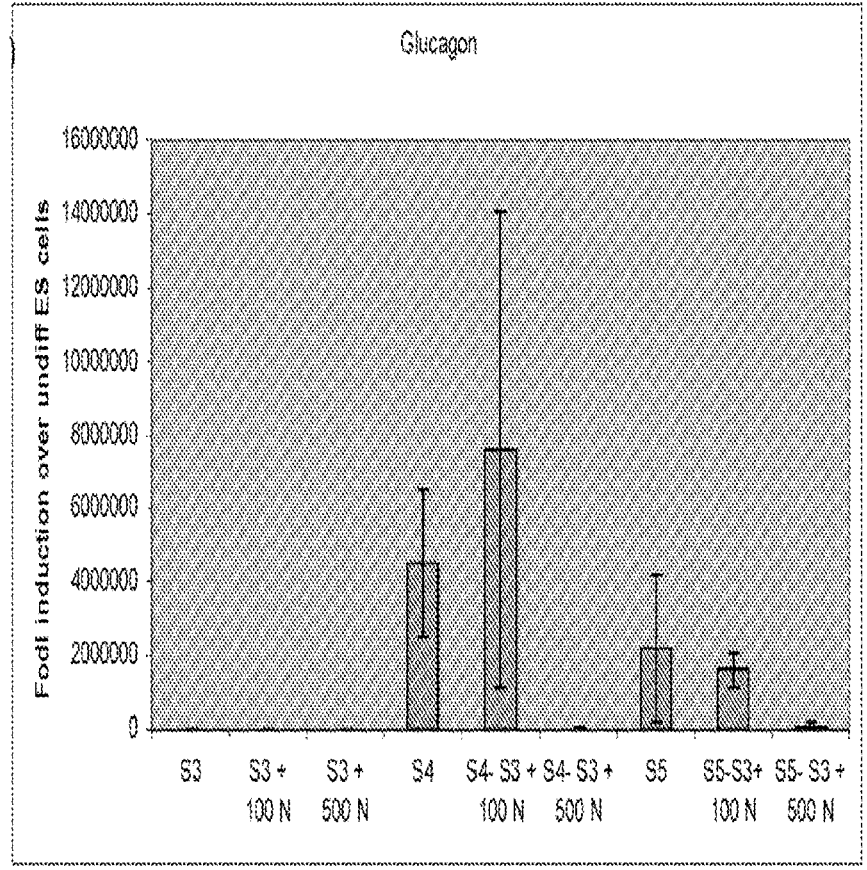
Figure 6E:
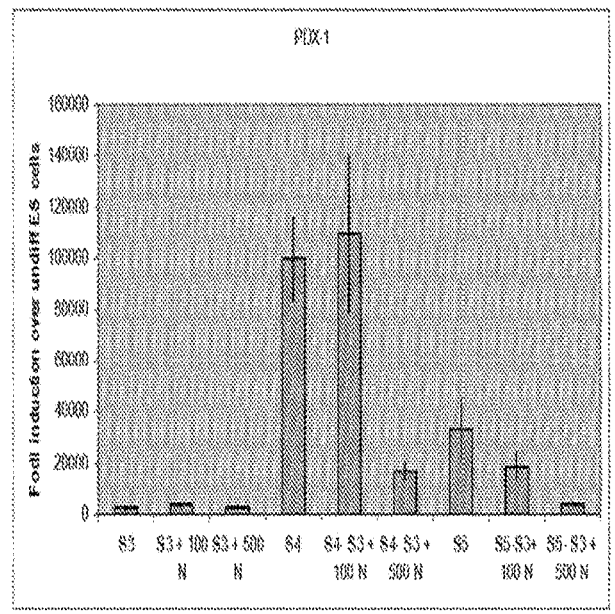
Figure 6G:
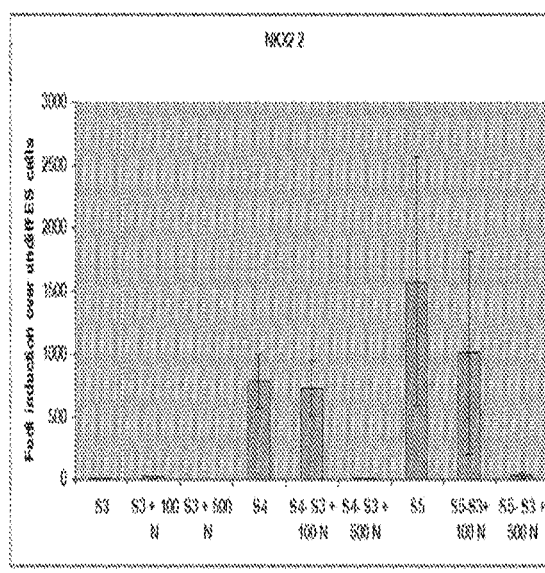
Figure 6F:
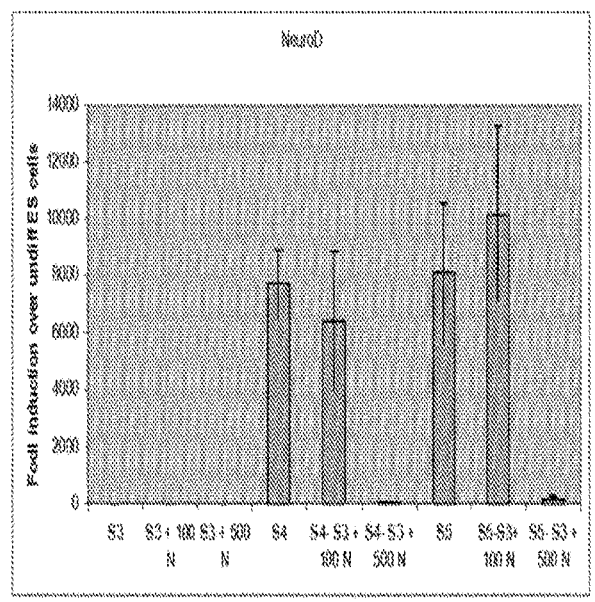
Figure 7A:
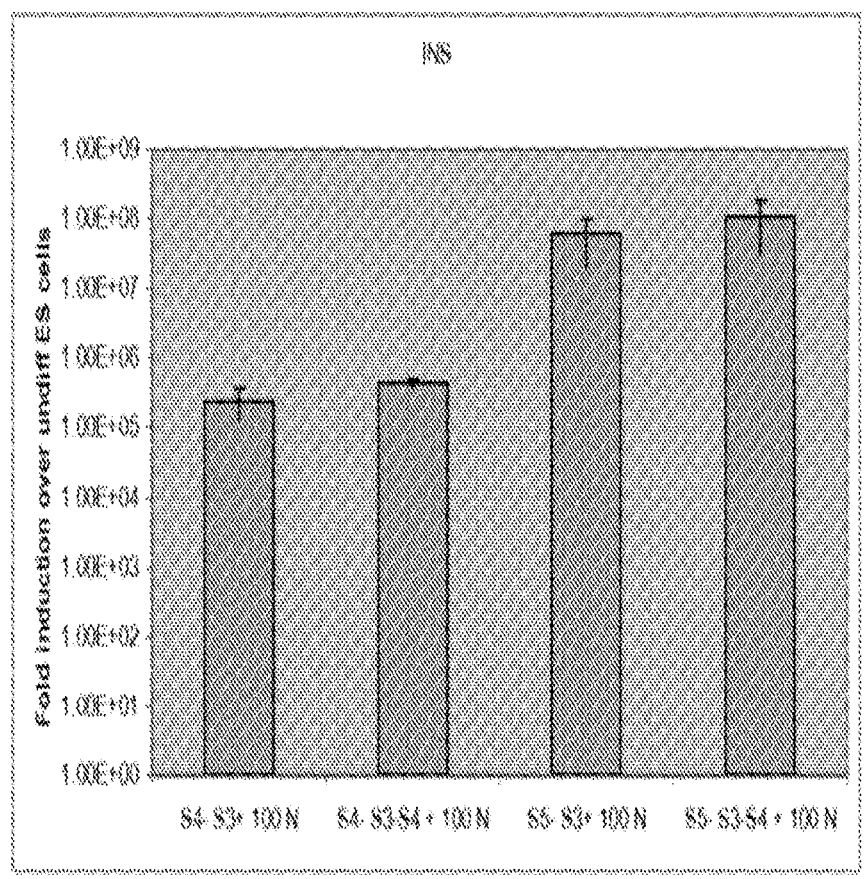
Figure 7B:
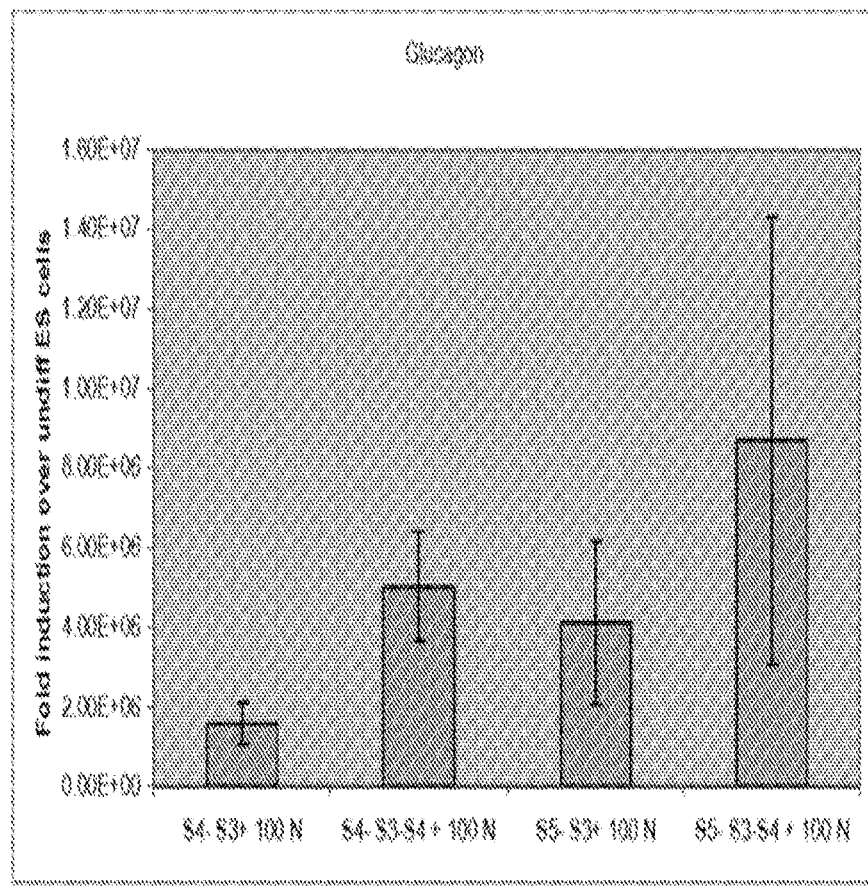
Figure 7C:
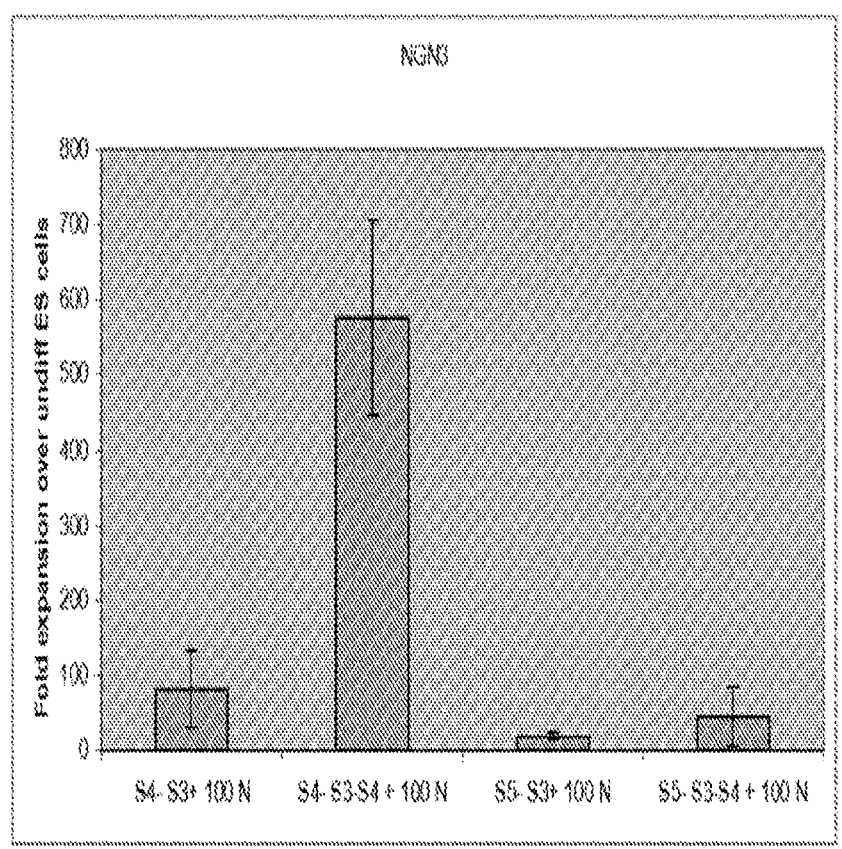
Figure 7D:
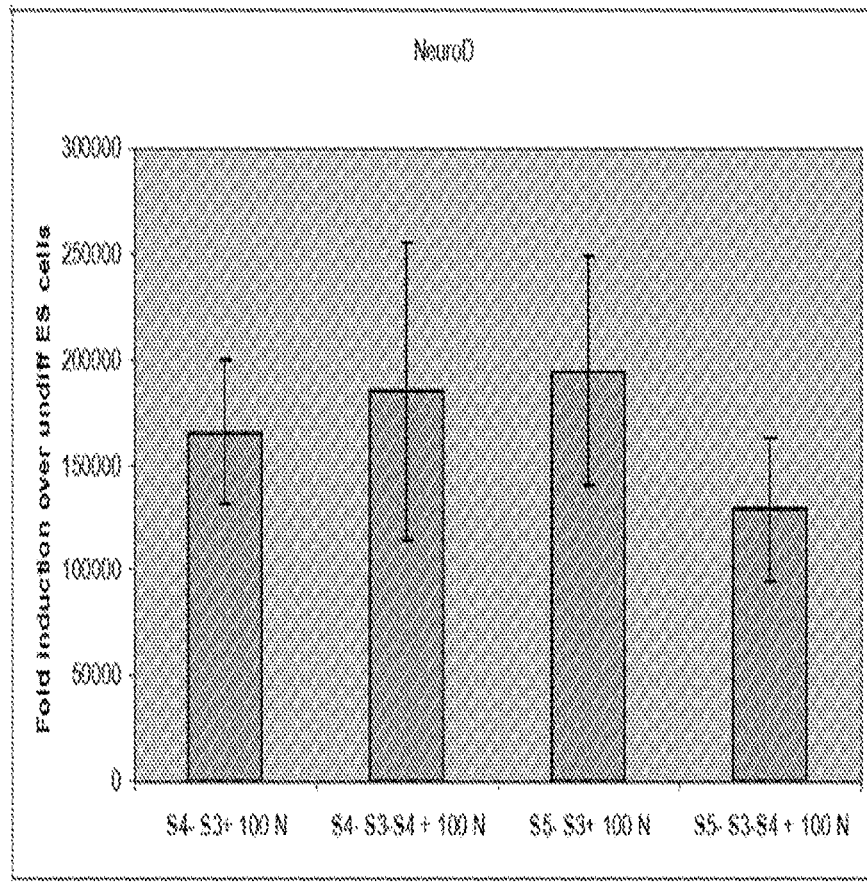
Figure 7E:
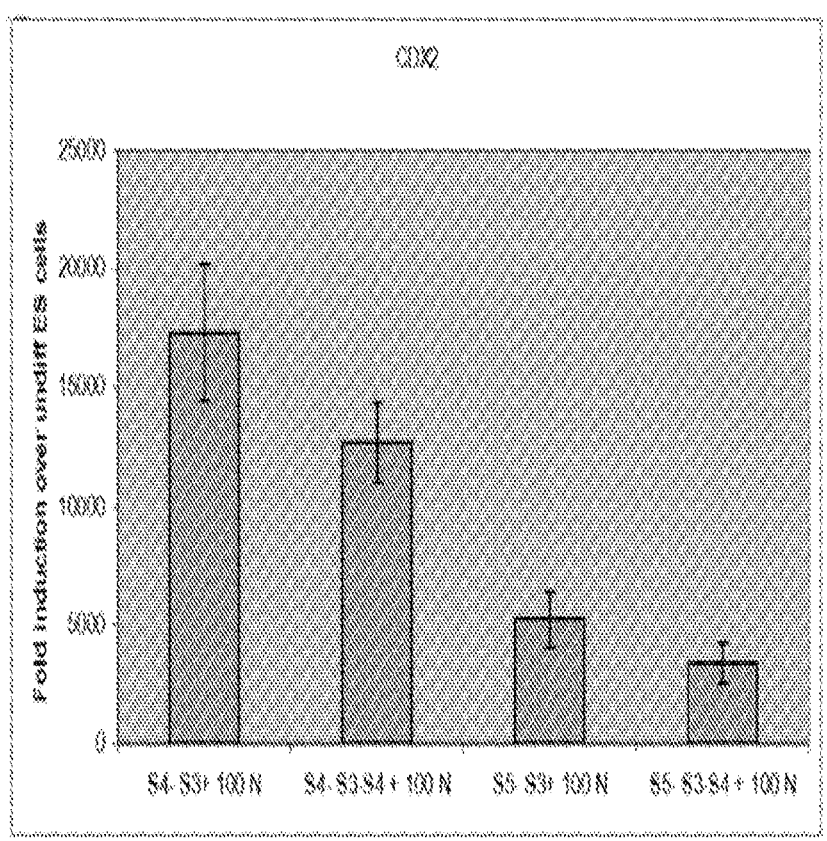
Figure 7F:
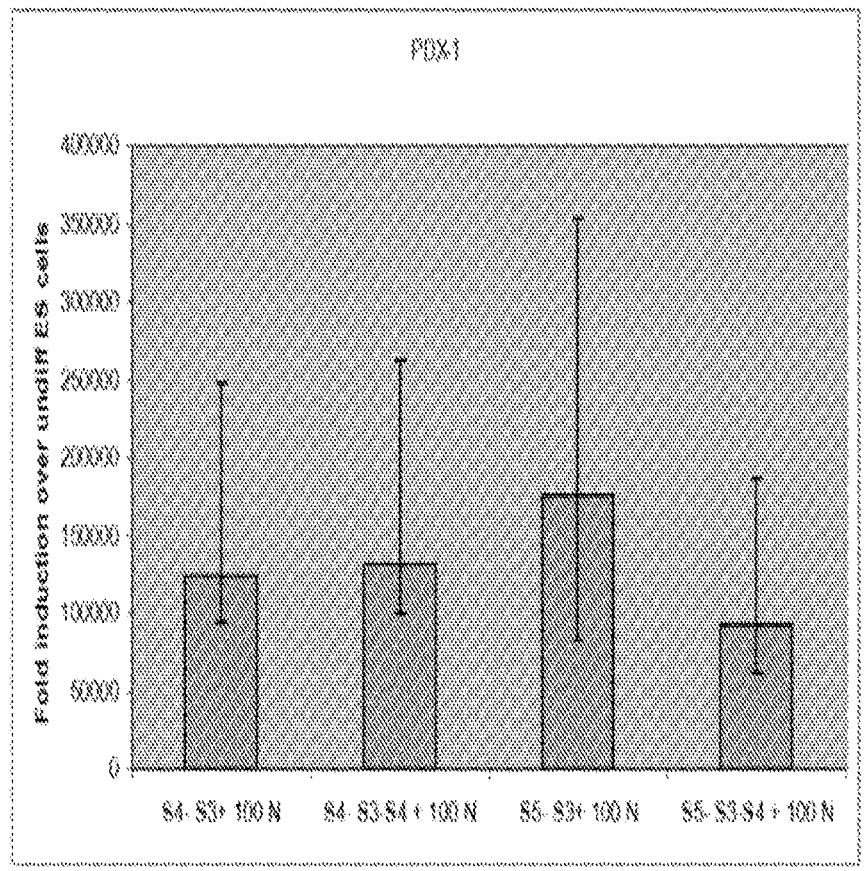

Next, the cells were cultured in DMEM/F12+1% B27 (Invitrogen, CA)+50 ng/ml Exendin-4 (Sigma, MO)+1 µm DAPT (Calbiochem, CA) for six days followed by additional three days incubation in DMEM/F12+1% B27 (Invitrogen, CA)+50 ng/ml Exendin-4 (Sigma, MO)+50 ng/ml IGF (Peprotech, N.J.)+50 ng/ml HGF (R&D Systems, MN). An outline of the procedure is depicted in FIGS. 1A-1C. RNA samples were collected from cultures at various stages of differentiation. FIG. 2 displays the real-time PCR data obtained from cells harvested at stages 3 to 5. There was a significant increase in expression of endocrine markers, such as insulin and glucagon observed in cells at stages 4 and 5, along with an increase in expression of NeuroD.

Example 3

The Effects of Various Compounds on the Expression of Markers Characteristic of the Pancreatic Endocrine Lineage in Pluripotent Stem Cells Treated According to the Differentiation Protocol Outlined in FIG. 1A.

Cells of the human embryonic stem cell line H1, at passage 51 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+ 20 ng/ml FGF7+0.25 µm Cyclopamine-KAAD (#239804, Calbiochem, CA) for three days followed by four day incubation in DMEM/F12+1% B27 (Invitrogen, CA)+20 ng/ml FGF7+0.25 µm Cyclopamine-KAAD+2 µm Retinoic acid (RA) (Sigma, MO).

Next, the cells were cultured in DMEM/F12+1% B27 (Invitrogen, CA)+50 ng/ml Exendin-4 (Sigma, MO)+1 µm DAPT (Calbiochem, CA) for six days followed by additional three days incubation in DMEM/F12+1% B27 (Invitrogen, CA)+50 ng/ml Exendin-4 (Sigma, MO)+50 ng/ml IGF (Peprotech, N.J.)+50 ng/ml HGF (R&D Systems, MN). Some of the cultures were treated with 1 µM of the following compounds at either stage 3, stage 4, or stages 3+4: MEK/ MAPK inhibitor (2'-Amino-3'-methoxyflavone) (PD98059, Calbiochem, CA), RAF kinase inhibitor (5-Iodo-3-R3,5-dibromo-4-hydroxyphenyl)methylenel-2-indolinone) (#553008, Calbiochem, CA), SMAD3 inhibitor (6,7-Dimethyl-2-((2E)-3-(1-methyl-2-phenyl-1Hpyrrolo[2,3-b]pyridin-3-yl-prop-2-enoyl))-1,2,3,4-tetrahydroisoquinoline) (#566405, Calbiochem, CA), AKT inhibitor (1L6-Hydroxymethyl-chiroinositol-2-(R)-2-O-methyl-3-O-octadecyl-sn-glycerocarbonate) (#124005, Calbiochem, CA), MEK inhibitor (#444937 Calbiochem, CA), and TGF-B receptor I inhibitor (2-(3-(6-Methylpyridin-2-yl)-1H-pyrazol-4-yl)-1,5-naphthyridine) (inhibits activin receptor-like kinase 5, #616452, Calbiochem, CA).

FIGS. 3A-3E display the real-time PCR data obtained from cell harvested at the end of stages 3 to 5, treated with the conditions indicated. Note that addition of the TGF-B receptor I kinase inhibitor (2-(3-(6-Methylpyridin-2-yl)-1H-pyrazol-4-yl)-1,5-naphthyridine) to cells at stage 4 or to cells stages 3 and 4 significantly enhanced expression of insulin, glucagon, NeuroD, and NKX2.2 while marginally affecting the expression of PDX-1 at the end of stage 5. Addition of the TGF-B receptor I kinase inhibitor (2-(3-(6-Methylpyridin-2-yl)-1H-pyrazol-4-yl)-1,5-naphthyridine) only at cells at stage 3 marginally upregulated expression of endocrine markers in cells at the end of stage 5.

Example 4

The Effect of the Addition of TGF-β Receptor I Kinase Inhibitor on the Expression of Markers Characteristic of the Pancreatic Endocrine Lineage in Pluripotent Stem Cells Treated According to the Differentiation Protocol Outlined in FIG. 1A Cells of the human embryonic stem cell line H1, at passage 44 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+ 20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO).

Next, cells were cultured in DMEM/F12+1% B27 (Invitrogen, CA)+50 ng/ml Exendin-4 (Sigma, MO)+1 μm DAPT (Calbiochem, CA) for six days followed by additional three days incubation in DMEM/F12+1% B27 (Invitrogen, CA)+ 50 ng/ml Exendin-4 (Sigma, MO)+50 ng/ml IGF (Peprotech, N.J.)+50 ng/ml HGF (R&D Systems, MN). Some of the cultures were treated with 1 μM of TGF-B receptor I kinase inhibitor (2-(3-(6-Methylpyridin-2-yl)-1H-pyrazol-4-yl)-1,5-naphthyridine) (an inhibitor of activin receptor-like kinase 5, #616452, Calbiochem, CA) at stage 4, stage 5, or stages 4 and 5.

FIGS. 4A-4E display the real-time PCR data from cells harvested at the end of stages 3 to 5+/− kinase inhibitor at stages 4 to 5. Note that addition of the TGF-B receptor I kinase inhibitor (2-(3-(6-Methylpyridin-2-yl)-1H-pyrazol-4-yl)-1,5-naphthyridine) to cells at stage 4 or stages 4 and 5 significantly enhanced expression of insulin, glucagon, NeuroD, and NKX2.2 while marginally affecting expression of PDX-1 at the end of stage 5. Addition of the TGF-B receptor I kinase inhibitor (2-(3-(6-Methylpyridin-2-yl)-1H-pyrazol-4-yl)-1,5-naphthyridine) only at stages 5 marginally upregulated expression of endocrine markers at the end of stage 5.

Example 5

The Effect of Various TGF-β Receptor I Kinase Inhibitors on the Expression of Markers Characteristic of the Pancreatic Endocrine Lineage in Pluripotent Stem Cells Treated According to the Differentiation Protocol Outlined in FIG. 1A Cells of the human embryonic stem cell line H1, at passage 41 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+ 20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO).

Next, cells were cultured in DMEM/F12+1% B27 (Invitrogen, CA)+50 ng/ml Exendin-4 (Sigma, MO)+1 μm DAPT (Calbiochem, CA) for six days followed by additional three days incubation in DMEM/F12+1% B27 (Invitrogen, CA)+ 50 ng/ml Exendin-4 (Sigma, MO)+50 ng/ml IGF (Peprotech, N.J.)+50 ng/ml HGF (R&D Systems, MN). Some of the cultures were treated with 1-10 μm of TGF-B receptor I kinase inhibitor (ALK5 inhibitor II) (2-(3-(6-Methylpyridin-2-yl)-1H-pyrazol-4-yl)-1,5-naphthyridine) (an inhibitor of activin receptor-like kinase 5, #616452, Calbiochem, CA) or TGF-B receptor I inhibitor I (ALK5 inhibitor I) ([3-(Pyridin-2-yl)-4-(4-quinonyl)]-1H-pyrazole) (#616451, Calbiochem, CA) at stages 4 and 5.

FIGS. 5A-5E display the real-time PCR data from cells harvested at the end of stages 4-5+/− ALK5 inhibitor I or II. Note that addition of the ALK5 inhibitor I or II at 1-10 μm to stages 4 and 5 significantly enhanced expression of insulin, glucagon, PDX-1 and NeuroD, at the end of stages 4 to 5 as compared to controls (standard treatment). All the samples were in triplicate.

Example 6

The Effect of Noggin and ALK5 Inhibitors on the Expression of Markers Characteristic of the Pancreatic Endocrine Lineage in Pluripotent Stem Cells Treated According to the Differentiation Protocol Outlined in FIG. 1A Cells of the human embryonic stem cell line H1, at passage 41 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+ 20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO)+0-500 ng/ml of Noggin (R & D Systems, MN).

Next, cells were cultured in DMEM/F12+1% B27 (Invitrogen, CA)+50 ng/ml Exendin-4 (Sigma, MO)+1 um DAPT (Calbiochem, CA)+1 μm ALK5 inhibitor II (Calbiochem, Ca) for six days followed by additional three days incubation in DMEM/F12+1% B27 (Invitrogen, CA)+50 ng/ml Exendin-4 (Sigma, MO)+50 ng/ml IGF (Peprotech, N.J.)+ 50 ng/ml HGF (R&D Systems, MN)+1 μM ALK5 inhibitor II.

FIGS. 6A-6G display the real-time PCR data from cells harvested at the end of stages 3-5+/−0-100 ng/ml Noggin. Addition of 100 ng/ml of Noggin at stage 3 marginally enhanced expression of insulin and glucagon at the end of stage 4, while significantly suppressing the expression of albumin and CDX2 as compared to untreated samples. Addition of 500 ng/ml of Noggin did not affect expression of PDX-1 but did significantly diminish expression of endocrine markers, along with albumin and CDX2. Albumin is a marker for liver precursor cells, while CDX2 is marker for gut cells.

Example 7

The Effect of the Addition of Noggin at Stage 3 and ALK5 Inhibitors at Stages 4 and 5 on the Expression of Markers Characteristic of the Pancreatic Endocrine Lineage in Pluripotent Stem Cells Treated According to the Differentiation Protocol Outlined in FIGS. 1A-1C Cells of the human embryonic stem cell line H1, at passage 44 were cultured on MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO)+100 ng/ml of Noggin (R & D Systems, MN).

Next, cells were cultured in DMEM/F12+1% B27 (Invitrogen, CA)+50 ng/ml Exendin-4 (Sigma, MO)+1 μm DAPT (Calbiochem, CA)+1 μm ALK5 inhibitor II (Calbiochem, Ca)+/−100 ng/ml of Noggin for six days followed by additional three days incubation in DMEM/F12+1% B27 (Invitrogen, CA)+50 ng/ml Exendin-4 (Sigma, MO)+50 ng/ml IGF (Peprotech, N.J.)+50 ng/ml HGF (R&D Systems, MN)+1 μM ALK5 inhibitor II.

FIGS. 7A-7F display the real-time PCR data from cells harvested at the end of stages 4 to 5+/−100 ng/ml Noggin. Addition of 100 ng/ml of Noggin at stage 3+4 plus addition of ALK5 inhibitor II dramatically enhanced expression of insulin and glucagons at stages 4-5. In particular, addition of Noggin at both stages Sand 4 significantly enhanced expression of NGN3, an endocrine precursor marker, while significantly suppressing the expression of albumin and CDX2 as compared to untreated samples.

FIGS. 8A-8D depict a phase contrast image of the cultures according to the above protocol. In some of the cultures, stage 5 was extended from 3 days to 21 days. By day 10-12 of culture in stage 5 media, there were distinct clusters of cells resembling human islets present throughout the culture plate. FIGS. 8A-8B show images of day 6 cultures in stage 5 while FIGS. 8C-8D show images of day 12 stage 5 cultures. Some of the clusters were manually removed, plated on 1:30 MATRIGEL-coated plates in stage 5 media. After 2 days of incubation, the clusters were stained for insulin and glucagon. The majority of the cells in the clusters as shown in FIGS. 9A-9B were positive for human insulin. In order to further optimize the dose of the BMP inhibitor, Noggin; cultures were treated at stage 2-4 with 0, 10, 50, or 100 ng/ml of Noggin. FIG. 10 depicts expression of NGN3 at stage 4 for cultures treated with varying doses of Noggin at stages 2-4.

It appears that 50-100 ng/ml of Noggin results in maximal expression of NGN3 at stage 4.

Example 8

The Effect of the Addition of Noggin at Stages 3-4, Netrin at Stage 4 and ALK5 Inhibitors at Stage 4 on the Expression of Markers Characteristic of the Pancreatic Endocrine Lineage in Pluripotent Stem Cells Treated According to the Differentiation Protocol Outlined in FIGS. 1A-1C Cells of the human embryonic stem cell line H1, at passage 48 were cultured on MATRIGEL™ coated dishes (1:30 dilution) and exposed to DMEM/F12 medium supplemented with 2% fatty-acid BSA, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% BSA and 100 ng/ml Activin-A (AA) for an additional two days. Next the cultures were treated with DMEM/F12+2% FBS+20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO)+100 ng/ml of Noggin (R & D Systems, MN).

Next, cells were cultured incubation in DMEM/F12+1% B27 (Invitrogen, CA)+50 ng/ml Exendin-4 (Sigma, MO)+1 μm DAPT (Calbiochem, CA)+1 μm ALK5 inhibitor II (Calbiochem, Ca)+/−100 ng/ml of Noggin+100 ng/ml Netrin-4 for three days.

FIGS. 11A-11F display the real-time PCR data from cells harvested at the end of stage 4+/−100 ng/ml Netrin-4 at stage 4. Addition of 100 ng/ml of Noggin at stage 3 and 4 plus addition of ALK5 inhibitor II and 100 ng/ml of Netrin-4 at stage 4 dramatically enhanced expression of NGN3, NeuroD, and Pax4 in cells harvested at the end of stage 5.

In some of the stage 4 cultures, Noggin was omitted while Netrin-4 plus Alk5 inhibitor were added. FIGS. 12A-12D show that omission of Noggin at stage 4 did significantly reduce expression of NGN3, NKX2.2, and NeuroD while moderately affecting expression of insulin and glucagon in cells harvested at the end of stage 5.

Example 9

In Vitro Glucose Stimulated Insulin Secretion (GSIS) by Pluripotent Stem Cells Treated According to the Differentiation Protocol Outlined in FIG. 1B Cells of the human embryonic stem cell line H1, at passage 48 were cultured on MATRIGEL™ coated dishes (1:30 dilution) and exposed to DMEM/F12 medium supplemented with 2% fatty-acid BSA, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% BSA and 100 ng/ml Activin-A (AA) for an additional two days. Next the cultures were treated with DMEM/F12+2% FBS+20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO)+100 ng/ml of Noggin (R & D Systems, MN).

Next, cells were cultured in DMEM/F12+1% B27 (Invitrogen, CA)+50 ng/ml Exendin-4 (Sigma, MO)+1 μm DAPT (Calbiochem, CA)+1 μm ALK5 inhibitor II (Calbiochem, Ca)+/−100 ng/ml of Noggin+100 ng/ml Netrin-4 for six days, followed by additional 3-21 days of incubation in DMEM/F12+1% B27 (Invitrogen, CA)+50 ng/ml Exendin-4 (Sigma, MO)+50 ng/ml IGF (Peprotech, N.J.)+50 ng/ml HGF (R&D Systems, MN)+1 μM ALK5 inhibitor II.

Stage 5 cultures at days 6, 8, 12, and 20 were tested for GSIS by 1 hr wash in KREBS buffer (Krebs-Ringer solution: 0.1% BSA, 10 mM HEPES, 5 mM NaHCO$_3$, 129 mM NaCl, 4.8 mM KCl, 2.5 mM CaCl$_2$, 1.2 mM KH$_2$PO$_4$, 1.2 mM MgSO$_4$, 5 mM NaHCO$_3$) at 37° C., followed by 1 hr incubation in KREBS buffer plus 2 mM D-glucose, and an addition 1 hr incubation in KREBS buffer plus 20 mM D-glucose. Following each incubation, the supernatant was removed and frozen at −20° C. for further analysis. Levels of secreted C-peptide were assayed using the ultra-sensitive C-peptide ELISA (Alpco Diagnostics, Sweden). FIGS. 13A-13C depict the levels of secreted human C-peptide in response to an in vitro glucose challenge. Early and intermediate incubation periods in stage 5 did not result in significant stimulation index (ration of secreted C-peptide at high glucose to low glucose), while samples incubated in stage 5 media for 20 days showed robust stimulation in response to glucose. This indicates that prolonged exposure to stage 5 media does result in maturation of clusters, which show evidence of GSIS.

Example 10

The Effect of the Addition of Netrin-1 or Netrin-2 on the Expression of Markers Characteristic of the Pancreatic Endocrine Lineage in Pluripotent Stem Cells Treated According to the Differentiation Protocol Outlined in FIG. 1B Cells of the human embryonic stem cell line H1, at passage 44 were cultured n MATRIGEL™ coated dishes (1:30 dilution) and exposed to DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days. Next the cultures were treated with DMEM/F12+2% FBS+20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO).

Next, cells were cultured in DMEM/F12+1% B27 (Invitrogen, CA)+50 ng/ml Exendin-4 (Sigma, MO)+1 μm DAPT (Calbiochem, CA) for six days followed by additional three days incubation in DMEM/F12+1% B27 (Invitrogen, CA)+50 ng/ml Exendin-4 (Sigma, MO)+50 ng/ml IGF (Peprotech, N.J.)+50 ng/ml HGF (R&D Systems, MN). In some of the cultures 50 ng/ml of Netrin-1 or Netrin-2 (R&D Systems, MN) was added at stage 2-5. FIG. 14 displays the real-time PCR data from cells harvested at stage 5+/−50 ng/ml of Netrin-1 or Netrin-2 at stages 2 to 5. Addition of either Netrin-1 or Netrin-2 did significantly upregulate expression of glucagon and insulin in cells harvested at the end of stage 5.

Example 11

An Alternative Method to Induce the Expression of Markers Characteristic of the Definitive Endoderm Lineage Cells of the human embryonic stem cell line H1, at passage 48 were cultured on MATRIGEL™ coated dishes (1:30 dilution) and differentiated to cells expressing markers characteristic of the definitive endoderm lineage either by:

a. Culturing in RPMI medium supplemented with 1% B27 supplement (Invitrogen, Ca), and 50 ng/ml Activin-A (R&D Systems, MN) plus 1 mM Na Butyrate (Sigma, MO) for one day followed by treatment with RPMI media supplemented with 1% B27 supplement (Invitrogen, Ca), and 50 ng/ml Activin-A (R&D Systems, MN) plus 0.5 mM Na Butyrate (Sigma, MO) for an additional three days, or b. DMEM/F12 medium supplemented with 0.5% FBS, and 100 ng/ml Activin-A (R&D Systems, MN) plus 20 ng/ml WNT-3a (Catalog #1324-WN-002, R&D Systems, MN), for two days followed by treatment with DMEM/F12 media supplemented with 2% FBS and 100 ng/ml Activin-A (AA) for an additional two days.

Next the cultures were treated with DMEM/F12+2% FBS+20 ng/ml FGF7+0.25 μm Cyclopamine-KAAD (#239804, Calbiochem, CA) for three days followed by four day incubation in DMEM/F12+1% B27 (Invitrogen, CA)+20 ng/ml FGF7+0.25 μm Cyclopamine-KAAD+2 μm Retinoic acid (RA) (Sigma, MO). Next cells were incubated in DMEM/F12+1% B27 (Invitrogen, CA)+50 ng/ml Exendin-4 (Sigma, MO)+1 μm DAPT (Calbiochem, CA)+1 um ALK5 inhibitor II (Calbiochem, Ca) for three days.

Induction of cultures to definitive endoderm using alternative method a) above resulted in a 78% expression of CXCR4 as measured by FACS, as compared to 56% CXCR4 expression by alternative method b) above. CXCR4 is regarded as a marker for definitive endoderm cells.

FIGS. 15A-15F display the real-time PCR data from cells harvested at the end of stage 5 using either alternative method a) or b). It appears that alternative method a) can also be used to induce expression of pancreatic endoderm and endocrine markers.

Example 12

Differentiation of Human Embryonic Stem Cells Cultured in the Absence of Serum, on Tissue Culture Substrate Coated with MATRIGEL™ to Pancreatic Endocrine Cells Cells of the human embryonic stem cell line H1, at passage 52 were cultured on MATRIGEL™ coated dishes (1:30 dilution) and exposed to exposed to RPMI medium supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, N.J.), for one day, followed by treatment with RPMI media supplemented with 2% BSA and 100 ng/ml activin A plus 8 ng/ml of bFGF for an additional two days. Next the cultures were treated with DMEM/F12+2% BSA+50 ng/ml FGF7+0.25 μm Cyclopamine-KAAD (#239804, Calbiochem, CA) for two days, followed by four days incubation in DMEM/F12+1% B27 (Invitrogen, CA)+50 ng/ml FGF7+0.25 μm Cyclopamine-KAAD+2 μM retinoic acid (RA) (Sigma, MO)+100 ng/ml of Noggin (R & D Systems, MN). Next, the cells were incubated in DMEM/F12+1% B27 (Invitrogen, CA)+100 ng/ml Noggin+1 μm DAPT (Catalog #565784, Calbiochem, CA)+1 μm ALK5 inhibitor II (Catalog #616452, Calbiochem, Ca)+100 ng/ml of Netrin-4 (R&D Systems, MN) for three days, followed by additional seven days incubation in DMEM/F12+1% B27 (Invitrogen, CA)+1 μm ALK5 inhibitor II (Calbiochem, Ca). A last stage was added to further mature the endocrine cultures, which consisted of seven day treatment in DMEM/F12+1% B27 (Invitrogen, CA). Except for the last stage, all other stages included daily media changes. An outline of the procedure is depicted in FIG. 1C. At each stage cell number was calculated using a hemocytometer and RNA was collected for PCR analysis. All samples were collected in triplicate.

FIGS. 16A-16B display the CXCR4 expression as measured by FACS and real-time PCR data for stage 1 at day 3. Fold change in expression is shown relative to undifferentiated H1 ES cells. FIGS. 16C-16N depict real-time PCR data for key pancreatic and endocrine markers in cells harvested at the end of stages 2-6. FIG. 17 depicts the number of cells at the end of stages 1-6.

Example 13

C-Peptide and Pro-Insulin Content in Pluripotent Stem Cells Treated According to the Differentiation Protocol Outlined in FIG. 1C Cells of the human embryonic stem cell line H1, at passage 42 were cultured on MATRIGEL™ coated dishes (1:30 dilution) and differentiated according to the protocol outlined in FIG. 1C, as described in Example 12 above.

The cells were washed in Krebs-Ringer buffer (129 mM NaCl, 4.8 mM KCl, 1.2 mM $NaH_2PO_4$, 1.2 mM $MgSO_4$, 2.5 MM $CaCl_2$, 5 mM $NaHCO_3$, 10 mM HEPES, 0.3% (wt/vol) BSA) and incubated with the Krebs buffer for 15 mins followed by 45 mins incubation in Krebs buffer spiked with 2 mM D-glucose at 37° C., 5% $CO_2$, 95% Air. 0.5 ml of supernatant was collected and the remaining media was aspirated and replaced with Krebs buffer spiked with one of the following stimuli: 20 mM D-glucose (HG), 30 mM KCl, 100 µM tolbutamide (tol), 100 mM IBMX, 2 µM BAY K8644, or 10 mM ketoisocaproic acid (MC) for 45 mins at 37° C., 5% $CO_2$, 95% Air. 0.5 ml of supernatant was collected and the remaining media was discarded. The supernatants were analyzed for human C-peptide content using C-peptide ELISA kit (Catalog #80-CPTHU-E01, Alpco Diagnostics, NH). The samples had to be routinely diluted 5-10 fold to fall within the linear range of the standards provided in the kit.

FIG. 18 shows the C-peptide release following stimulation with various stimuli. Stimulation index (C-peptide concentration in stimulation supernatant divided by C-peptide concentration in basal supernatant containing 2 mM glucose) for each agent is also shown on the graph.

In order to measure the C-peptide, Pro-insulin, and DNA contents of stage 6 cultures, 6-well plates containing stage 6 cultures were treated with 500 µl of cell lysis buffer per well (10 mM Tris-HCL+1 mM EDTA, pH 7.5) followed by 30 sec sonication. C-peptide content and Pro-insulin content were measured using C-peptide ELISA kit (Catalog #80-CPTHU-E01, Alpco Diagnostics, NH) and Pro-insulin ELISA kit (Catalog #11-1118-01, Alpco Diagnostics, NH), respectively. DNA content of the lysates was quantified using Quant-IT™ DNA kit (Catalog #P7589, Invitrogen, Ca). The samples had to be routinely diluted 500-1000 fold to fall within the linear range of the standards provided in the kits. FIG. 19 shows the C-peptide content and pro-insulin content normalized to DNA for three different wells of a 6-well plate containing stage 6 cultures. As comparison, C-peptide and pro-insulin contents of three different adult human cadaver islet samples were also measured. Note that the data reflects the insulin content of the entire culture and not only the clusters present in the culture.

Example 14

FACS Analysis of Pluripotent Stem Cells Treated According to the Differentiation Protocol Outlined in FIG. 1C Cells of the human embryonic stem cell line H1, were cultured on MATRIGEL™ coated dishes (1:30 dilution) and differentiated according to the protocol outlined in FIG. 1C, as described in Example 12 above. Cells were dissociated into single cells from monolayer cultures using TrypLE Express (Invitrogen, Carlsbad, Calif.) and washed in cold PBS. For fixation, cells were resuspended in 200-300 µl Cytofix/Cytoperm Buffer (BD 554722, BD, Ca) and incubated for 30 min at 4° C. Cells were washed two times in 1 ml Perm/Wash Buffer Solution (BD 554723) and resuspended in 100 µl staining/blocking solution containing 2% normal goat serum in Perm/Wash buffer. For flow cytometric analysis, cells were stained with the following primary antibodies: Anti-Insulin (Rabbit mAb, Cell Signaling No. C27C9; 1:100 dilution), Anti-Glucagon (Mouse Mab, Sigma No. G2654, 1:100); Anti-Synaptophysin (Rabbit Polyclonal antibody, DakoCytomation No A0010, 1:50); Cells were incubated for 30 min at 4° C. followed by two washes in Perm/Wash buffer and further 30 min incubation in appropriate secondary antibodies as follows: Goat anti-Rabbit Alexa 647 (Invitrogen No. A21246) or Goat anti-Mouse 647 (Invitrogen No. A21235); Goat anti-Rabbit R-PE (BioSource No. ALI4407). All secondary antibodies were used at 1:200 dilution. Cells were washed at least once in Perm/Wash buffer and analyzed using BD FACSArray. A least 10,000 events were acquired for analysis. Controls included undifferentiated H1 cells and b-TC (ATCC, VA) cell line. FIGS. 20A-20C show the percentage insulin positive and synapthophysin+ cells in stage 6 cultures.

Example 15

Addition of Chordin at Stages 3 and 4 of the Differentiation Protocol Outlined in FIG. 1C Up-regulate the Expression of Markers Characteristic of the Pancreatic Endocrine Lineage Cells of the human embryonic stem cell line H1, at passage 52 were cultured on MATRIGEL™ coated dishes (1:30 dilution) and differentiated according to the protocol outlined in FIG. 1C, with the exception that that 50-100 ng/ml of Chordin (R&D Systems, MN) was added to stages 3-4 instead of Noggin. Similar to Noggin, Chordin is also a known inhibitor of BMP signaling. Analysis of stage 6 cultures by FACS (FIGS. 21A-21B) revealed very similar expression of insulin and synaptophysin as observed with addition of Noggin at stages 3-4.

Example 16

Differentiation of Human Embryonic Stem Cells Cultured in the Absence of Serum, on Tissue Culture Substrate Coated with MATRIGEL™ to Pancreatic Endocrine Cells Cells of the human embryonic stem cell line H9, at passage 39 were cultured on MATRIGEL™ coated dishes (1:30 dilution) and differentiated according to the protocol outlined in FIG. 1C, as described in Example 12 above. RNA was collected at the end of stages 1-6. FIGS. 22A-22L depict real-time PCR data for key pancreatic and endocrine markers harvested at the end of stages 3-6. Similar to results obtained with H1 line, H9 cells were able to express markers characteristic of the pancreatic endocrine lineage.

Example 17

The Effect of Media Supplements on the Ability of Pluripotent Stem Cells to Differentiate into Pancreatic Endocrine Cells Cells of the human embryonic stem cell line H1, at passage 39 were cultured on MATRIGEL™ coated dishes (1:30 dilution) and differentiated according to the protocol outlined in FIG. 1C, with the exception that in some cultures, DMEM/F12 basal media was supplemented with 0.25-1% B27 or 1% N2 (Invitrogen, Ca)+2% BSA. All other components of the differentiation protocol were kept as outlined in Example 12. Samples were collected in triplicate at the end of stages 3, 5 and 6 and analyzed by real-time PCR. FIGS. 23 A-D depict real-time PCR data for key pancreatic and endocrine markers from cells harvested at the end of stages 3, 5, and 6. Use of N2/BSA as a replacement for B27 resulted in very similar expression of key pancreatic endocrine markers. Furthermore, concentration of B27 could be lowered to 0.25% without significantly affecting expression of key pancreatic endocrine markers.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A composition, comprising pancreatic endoderm cells, pancreatic endocrine cells, and an effective amount of inhibitor of TGF-βR-1 kinase wherein the effective amount of inhibitor of TGF-βR-1 kinase differentiates the pancreatic endoderm cells into pancreatic endocrine cells.

2. The composition of claim 1, wherein the inhibitor of TGF-βR-1 kinase is an ALK5 inhibitor.

3. The composition of claim 2, wherein the ALK5 inhibitor is ALK5 inhibitor II or ALK5 inhibitor I.

4. The composition of claim 1, wherein there are more pancreatic endocrine cells than pancreatic endoderm cells in the composition.

5. The composition of claim 1, wherein the inhibitor of TGF-βR-1 kinase is (2-(3-(6-Methylpyridin-2-yl)-1H-pyrazol-4-yl)-1,5-naphthyridine) or [3-(Pyridin-2-yl)-4-(4-quinonyl)]-1H-pyrazole.

6. The composition of claim 1, wherein the cell culture comprises 0.1 μM to about 100 μM of the TGF-βR-1 kinase inhibitor.

7. The composition of claim 1, wherein the pancreatic endoderm cells and the pancreatic endocrine cells are derived from human embryonic stem cells.

8. The composition of claim 1, further comprising an effective amount of exendin-4 and/or an effective amount of a notch pathway inhibitor.

9. The composition of claim 8, wherein the cell culture comprises the notch pathway inhibitor, and wherein the notch signaling pathway is a γ-secretase inhibitor.

10. The composition of claim 9, wherein the γ-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester.

11. A method of differentiating human pancreatic endoderm cells into human pancreatic endocrine cells, comprising:

treating the human pancreatic endoderm cells with an inhibitor of TGF-βR-1 kinase, thereby differentiating the human pancreatic endoderm cells into the human pancreatic endocrine cells.

* * * * *